United States Patent
DaCunha et al.

(10) Patent No.: US 8,686,123 B2
(45) Date of Patent: Apr. 1, 2014

(54) USE OF MANGANESE PEROXIDASE FOR ENZYMATIC HYDROLYSIS OF LIGNOCELLULOSIC MATERIAL

(75) Inventors: Chris DaCunha, Visalia, CA (US);
Adrian Galvez, Burlingame, CA (US);
Michael Guerini, Gilroy, CA (US);
Manoj Patel, Brampton, CA (US);
Ngim Ung-Ferrell, Clovis, CA (US);
Jennifer Headman, Oceanside, CA (US)

(73) Assignee: Edeniq, Inc., Visalia, CA (US)

( * ) Notice: Subject to any disclaimer, the term of this patent is extended or adjusted under 35 U.S.C. 154(b) by 0 days.

(21) Appl. No.: 13/297,111

(22) Filed: Nov. 15, 2011

(65) Prior Publication Data

US 2012/0149065 A1 Jun. 14, 2012

Related U.S. Application Data

(60) Provisional application No. 61/413,815, filed on Nov. 15, 2010.

(51) Int. Cl.
*C07H 21/04* (2006.01)
*C12P 19/00* (2006.01)
*C12P 7/14* (2006.01)
*C12N 9/08* (2006.01)
*C12N 1/00* (2006.01)
*C12N 15/00* (2006.01)

(52) U.S. Cl.
USPC ............ 536/23.2; 435/192; 435/72; 435/162; 435/254.21; 435/320.1

(58) Field of Classification Search
None
See application file for complete search history.

(56) References Cited

U.S. PATENT DOCUMENTS

| | | | |
|---|---|---|---|
| 5,153,121 | A | 10/1992 | Asther et al. |
| 5,691,193 | A | 11/1997 | Paice et al. |
| 2002/0083492 | A1 | 6/2002 | Iimura et al. |
| 2009/0325240 | A1 | 12/2009 | Daniell |

FOREIGN PATENT DOCUMENTS

| WO | WO 2009/005564 A2 | | 1/2009 |
|---|---|---|---|
| WO | WO-2009-005564 A2 | * | 3/2009 |
| WO | WO-2009-108941 A2 | * | 9/2009 |

OTHER PUBLICATIONS

Chheda, J.N., et al.; "Liquid-phase catalytic processing of biomass-derived oxygenated hydrocarbons to fuels and chemicals"; *Angew. Chem. Int. Ed.*: 2007, pp. 7164-7183; vol. 46.

Gu, L., et al.; "Expression of a *Phanerochaete chrysosporium* manganese peroxidase gene in the yeast *Pichia pastoris*"; *Biotechnology Progress*; 2003, pp. 1403-1409; vol. 19, No. 5.

Miyazaki, C. and Takahashi, H; "Engineering of the $H_2O_2$-binding pocket region of a recombinant manganese peroxidase to be resistant to $H_2O_2$."; *FEBS Letters*; 2001; pp. 111-114; vol. 509.

Miyazaki-Imamura, C. et al.; "Improvement of $H_2O_2$ stability of manganese peroxidase by combinatorial mutagenesis and high-throughput screening using in vitro expression with protein disulfide isomerase"; *Protein Engineering*; 2003; pp. 423-428; vol. 16, No. 6.

Paice, M.G. et al., "Bleaching kraft pulps with oxidative enzymes and alkaline hydrogen peroxide"; *Tappi Journal*; 1995; pp. 161-169; vol. 78, No. 9.

Pfister, TD. et al.; "Kinetic and crystallographic studies of a redesigned manganese-binding site in cytochrome c peroxidase" *J Biol Inorg Chem*; 2007; pp. 126-137; vol. 12.

Ruiz-Duenas F.J., et al.; "Heterologous Expression of *Pleurotus eryngii* Peroxidase Confirms Its Ability to Oxidize $Mn^{2+}$ and Different Aromatic Substrates"; *Applied and Environmental Microbiology*; Oct. 1999; pp. 4705-4707; vol. 65, No. 10; American Society for Microbiology.

Ruis-Duenas, F.J. and Martinez, A.T.; "Microbial degradation of lignin: how a bulky recalcitrant polymer is efficiently recycled in nature and how we can take advantage of this"; *Microbial Biotechnology*; 2009,99. 164-171; vol. 2, No. 2.

Ryu, K., et al.; "Expression in yeast of secreted lignin peroxidase with improved 2,4-dichlorophenol degradability by DNA shuffling"; *Journal of Biotechnology*; 2008, pp. 241-246; vol. 135.

Sunaramoorthy, M. et al.; "The Crystal Structure of Manganese Peroxidase from *Phanerochaete chrysosporium* at 2.06 A Resolution" *J. Biol. Chem*; 1994; pp. 32759-32767; vol. 269, No. 52.

Yee, Kelsey L.; "The role of manganese peroxidase in biomass conversion technologies" Thesis, Oregon State University (http://hdl.handle.net/1957/17700).

International Search Report and Written Opinion issued on Mar. 27, 2012 in PCT/US2011/60862, filed Nov. 15, 2011. 9 pages.

* cited by examiner

*Primary Examiner* — Iqbal H Chowdhury
(74) *Attorney, Agent, or Firm* — Kilpatrick Townsend & Stockton LLP

(57) ABSTRACT

Improved manganese peroxidases, polynucleotides encoding improved manganese peroxidase and vectors and cells thereof are provided, as well as methods for converting a cellulose-containing biomass feedstock to ethanol using improved manganese peroxidases and cells expressing a heterologous manganese peroxidase as disclosed herein.

20 Claims, 26 Drawing Sheets

| | | |
|---|---|---|
| Phlebia | MAFK---QLLTAISI---VSVANAALTRRVACPDGVNTATNAVCCSLFAVRDLIQDQLFD 54 | (SEQ ID NO:6) |
| Trametes | MAFKTLASLLSVLVT---IQVASGALTRRVACPDGVNTATNAACCQLFAVRDDIQQNLFD 57 | (SEQ ID NO:1) |
| Pleurotus | MTFASLSALVLVFAVTVQVAQAVSLPQKRATCAGGQVTAN-AACCVLFPLMEDLQKNLFD 59 | (SEQ ID NO:3) |
| Ganoderma | M-FSKVFLSLVVLAS--SVAAAVPTVGRRATCANGKTTAN-DACCVWFDVLDDIQENLFH 56 | (SEQ ID NO:5) |
| | | |
| Laccaria | MAVALFSTLITLLFG--AQIANAAGLSNQVTCSTGFVTSN-KACCPLFPIVDNIQQNLHG 57 | (SEQ ID NO:2) |
| Phanerochaete | MAFKSLIA-FVALAA-----AVRAAP---TAVCPDGTRVSH-AACCAFIPLAQDLQETIFQ 51 | (SEQ ID NO:7) |
| Gelatoporia | MAFASLLA-LVALAA----TVRAAPSSSSVTCSDGTVPD-SMCCDFIPLAQDLQSMVLQ 54 | (SEQ ID NO:8) |
| Lentinula | MAFSTMILPFVALALS--TVNAAPAAQNARCSDGTVPN-SICCDFIPLAQDLTETLFE 56 | (SEQ ID NO:4) |
| | | |
| Phlebia | GGECGEHVESLRLTFHDAIGISPTIASTGVFGGGCADGSIAIFAEIETNFHANNGVDEI 114 | (SEQ ID NO:6) |
| Trametes | GGECGEHVESLRLTFHDAIGISPSIASRGQFGGGCADGSIALFEDIETNFHANLGVDEI 117 | (SEQ ID NO:1) |
| Pleurotus | DGACGEDAHEALRLTFHDAIGFSPSPSRGVMG----CADGSVITFSDTEVNFPANLGIDEI 114 | (SEQ ID NO:3) |
| Ganoderma | GGQCGEDAHESLRLTFHDAIAFSPALTAAGQFGGGCADGSIIAHSDVELTYPVNDGLDEI 116 | (SEQ ID NO:5) |
| Laccaria | GGACGFGAHTAIRLRLSFHDAIGFSIHGGKGG-----CADGSILIFNTTELAYDANVGIDDI 112 | (SEQ ID NO:2) |
| Phanerochaete | N-ECGEDAHEVIRLTFHDAIAISRSQGPKAG---GGADSMLLFPTVEPNFSANNGIDDS 107 | (SEQ ID NO:7) |
| Gelatoporia | N-ECGEDAHEIIRLTFHDAIAISQSLPPSAG---TGADSMLLFPLVEPBFQASNGIDDS 110 | (SEQ ID NO:8) |
| Lentinula | N-QCGETAHEVLRLSFHDAIAISQSLGPSAG---GGADSMLIFPDVEPNFAANLGISDS 112 | (SEQ ID NO:4) |
| | | |
| Phlebia | IGEQAPFIQM---TNMTTADFIQFAGAVGVSNCPGAPALPVFVGRPDATQPAPDKTVPEP 171 | (SEQ ID NO:6) |
| Trametes | IDEQRPFIAR---HNLTTADFIQFAGAIGVSNCPGAPQLDVFIGRPDATQPAPDLTVPEP 174 | (SEQ ID NO:1) |
| Pleurotus | VEAEKPFLAR---HNISAGDLVHFAGTLAVTNCPGAPRIPFFLGRPPAKAASPIGLVPEP 171 | (SEQ ID NO:3) |
| Ganoderma | VEASRPFAIK---HNVSFGDFIQFAGAVGVANCNGGPQLSFFAGRSNDSQPSPPNLVPLP 173 | (SEQ ID NO:5) |
| Laccaria | TADQWPVFQT---TGLSAGDFLHLAAAVGTANCPGAPRLQYMFGRPPVAPAPDNTVPKP 169 | (SEQ ID NO:2) |
| Phanerochaete | VNNLIPFMQK--HNTISAADLVQFAGAVALSNCPGAPRLEFLAGRPNKTIAAVDGLIPEP 165 | (SEQ ID NO:7) |
| Gelatoporia | VNNLIPFLSS--HPNITAGDLVQFAGAVALTNCPGAPR-ELLAGRKNAVAPAIDGLIPVP 167 | (SEQ ID NO:8) |
| Lentinula | VNDLAPFLASGKFPTITAGDMIQFGAAVAVGLCPGAPQLEFRAGRPNATAPAVDGLIPEP 172 | (SEQ ID NO:4) |

*FIG. 1A*

```
Phlebia         FDTVTSILARFADAGFSSAEVVALLASHTIAAADHYDPSIPGTPFDSTPEIPDTQFFIE 231  (SEQ ID NO:6)
Trametes        FDTVTSIIERFSDAGFFTPAEIVALLVSHTIAAADHYDPSIPGTPFDSTPEEFDTQFFIE 234  (SEQ ID NO:1)
Pleurotus       FDTITDILARMDDAG-FVSVEVWLLSAHSVAAADHVDETIPGTPFDSTPNLFDSQIFIE 230  (SEQ ID NO:3)
Ganoderma       SDTAITILSRFSDAG-FSPAELVALLVSHTVGSQNTYDSSIPGAPFDSTPSDFDAQFFVE 232  (SEQ ID NO:5)
Laccaria        TDSVISMLARMADAG-FSPAELVALLASHSIANVVDIDPTVAGIPLDSTSTTFDSQLFLE 228  (SEQ ID NO:2)
Phanerochaete   QDSVTKILQRFEDAGGFTPFEVVSLLASHSVARADKYDQTIDAAPFDSTPFTFDTQVFLE 225  (SEQ ID NO:7)
Gelatoporia     QDNVSTILARFADAGNFSPFEVVSLLASHSVARADKNDPTLDAAPFDTTPFTFDTQIPLE 227  (SEQ ID NO:8)
Lentinula       QNTVEILARFQDAANMNAEDIVSLLVSHTVARADHVDPTLDAAPFDSTPFTFDSQFFLE 232  (SEQ ID NO:4)
                    :  **. : .  : **   *: *  :*: :     :     *. * *** . :*

Phlebia         TQLRGILFPGTGGNQGFVESPL-------------HGEIRLQSDSELARDSRTACEWQSFVN 280  (SEQ ID NO:6)
Trametes        TQLRCTLFPGTGGNQGEVESPL-------------RGEIRLQSDSELARDSRTACEWQSPVN 283  (SEQ ID NO:1)
Pleurotus       TQLRCISFPGTGGNHGEVQSPL-------------RGENRLQSDHLFARDDRTSCEWQSMTN 279  (SEQ ID NO:3)
Ganoderma       TMLNCTLVPGNGLQDGEVLSPY-------------PGEFRLQSDFALSRDSRTTCEWQKMIA 281  (SEQ ID NO:5)
Laccaria        VLLKCTVFPGSGANSGEVQSFT-------------TAENRLQSDSAIARDHRTACSWQSMIN 277  (SEQ ID NO:2)
Phanerochaete   VLLKCVGFPGSANNTGEVASPLPLGS---GSDTGENRLQSDFALAHDPRTACIWQGFVN 281  (SEQ ID NO:7)
Gelatoporia     VLLKCVGFPGLDNNTGEVASPLPFGDTSTGGNDTGMNRLQSDFALARDERTACFWQGFVD 287  (SEQ ID NO:8)
Lentinula       TLLTCVGFPGTTNNTGEVSSPLPLTV----GDNVGEIRLRLQSDFELARDSRTACFWQSMIN 288  (SEQ ID NO:4)
                 .*  : **   .  **  . *                 :****  *:**::   ::*: :

Phlebia         NQAKIQSAFKAAFRKMTILGHSESSLIECSEVIQTPP-ALEGNAHLPAGQTMNDIEQACA 339  (SEQ ID NO:6)
Trametes        NQAKLQSAFKAAFRKMTVLGHDESLLIECSELVPTPP-PATSVAHFPAGLSNADVEQACA 342  (SEQ ID NO:1)
Pleurotus       DQQKIQDRFSDTLFKMSMLGQNQDAMIDCSDVIPVPA-ALVTKPHLPAGKSKTDVEQACA 338  (SEQ ID NO:3)
Ganoderma       DRANMLEKFEITMLKMSLLGFDQSALTDCSDVIPTA--GTVQDPFIPAGLTVDDLQPACS 340  (SEQ ID NO:5)
Laccaria        NQARMMTQFKAAMAKLQVLGQDTSKLIDCSDVIPVFK-PFAGPIKYPSSFSQANIEQKCT 336  (SEQ ID NO:2)
Phanerochaete   EQAFMAASFRAAMSKLAVLGHNRNSLIDCSDVVPVPIFATGQPAMFPASTGPQDLELSCP 341  (SEQ ID NO:7)
Gelatoporia     QQDFMAQSFQAAFERMAILGSNAADLINCSAVVPQSVGFVTVPATFPATTGPQDLQLNCT 347  (SEQ ID NO:8)
Lentinula       QEALMASRFKAAMAKMAVIGHNANDLIDCSAVVPKFVPALNKPATFPATKTKADVQQACP 348  (SEQ ID NO:4)
                 :  :  : . : *: : *.   : *.*. ::  .                 :   *

Phlebia         TTPFFSLSADPGP-ATSVAPVPPS---------- 362  (SEQ ID NO:6)
Trametes        DTPFFTLPTDPGP-VTTVAPVPPS---------- 365  (SEQ ID NO:1)
Pleurotus       TGAFPALGADPGP-VTSVPVRPPA---------- 361  (SEQ ID NO:3)
Ganoderma       SSAFPTVTTVAGA-VTSIPAVPLNS--------- 364  (SEQ ID NO:5)
Laccaria        EFKFPSVGR------------------------- 345  (SEQ ID NO:2)
Phanerochaete   SERFFTLTTQPGASQSLIAHCPDGSMSCPGVQFNGPA----- 378  (SEQ ID NO:7)
Gelatoporia     SETFFSLSIDPGATETLIPHCPDGTEDCPSLQFSGPATDSP 388  (SEQ ID NO:8)
Lentinula       -EPFNLTTDRAPRETEIPHCPDNEATCTS----- 377  (SEQ ID NO:4)
                  *: 
```

*FIG. 1B*

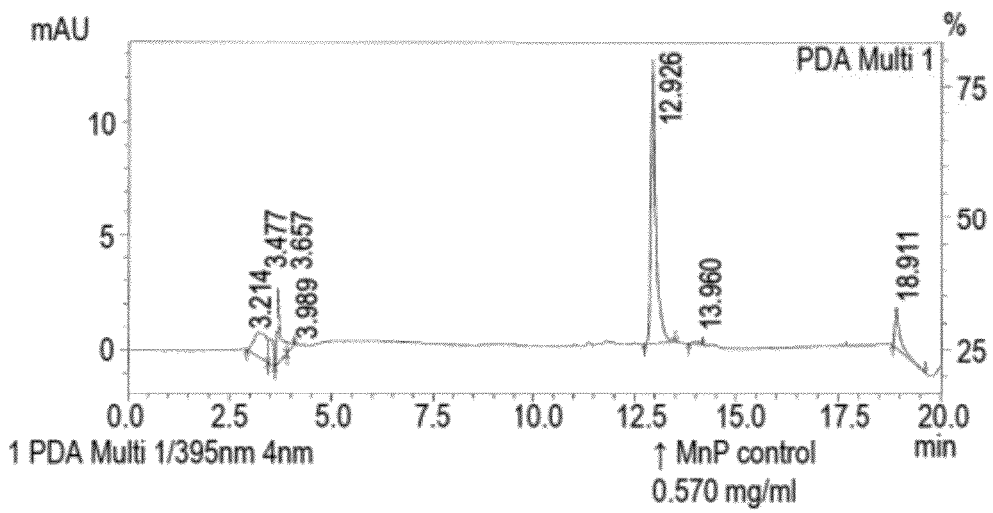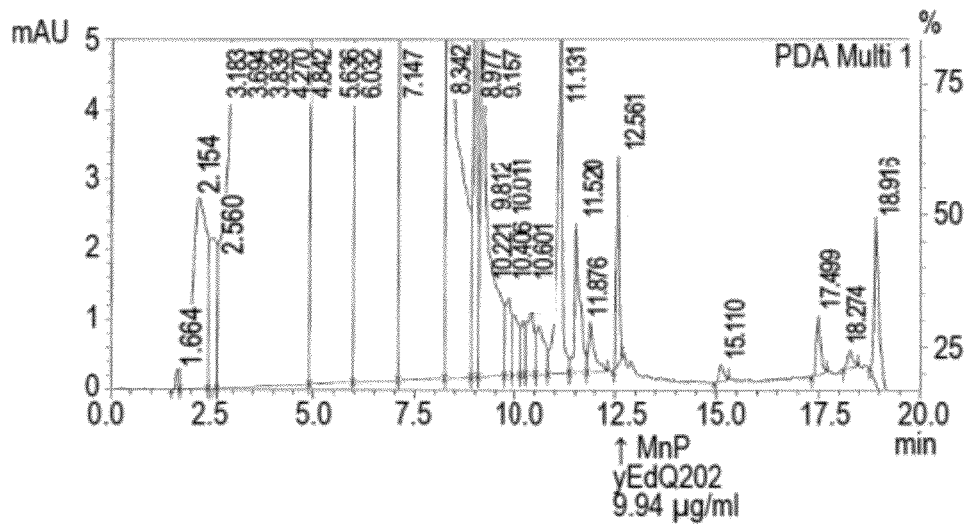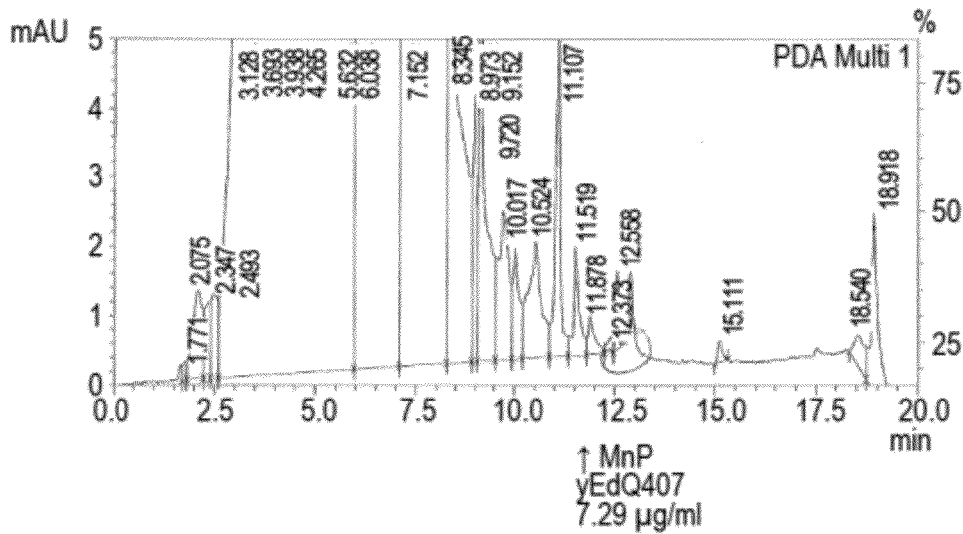
FIG. 14B

USE OF MANGANESE PEROXIDASE FOR ENZYMATIC HYDROLYSIS OF LIGNOCELLULOSIC MATERIAL

CROSS-REFERENCES TO RELATED APPLICATIONS

The present invention claims benefit of priority to U.S. Provisional Patent Application No. 61/413,815, filed Nov. 15, 2010, which is incorporated by reference in its entirety.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 27586-21.TXT, created on Nov. 11, 2011, 102,400 bytes, machine format IBM-PC, MS-Windows operating system, is hereby incorporated by reference in its entirety for all purposes.

BACKGROUND OF THE INVENTION

Lignocellulosic materials contain carbohydrate in the form of complex polymers. The polymers can be broken down to simple sugars which in turn can be used to produce various products including ethanol. Various biomass feedstocks have a lignocellulosic structure where lignin surrounds the hemicelluloses and cellulosic carbohydrates whose release increases upon enzymatic treatment with cellulases. However, enzyme cost and low efficiency of hydrolysis are major issues associated with lignocellulosic materials' potential as a source of fermentable sugars. Enzymatic activities that increase the availability of glucan and xylan carbohydrates through lignin disruption can address both these issues to promote economic viability of cellulosic sugar technology at commercial scale.

BRIEF SUMMARY OF THE INVENTION

Provided herein, inter alia, are improved manganese peroxidases substantially identical (e.g., at least 70%, 75%, 80%, 85%, 90%, 91%, 92%, 93%, 94%, 95%, 96%, 97%, 98%, 99%) to SEQ ID NO:1 and having improved manganese peroxidase activity compared to a control manganese peroxidase comprising SEQ ID NO:1. In some embodiments, the improved manganese peroxidases are substantially identical (e.g., at least 70%, 75%, 80%, 85%, 90%, 91%, 92%, 93%, 94%, 95%, 96%, 97%, 98%, 99%) to SEQ ID NO:2 and have improved manganese peroxidase activity compared to a control manganese peroxidase comprising SEQ ID NO:2. In some embodiments, the improved manganese peroxidases are substantially identical (e.g., at least 70%, 75%, 80%, 85%, 90%, 91%, 92%, 93%, 94%, 95%, 96%, 97%, 98%, 99%) to SEQ ID NO:3 and have improved manganese peroxidase activity compared to a control manganese peroxidase comprising SEQ ID NO:3. In some embodiments, the improved manganese peroxidases are substantially identical (e.g., at least 70%, 75%, 80%, 85%, 90%, 91%, 92%, 93%, 94%, 95%, 96%, 97%, 98%, 99%) to SEQ ID NO:4 and have improved manganese peroxidase activity compared to a control manganese peroxidase comprising SEQ ID NO:4. In some embodiments, the improved manganese peroxidases are substantially identical (e.g., at least 70%, 75%, 80%, 85%, 90%, 91%, 92%, 93%, 94%, 95%, 96%, 97%, 98%, 99%) to SEQ ID NO:5 and have improved manganese peroxidase activity compared to a control manganese peroxidase comprising SEQ ID NO:5. In some embodiments, the improved manganese peroxidases are substantially identical (e.g., at least 70%, 75%, 80%, 85%, 90%, 91%, 92%, 93%, 94%, 95%, 96%, 97%, 98%, 99%) to SEQ ID NO:6 and have improved manganese peroxidase activity compared to a control manganese peroxidase comprising SEQ ID NO:6. In some embodiments, the improved manganese peroxidases are substantially identical (e.g., at least 70%, 75%, 80%, 85%, 90%, 91%, 92%, 93%, 94%, 95%, 96%, 97%, 98%, 99%) to SEQ ID NO:7 and have improved manganese peroxidase activity compared to a control manganese peroxidase comprising SEQ ID NO:7. In some embodiments, the improved manganese peroxidases are substantially identical (e.g., at least 70%, 75%, 80%, 85%, 90%, 91%, 92%, 93%, 94%, 95%, 96%, 97%, 98%, 99%) to SEQ ID NO:8 and have improved manganese peroxidase activity compared to a control manganese peroxidase comprising SEQ ID NO:8.

In some embodiments, the improved manganese peroxidases comprise one or more mutations at a position corresponding to a position selected from the group consisting of (a) position 17 of SEQ ID NO:1, having an amino acid other than Q; (b) position 57 of SEQ ID NO:1 having an amino acid other than D; (c) position 80 of SEQ ID NO:1 having an amino acid other than S; (d) position 107 of SEQ ID NO:1 having an amino acid other than N; (e) position 109 of SEQ ID NO:1 having an amino acid other than H; (f) position 111 of SEQ ID NO:1 having an amino acid other than N; (g) position 152 of SEQ ID NO:1 having an amino acid other than Q; (h) position 278 of SEQ ID NO:1 having an amino acid other than W; and (i) position 204 of SEQ ID NO:1 having an amino acid other than T.

In another aspect, provided herein are polynucleotides comprising a nucleic acid encoding the improved manganese peroxidases provided herein. In some embodiments, the polynucleotide comprises an expression cassette comprising a heterologous promoter operably linked to the nucleic acid. Also provided herein are vectors comprising the polynucleotides provided herein, and isolated cells or culture of cells comprising the polynucleotides that is heterologous to the cell. In some embodiments, the cell is a yeast cell. In some embodiments, the cell is a *Saccharomyces cerevisiae*.

In another aspect, provided herein are methods for converting a cellulose-containing biomass feedstock to a sugar or a non-sugar biomass-derived intermediate. In some embodiments, the methods comprise treating the biomass with an improved manganese peroxidase as described herein (e.g., comprising one or more mutations at a position corresponding to a position selected from the group consisting of (a) position 17 of SEQ ID NO:1 having an amino acid other than Q; (b) position 57 of SEQ ID NO:1 having an amino acid other than D; (c) position 80 of SEQ ID NO:1 having an amino acid other than S; (d) position 107 of SEQ ID NO:1 having an amino acid other than N; (e) position 109 of SEQ ID NO:1 having an amino acid other than H; (f) position 111 of SEQ ID NO:1 having an amino acid other than N; (g) position 152 of SEQ ID NO:1 having an amino acid other than Q; (h) position 278 of SEQ ID NO:1 having an amino acid other than W; and (i) position 204 of SEQ ID NO:1 having an amino acid other than T.

In some embodiments, the cellulose-containing biomass feedstock is converted into sugar. In some embodiments, the method further comprises fermenting the sugar to ethanol.

In some embodiments, the cellulose-containing biomass feedstock is converted into a sugar biomass-derived intermediate.

In some embodiments, the cellulose-containing biomass feedstock is converted into a non-sugar biomass-derived intermediate.

In some embodiments, the method comprises treating the biomass with a cell or culture of cells that express the improved manganese peroxidase. In some embodiments, the cell is a *Saccharomyces cerevisiae*.

In some embodiments, the cellulose-containing biomass feedstock is a woody material. In some embodiments, the woody material is cellulosic or lignocellulosic plant material selected from the group consisting of orchard prunings, chaparral, mill waste, urban wood waste, municipal waste, logging waste, forest thinnings, short-rotation woody crops, and industrial waste. In some embodiments, the cellulose-containing biomass feedstock is a non-woody material. In some embodiments, the non-woody material is selected from the group consisting of gramineous agricultural residue, wheat straw, oat straw, rice straw, barley straw, rye straw, flax straw, sugar cane, corn stover, corn stalks, corn cobs, corn husks, prairie grass, switchgrass, gamagrass, foxtail, sugar beet pulp, citrus fruit pulp, seed hulls, cellulosic animal wastes, lawn clippings, seaweed, bagasse, energy cane, and giant reed. In some embodiments, the cellulose-containing biomass feedstock is corn grain, barley grain, milo grain, wheat grain or rice grain.

BRIEF DESCRIPTION OF THE DRAWINGS

FIG. 1 depicts an amino acid sequence alignment of exemplary manganese peroxidases from various species of fungus: *Trametes versicolor* (SEQ ID NO:1), *Laccaria bicolor* S238N-H82 (SEQ ID NO:2), *Pleurotus ostreatus* (SEQ ID NO:3), *Lentinula edodes* (SEQ ID NO:4), *Ganoderma applanatum* (SEQ ID NO:5), *Phlebia radiata* (SEQ ID NO:6), *Phanerochaete chrysosporium* (SEQ ID NO:7), *Gelatoporia subvermispora* (SEQ ID NO:8). "*" indicates an identical amino acid residue in all sequences.

FIG. 14B. MnP expression quantitated by Reverse Phase-HPLC. Samples analyzed by RP-HPLC of control MnP (Jena Bio Sciences; top panel), *S. cerevisiae* secreted wild type MnP from yEdQ202 (middle panel), *S. cerevisiae* secreted mutant MnP from yEdQ407 (bottom panel). MnP is noted with arrow below chromatogram.

FIG. 18 depicts inhibitor levels at 48 hours fermentation tracked by HPLC in corn stover fermentation experiment shown in FIG. 15. Inhibitors associated with biomass pretreated material were measured by HPLC.

FIG. 21 depicts inhibitors and phenolic compounds commonly associated with biomass pretreated material and measured by HPLC; experiment shown in FIG. 19.

DEFINITIONS

Figure 2:
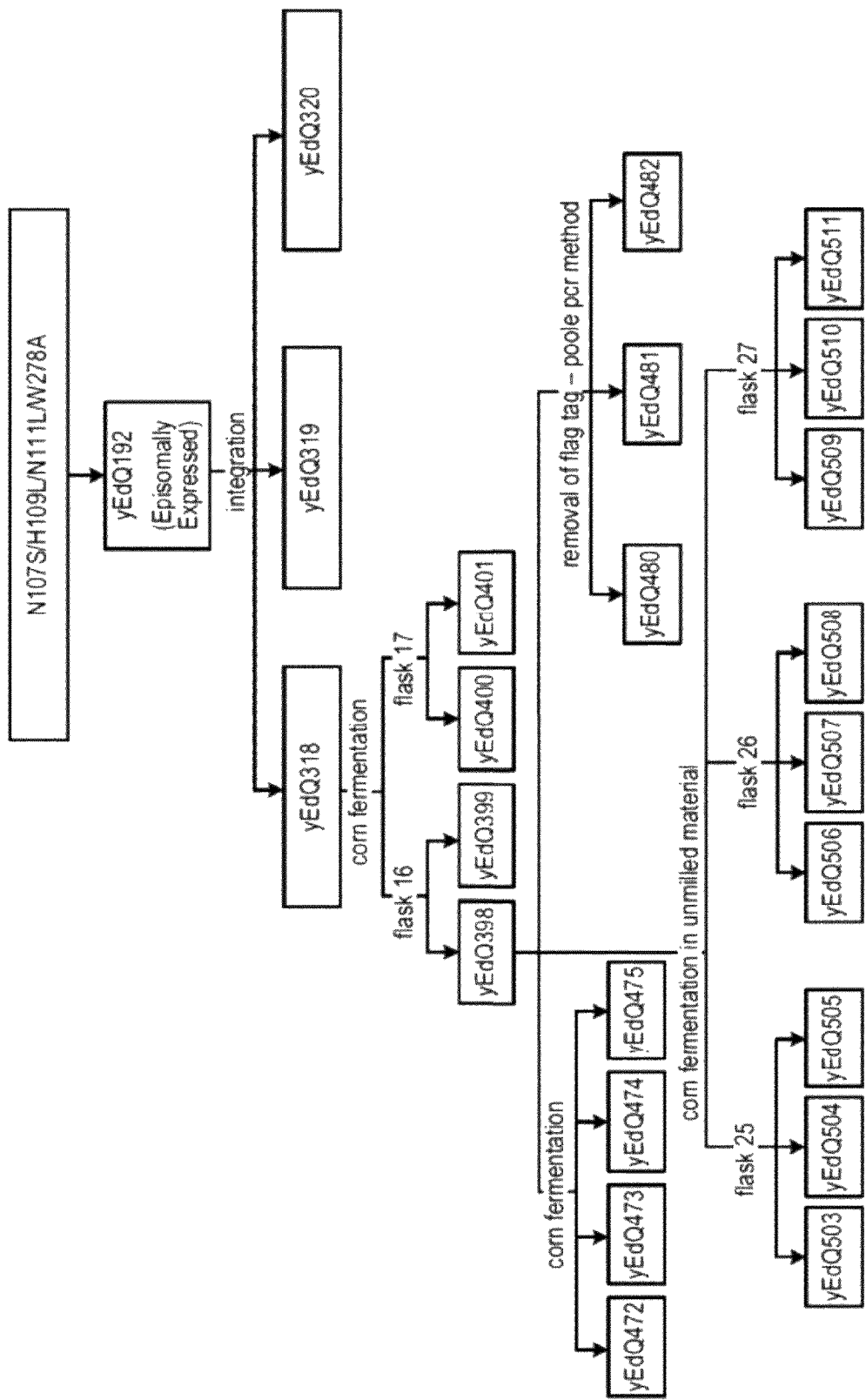
FIG. 2 depicts evolutionary diagram for mutant yEdQ318. Mutation N107S/H109L/N111L/W278A was generated using a site directed mutagenesis kit from Stratagene. The plasmid with the mutation was initially incorporated into bacteria. After sequence was confirmed, the plasmid was transformed into yeast and designated yEdQ192. Next, the mutation was integrated into the yeast genome and three colonies from that transformation were kept; yEdQ318, yEdQ319, and yEdQ320. Randomly, yEdQ318 was chosen to be tested in corn. This corn fermentation was performed in triplicate. Two flasks labeled flask 16 and 17 were used to obtain adapted yEdQ318. Adaptation is defined as exposing the yeast to a specific environment and allowing it to react (ferment) accordingly. A sample of the corn mash after fermentation was obtained and streaked onto media plate for growth. Two colonies from each flask were picked and kept; yEdQ398 through yEdQ401. Additional corn fermentation experiments were conducted with yEdQ398 and additional adapted strains were collected. Later, corn mash from unmilled material was used for adaptation versus the milled material used in prior experiments and these are labeled yEdQ503 through yEdQ511. Lastly, genomic sequence of yEdQ398 was used for flag tag removal. Flag tag removal was done via polymerase chain reaction (PCR). The sequence from PCR was incorporated into an in-house vector. Instead of finding a single colony that transformed the sequence correctly, many colonies were pooled together, and desired sequence was amplified. The amplified product was then integrated into the yeast genome giving rise to yEdQ480 through yEdQ482.

Unless defined otherwise, all technical and scientific terms used herein have the same meaning as commonly understood by one of ordinary skill in the art to which this invention pertains. Although essentially any methods and materials similar to those described herein can be used in the practice or testing of the present invention, only exemplary methods and materials are described. For purposes of the present invention, the following terms are defined below.

The terms "a," "an," and "the" include plural referents, unless the context clearly indicates otherwise.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrrolysine and selenocysteine.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, *Proteins* (1984)).

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (e.g., a polypeptide of the invention), which does not comprise additions or deletions, for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same. The term "substantially identical" refers to two or more sequences or subsequences that have a specified percentage of amino acid residues or nucleotides that are the same (i.e., at least about 40% identity, 45%, 50%, 55%, 60%, 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see e.g., NCBI web site http://www.ncbi.nlm.nih.gov/BLAST/ or the like). The present invention provides for, e.g., polypeptide sequences (e.g., improved manganese peroxidases) that are substantially identical to a reference sequence, e.g., SEQ ID NOS:1-20, as well as nucleic acids encoding such polypeptides. The definition includes sequences that have deletions and/or additions, as well as those that have substitutions. As described below, algorithms can account for gaps and the like. When not specified, identity or substantial identity is determined over the entire length of the reference sequence. When specified, identity can be determined over a region that is at least about 10 amino acids or nucleotides in length, at least about 25 amino acids or nucleotides in length, or over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

An exemplary algorithm suitable for determining percent sequence identity and sequence similarity is BLAST 2.0 algorithm, which is described in Altschul et al. (1990) *J. Mol. Biol.* 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

To determine which amino acid of a first protein "corresponds" to the position of an amino acid in a second protein, the amino acid sequences of the two proteins are optimally aligned (e.g., using a BLAST algorithm). This is particularly useful, for example, where two proteins have high homology but where one protein contains one or more insertions or deletions relative to the second protein. In such cases, for example, position 57 of a first protein may align with position 51 in a second protein when the two proteins are optimally aligned. Thus position 51 of the second protein "corresponds" to position 57 of the first protein.

A "heterologous sequence," "heterologous polypeptide," or a "heterologous nucleic acid", as used herein, is one that originates from a source foreign to the particular host cell, or, if from the same source, is modified from its original form. Thus, a heterologous expression cassette in a cell is an expression cassette that is not endogenous to the particular host cell, for example by being linked to nucleotide sequences from an expression vector rather than chromosomal DNA or by being linked to a heterologous promoter or by being linked to a reporter gene, etc.

"Expression cassette" refers to a polynucleotide comprising a promoter or other regulatory sequence operably linked to a sequence encoding a protein.

The term "improved manganese peroxidase activity," or "improved MnP activity," as used herein, means a variant manganese peroxidase displaying an increase, relative to a reference sequence (e.g., a control sequence or an unmodified form of manganese peroxidase as described herein), in the amount of substrate hydrolysis that occurs in a specified time under specified reaction conditions. In some embodiments, the variant manganese peroxidase can display an increase of, relative to a reference sequence, at least 5%, 10%, 20%, 30%, 40%, 50%, 100%, 200%, or more, in the amount of substrate hydrolysis that occurs in a specified time under specified reaction conditions. In some embodiments, the reference sequence has a sequence that is the same as the variant manganese peroxidase sequence except for positions with modifications. Manganese peroxidase activity can be measured using a variety of methods known in the art, such as the 3-methyl-2-benzothiazolinone hydrazone/3-(dimethylamino)benzoic acid (MBTH/DMAB) assay described hereinbelow or in Castillo et al., Analytical Biochemistry, 218: 399-404, 1994. To compare manganese peroxidase activity of two recombinantly expressed proteins, the specific activity (activity per mole enzyme or activity per gram enzyme) can be compared. Alternatively, cells expressing and secreting the recombinant proteins can be cultured under the same conditions and the manganese peroxidase activity per volume culture medium can be compared.

The term "cellulose-containing biomass feedstock" is defined herein to mean any cellulosic or lignocellulosic plant material, waste material, including but not limited to, leaves and stalks of both woody and non-woody plants. The term "woody" is used herein both in the botanical sense to mean "comprising wood"; that is, composed of extensive xylem tissue as found in trees and shrubs, and also in the sense of "being woodlike". Accordingly, "nonwoody" refers to materials lacking these characteristics. Cellulose-containing biomass feedstock includes, but is not limited to, crops such as starch crops (e.g., corn, wheat, rice or barley), sugar crops (e.g., sugarcane, energy cane or sugarbeet), forage crops (e.g., grasses, alfalfa, or clover), and oilseed crops (e.g., soybean, sunflower, or safflower); wood products such as trees, shrubs, and wood residues (e.g., sawdust, bark or the like from forest clearings and mills); waste products such as municipal solid waste (MSW; e.g., paper, food and yard wastes or wood), and process waste; and aquatic plants such as algae, water weed, water hyacinth, or reed and rushes.

In some embodiments, cellulose-containing biomass feedstock from woody plants can include orchard prunings, chaparral, mill waste (such as bark, chips, shavings, sawdust, and the like), urban wood waste (such as discarded lumber, wood pallets, crates, tree and brush trimmings, etc.), municipal waste (such as newspaper and discarded grocery produce), logging waste and forest thinnings (tree tops, limbs and cull material), short-rotation woody crops such as poplar and cottonwood, and industrial waste (such as wood pulp sludge).

The preponderance of biomass from non-woody plants in agriculture is derived from monocotyledonous plants, and especially grassy species belonging to the family Gramineae. Of primary interest are gramineous agricultural residues; that is, the portion of grain-bearing plants that remain after harvesting the seed. Illustrative of such residues, without limitation thereto, are wheat straw, oat straw, rice straw, barley straw, rye straw, flax straw, sugar cane, corn stover, corn stalks, corn cobs, corn husks, and the like. Also included within this definition are grasses not conventionally cultivated for agricultural purposes, such as prairie grasses (e.g. big bluestem, little bluestem, Indian grass), switchgrass, gamagrass, and foxtail. In some embodiments, the agricultural biomass comprises corn kernel, barley kernel, milo kernel, wheat kernel or rice kernel.

Byproducts of agriculture industrial process can have high amounts of furfural and 5-HMF. For example, corncobs are used to produce xylose and furfural in certain countries, including China. For economic reasons, corncobs are treated by acid hydrolysis with byproduct residues from such production considered waste product inasmuch as inhibitors such as furfural are present. Such waste processing residues are usually burned. However, a significant amount of cellulose exists in the corncob residues that can be used to convert into ethanol.

Other agricultural byproducts in the category of biomass include waste streams components from commercial processing of crop materials (such as sugar beet pulp, citrus fruit pulp, sugarcane bagasse, seed hulls, and the like), cellulosic animal wastes, lawn clippings, seaweed, etc. In some embodiments, the biomass is distillers grains.

Any of the aforementioned biomass materials would be utilized as substrates for fermentative conversion to ethanol.

DETAILED DESCRIPTION OF THE INVENTION

I. Introduction

The present invention provides for improved manganese peroxidases having improved MnP activity. Manganese peroxidase (Mnp) is one of four principal ligninolytic enzymes involved in lignin degradation commonly employed by certain fungi. Lignin is the second most abundant organic carbon compound on earth. It is a complex heterogeneous structure consisting of guaiacyl, syringyl, and p-hydroxyphenol subunits. Oxidative coupling of these lignin aromatic alcohol monomers creates the complex structure of lignin, which is highly recalcitrant to degradation (M. Dashtban et al., 2010). Subunit ratios and lignin composition vary among different plants. MnP is a hemoprotein that disrupts lignin structure through creation of reactive radical species. The enzymatic activity of MnP catalyzes the oxidation of Mn(II) to Mn(III) by $H_2O_2$ (M. Sundaramoorthy et al., 2005). Delignification is important for the bioconversion of lignoncellulosic biomass to ethanol as this process liberates and makes more accessible cellulose and hemicellulose. Depolymerization of these carbohydrates produces sugars that can be taken up by *Saccharomyces cerevisiae* for the production of ethanol. The Mnp gene expressed in strains described herein is taken from *Trametes versicolor*, a polypore mushroom with ubiquitous distribution worldwide.

A number of mutations in fungal manganese peroxidases have been discovered that improve manganese peroxidase activity. In view of the conserved sequences of other manganese peroxidases (see e.g., FIG. 1), it is believed that corresponding mutations can also be introduced into other manganese peroxidases. The improved manganese peroxidases can be used in any reaction where lignin or cellulose degradation is desired. For example, these improved manganese peroxidases can be used as enzyme additives in biomass fermentation to convert biomass to ethanol. Further, these improved manganese peroxidases can be expressed in yeast cells or other cells. This allows for lignocellulosic material-to-ethanol production in one reaction.

In some embodiments, the improved manganese peroxidases described herein increase the amount of substrate hydrolysis relative to a control or reference manganese peroxidase in a specified time under specified conditions. An increase in the amount of substrate hydrolysis can be determined, for example, by measuring the amount of carbohydrates liberated or produced by the improved manganese peroxidase as compared to the amount of carbohydrates produced by a reference manganese peroxidase under specified conditions. In some embodiments, the substrate is a lignocellulosic material. In certain embodiments, the substrate is lignin. In some embodiments, the carbohydrates measured are polysaccharides from cellulose and/or hemicellulose. In some embodiments, the carbohydrates measured are fermentable sugars. In some embodiments, the conditions are those specified in the examples.

In some embodiments, an increase in the amount of substrate hydrolysis can be determined by measuring the amount of downstream products produced from biomass hydrolysis under specified conditions. For example, in some embodiments, the downstream product is a carbohydrate such as glucan, xylan, or a fermentable sugar. In some embodiments, the downstream product is a sugar biomass-derived intermediate. In some embodiments, the downstream product is a non-sugar biomass-derived intermediate. In some embodiments, the downstream product is an inhibitor of fermentation, such as a phenolic compound. In some embodiments, the conditions are those specified in the examples.

II. Improved Manganese Peroxidases

The improved or unmodified manganese peroxidases and MnP control preparations provided herein can be of any origin, e.g., they can be from bacteria, yeast, fungus, plant, insect, or mammalian manganese peroxidases. In some embodiments, the manganese peroxidases are fungal manganese peroxidases. In some embodiments, the manganese peroxidases are manganese peroxidase variants having at least 70%, 75%, 80%, 85%, 90%, 91%, 92%, 93%, 94%, 95%, 96%, 97%, 98%, 99%, or higher sequence identity to a fungal manganese peroxidase, e.g., a manganese peroxidase of SEQ ID NOS:1-8 (e.g., SEQ ID NOS:1, 2, 3, 4, 5, 6, 7 or 8) and in some embodiments contain one or more of the mutations described herein.

In some embodiments, unmodified forms of manganese peroxidase amenable to mutation in accordance with the present invention are those having an active site domain comprising the following amino acid motif ("Motif A"):

```
X_{a1}-X_{a2}-X_{a3}-X_{a4}-Cys-Gly-X_{a5}-X_{a6}-X_{a7}-His-X_{a8}-X_{a9}-X_{a10}-Arg-Leu-

X_{a11}-Phe-His-Asp-Ala-Ile (also referred to herein in the one-letter code as X_{a1}-X_{a2}-X_{a3}-X_{a4}-C-G-X_{a5}-X_{a6}-X_{a7}-H-X_{a8}-X_{a9}-

X_{a10}-R-L-X_{a11}-F-H-D-A-I (SEQ ID NO: 9));
wherein

X_{a1} is Asp (D), His (H), Gly (G), Gln (Q), or Glu (E);

X_{a2} is Gly (G), Asp (D), or Asn (N);

X_{a3} is Gly (G) or absent;

X_{a4} is Glu (E), Ala (A), or Gln (Q);
```

$X_{a5}$ is Glu (E) or Phe (F);

$X_{a6}$ is Glu (E), Asp (D), Gly (G) or Thr (T);

$X_{a7}$ is Val (V) or Ala (A);

$X_{a8}$ is Glu (E) or Thr (T);

$X_{a9}$ is Ser (S), Ala (A), Val (V), or Ile (I);

$X_{a10}$ is Leu (L) or Ile (I);
and $X_{a11}$ is Thr (T) or Ser (S).

In some embodiments, unmodified forms of manganese peroxidase amenable to mutation in accordance with the present invention are those having an active site domain comprising the following amino acid motif ("Motif B"):

Gly-Ala-Asp-Gly-Ser-$X_{b1}$-$X_{b2}$-$X_{b3}$-$X_{b4}$-$X_{b5}$-$X_{b6}$-$X_{b7}$-Glu-$X_{b8}$-$X_{b9}$-$X_{b10}$-$X_{b11}$-$X_{b12}$-$X_{b13}$-$X_{b14}$-Gly (also referred to herein in the one-letter code as G-A-D-G-S-$X_{b1}$-$X_{b2}$-$X_{b3}$-$X_{b4}$-$X_{b5}$-$X_{b6}$-$X_{b7}$-E-$X_{b8}$-$X_{b9}$-$X_{b10}$-$X_{b11}$-$X_{b12}$-$X_{b13}$-$X_{b14}$-G (SEQ ID NO: 10));
wherein $X_{b1}$ is Ile (I), Val (V), or Met (M);

$X_{b2}$ is Ala (A), Ile (I), or Leu (L);

$X_{b3}$ is Ile (I), Leu (L), Thr (T), or Ala (A);

$X_{b4}$ is Phe (F) or His (H);

$X_{b5}$ is Ala (A), Glu (E), Ser (S), Asn (N), or Pro (P);

$X_{b6}$ is Glu (E), Asp (D), Thr (T), or Leu (L);

$X_{b7}$ is Ile (I), Thr (T), or Val (V);

$X_{b8}$ is Thr (T), Val (V), Leu (L), or Pro (P);

$X_{b9}$ is Asn (N), Thr (T), Ala (A), or Glu (E);

$X_{b10}$ is Phe (F) or Tyr (Y);

$X_{b11}$ is His (H), Pro (P), Asp (D), Ser (S), Gln (Q), or Ala (A);

$X_{b12}$ is Ala (A) or Val (V);

$X_{b13}$ is Asn (N) or Ser (S);
and $X_{b14}$ is Asn (N), Leu (L), Asp (D), or Val (V).

In some embodiments, unmodified forms of manganese peroxidase amenable to mutation in accordance with the present invention are those having a domain comprising the following amino acid motif ("Motif C"):

$X_{c1}$-$X_{c2}$-$X_{c3}$-$X_{c4}$-$X_{c5}$-$X_{c6}$-$X_{c7}$-$X_{c8}$-Cys-$X_{c9}$-Gly-$X_{c10}$-Pro-$X_{c11}$-$X_{c12}$-$X_{c13}$-$X_{c14}$-$X_{c15}$-$X_{c16}$-Gly-Arg (also referred to herein in the one-letter code as $X_{c1}$-$X_{c2}$-$X_{c3}$-$X_{c4}$-$X_{c5}$-$X_{c6}$-$X_{c7}$-$X_{c8}$-C-$X_{c9}$-G-$X_{c10}$-P-$X_{c11}$-$X_{c12}$-$X_{c13}$-$X_{c14}$-$X_{c15}$-$X_{c16}$-G-R (SEQ ID NO: 11));
wherein $X_{c1}$ is Ala (A) or Gly (G);

$X_{c2}$ is Gly (G) or Ala (A);

$X_{c3}$ is Ala (A) or Thr (T);

$X_{c4}$ is Val (V), Ile (I), Leu (L);

$X_{c5}$ is Gly (G) or Ala (A);

$X_{c6}$ is Val (V), Thr (T), or Leu (L);

$X_{c7}$ is Ser (S), Thr (T), Ala (A), or Gly (G);

$X_{c8}$ is Asn (N) or Leu (L);

$X_{c9}$ is Pro (P) or Asn (N);

$X_{c10}$ is Ala (A) or Gly (G);

$X_{c11}$ is Ala (A), Gln (Q), or Arg (R);

$X_{c12}$ is Leu (L) or absent;

$X_{c13}$ is Pro (P), Asp (D). Ser (S), Gln (Q), or Glu (E);

$X_{c14}$ is Val (V), Phe (F), Tyr (Y), or Leu (L);

$X_{c15}$ is Phe (F), Met (M), Leu (L), or Arg (R);
and $X_{c16}$ is Val (V), Ile (I), Leu (L), Ala (A), or Phe (F).

In some embodiments, unmodified forms of manganese peroxidase amenable to mutation in accordance with the present invention are those having an active site domain comprising the following amino acid motif ("Motif D"):

Leu-Leu-$X_{d1}$-$X_{d2}$-His-$X_{d3}$-$X_{d4}$-$X_{d5}$-$X_{d6}$-$X_{d7}$-$X_{d8}$-$X_{d9}$-$X_{d10}$-Asp-$X_{d11}$-$X_{d12}$-$X_{d13}$-$X_{d14}$-$X_{d15}$-$X_{d16}$-Pro (also referred to herein in the one-letter code as L-L-$X_{d1}$-$X_{d2}$-H-$X_{d3}$-$X_{d4}$-$X_{d5}$-$X_{d6}$-$X_{d7}$-$X_{d8}$-$X_{d9}$-$X_{d10}$-D-$X_{d11}$-$X_{d12}$-$X_{d13}$-$X_{d14}$-$X_{d15}$-$X_{d16}$-P (SEQ ID NO: 12));
wherein $X_{d1}$ is Ala (A), Val (V), or Ser (S);

$X_{d2}$ is Ser (S) or Ala (A);

$X_{d3}$ is Ser (S) or Thr (T);

$X_{d4}$ is Ile (I) or Val (V);

$X_{d5}$ is Ala (A) or Gly (G);

$X_{d6}$ is Ala (A), Ser (S), Asn (N), or Arg (R);

$X_{d7}$ is Ala (A), Gln (Q), or Val (V);

$X_{d8}$ is Asp (D), Asn (N), or Val (V);

$X_{d9}$ is His (H), Thr (T), Asp (D), or Lys (K);

$X_{d10}$ is Val (V) or Ile (I);

$X_{d11}$ is Pro (P). Glu (E), Ser (S), or Gln (Q);

$X_{d12}$ is Ser (S) or Thr (T);

$X_{d13}$ is Ile (I), Val (V), or Leu (L);

$X_{d14}$ is Pro (P), Ala (A), or Asp (D);

$X_{d15}$ is Gly (G) or Ala (A);
and $X_{d16}$ is Thr (T), Ala (A), or Ile (I).

In some embodiments, unmodified forms of manganese peroxidase amenable to mutation in accordance with the present invention are those having an active site domain comprising the following amino acid motif ("Motif E"):

Arg-Leu-Gln-Ser-Asp-$X_{e1}$-$X_{e2}$-$X_{e3}$-$X_{e4}$-$X_{e5}$-Asp-$X_{e6}$-Arg-Thr-$X_{e7}$-Cys-$X_{e8}$- $X_{e9}$-Gln-$X_{e10}$-$X_{e11}$ (also referred to herein in the one-letter code as R-L-Q-S-D-$X_{e1}$-$X_{e2}$-$X_{e3}$-$X_{e4}$-$X_{e5}$-D-$X_{e6}$-R-T-$X_{e7}$-C-$X_{e8}$-$X_{e9}$-Q-$X_{e10}$-$X_{e11}$ (SEQ ID NO: 13));
wherein $X_{e1}$ is Ser (S), His (H), or Phe (F);

$X_{e2}$ is Glu (E), Leu (L), or Ala (A);

$X_{e3}$ is Leu (L) or Phe (F);

$X_{e4}$ is Ala (A) or Ser (S);

-continued $X_{e5}$ is Arg (R) or His (H);

$X_{e6}$ is Ser (S), Asp (D), His (H), Pro (P), or Glu (E);

$X_{e7}$ is Ala (A), Ser (S), or Thr (T);

$X_{e8}$ is Glu (E), Ser (S). Ile (I), or Phe (F);

$X_{e9}$ is Trp (W);

$X_{e10}$ is Ser (S), Lys (K), or Gly (G); and $X_{e11}$ is Phe (F) or Met (M).

These motifs ("Motifs A-E") are present within the active site domain, manganese binding site domain, or otherwise conserved domain of many fungal manganese peroxidases. FIG. 1 shows an amino acid sequence alignment of manganese peroxidases from several species of fungus. As shown, these motifs ("Motifs A-E") are present in each of these manganese peroxidases, indicating a conserved function for these regions of the fungal manganese peroxidases. The structure and function of manganese peroxidase is described, for example, in Sunaramoorthy et al. (Sunaramoorthy, M., Kishi, K., Gold, M. H. and T. L. Pouls. 1994. The Crystal Structure of Manganese Peroxidase from *Phanerochaete chrysosporium* at 2.06 A Resolution. *J. Biol. Chem.* Vol. 269 No. 52: pp. 32759-32767) and Ruis-Duenas et al (Ruis-Duenas, F. J. and A. T. Martinez. 2009. Microbial degradation of lignin: how a bulky recalcitrant polymer is efficiently recycled in nature and how we can take advantage of this. *Microbial Biotechnology* Vol 2 No. 2: pp. 164-177).

Accordingly, in some embodiments, the unmodified form of the manganese peroxidase is a wild-type or a naturally occurring manganese peroxidase, such as, for example, a fungus manganese peroxidase. The full nucleic acid and amino acid sequence for numerous fungal manganese peroxidases are available. The amino acid sequences of *Trametes versicolor* (SEQ ID NO:1), *Laccaria bicolor* S238N-H82 (SEQ ID NO:2), *Pleurotus ostreatus* (SEQ ID NO:3), *Lentinula edodes* (SEQ ID NO:4), *Ganoderma applanatum* (SEQ ID NO:5), *Phlebia radiata* (SEQ ID NO:6), *Phanerochaete chrysosporium* (SEQ ID NO:7), *Gelatoporia subvermispora* (SEQ ID NO:8) are shown in FIG. 1. Additional fungal manganese peroxidases are known in the art, including *Ganoderma austral* (SEQ ID NO:21), *Ganoderma formosanum* (SEQ ID NO:22), *Phanerochaete sordida* (SEQ ID NO:23), *Agaricus bisporus* (SEQ ID NO:24), *Phlebia* sp. MG60 manganese peroxidase 1 (SEQ ID NO:25), *Phlebia* sp. MG60 manganese peroxidase 2 (SEQ ID NO:26), *Pleurotus* sp. 'Florida' (SEQ ID NO:27), *Fomitiporia mediterranea* manganese peroxidase 1 (SEQ ID NO:28), *Fomitiporia mediterranea* manganese peroxidase 2 (SEQ ID NO:29), *Fomitiporia mediterranea* manganese peroxidase 3 (SEQ ID NO:30), *Dichomitus squalens* manganese peroxidase 1 (SEQ ID NO:31), *Dichomitus squalens* manganese peroxidase 2 (SEQ ID NO:32), *Ceriporiopsis rivulosa* manganese peroxidase 1 (SEQ ID NO:33), *Ceriporiopsis rivulosa* manganese peroxidase 2 (SEQ ID NO:34), *Spongipellis* sp. FERM P-18171 (SEQ ID NO:35), *Phlebia radiata* (SEQ ID NO:36), and *Gelatoporia subvermispora* (SEQ ID NO:37).

Also amenable to the mutations described herein are functional manganese peroxidases that have been previously modified (e.g., by amino acid substitution, addition, or deletion), provided that the previously modified manganese peroxidases retains one or more of the amino acid motifs of SEQ ID NOS:9, 10, 11, 12, and 13. Thus, suitable unmodified manganese peroxidases also include functional variants of wild-type or naturally occurring manganese peroxidases. Such variants typically will have substantial sequence identity or similarity to the wild-type or naturally occurring manganese peroxidases, typically at least 80% sequence identity and more typically at least 90%, 91%, 92%, 93%, 94%, 95%, 96%, 97%, 98% or 99% sequence identity. In some embodiments, such variants have at least 80% sequence identity and more typically at least 90%, 91%, 92%, 93%, 94%, 95%, 96%, 97%, 98% or 99% sequence identity to SEQ ID NOS:1, 2, 3, 4, 5, 6, 7, or 8.

The improved manganese peroxidases provided herein comprise one or more amino acid substitutions relative to the unmodified manganese peroxidase. In some embodiments, the amino acid substitution(s) comprise at least an amino acid substitution at position $X_{a1}$ of the motif set forth in SEQ ID NO:9. Amino acid substitution at this position confers improved manganese peroxidase activity, yielding a mutant manganese peroxidase with an improved manganese peroxidase activity relative to the unmodified manganese peroxidase. In some embodiments, the amino acid at position $X_{a1}$ is substituted with an amino acid that does not correspond to the respective motif as set forth in SEQ ID NO:9. Thus, in some embodiments, the amino acid at position $X_{a1}$, if substituted, is not D, H, G, Q or E. In some embodiments, amino acid substitutions at position $X_{a1}$ include A, R, N, C, I, L, K, M, F, P, S, T, W, Y, or V. In certain embodiments, amino acid substitutions include Arginine (R) or Lysine (K) at position $X_{a1}$. In certain embodiments, amino acid substitutions include Lysine (K) at position $X_{a1}$.

In some embodiments, the improved manganese peroxidase is a mutant manganese peroxidase comprising a sequence substantially identical (e.g., at least 40%, 45%, 50%, 55%, 60%, 65%, 70%, 75%, 80%, 85%, 90%, 91%, 92%, 93%, 94%, 95%, 96%, 97%, 98%, 99% sequence identity) to any of SEQ ID NOS:1, 2, 3, 4, 5, 6, 7, or 8 and having improved manganese peroxidase activity compared with a control manganese peroxidase (e.g., a manganese peroxidase comprising any of SEQ ID NOS:1, 2, 3, 4, 5, 6, 7, or 8), wherein the amino acid of the mutant manganese peroxidase corresponding to position $X_{a1}$, if substituted, is not D, H, G, Q or E. In some embodiments, the amino acid of the mutant manganese peroxidase corresponding to position $X_{a1}$ include A, R, N, C, I, L, K, M, F, P, S, T, W, Y, or V. In certain embodiments, the amino acid of the mutant manganese peroxidase corresponding to position $X_{a1}$ includes Arginine (R) or Lysine (K). In certain embodiments, amino acid substitution of the mutant manganese peroxidase corresponding to position $X_{a1}$ is Lysine (K).

In some embodiments, the amino acid substitution(s) comprise at least an amino acid substitution at position $X_{b9}$ of the motif set forth in SEQ ID NO:10. Amino acid substitution at this position confers improved manganese peroxidase activity, yielding a mutant manganese peroxidase with an improved manganese peroxidase activity relative to the unmodified manganese peroxidase. In some embodiments, the amino acid at position $X_{b9}$ is substituted with an amino acid that does not correspond to the respective motif as set forth in SEQ ID NO:10. Thus, in some embodiments, the amino acid at position $X_{b9}$, if substituted, is not N, T, A, or E. In some embodiments, amino acid substitutions at position $X_{b9}$ include R, D, C, Q, G, H, I, L, K, M, F, P, S, W, Y, or V. In certain embodiments, amino acid substitution is Serine (S) at position $X_{b9}$.

In some embodiments, the improved manganese peroxidase is a mutant manganese peroxidase comprising a sequence substantially identical (e.g., at least 40%, 45%, 50%, 55%, 60%, 65%, 70%, 75%, 80%, 85%, 90%, 91%, 92%, 93%, 94%, 95%, 96%, 97%, 98%, 99% sequence identity) to any of SEQ ID NOS:1, 2, 3, 4, 5, 6, 7, or 8 and having improved manganese peroxidase activity compared with a control manganese peroxidase (e.g., a manganese peroxidase comprising any of SEQ ID NOS:1, 2, 3, 4, 5, 6, 7, or 8), wherein the amino acid of the mutant manganese peroxidase corresponding to position $X_{b9}$, if substituted, is not N, T, A, or E. In some embodiments, the amino acid of the mutant manganese peroxidase corresponding to position $X_{b9}$ include R, D, C, Q, G, H, I, L, K, M, F, P, S, W, Y, or V. In certain embodiments, the amino acid of the mutant manganese peroxidase corresponding to position $X_{b9}$ is Serine (S).

In some embodiments, the amino acid substitution(s) comprise at least an amino acid substitution at position $X_{b11}$ of the motif set forth in SEQ ID NO:10. Amino acid substitution at this position confers improved manganese peroxidase activity, yielding a mutant manganese peroxidase with an improved manganese peroxidase activity relative to the unmodified manganese peroxidase. In some embodiments, the amino acid at position $X_{b11}$ is substituted with an amino acid that does not correspond to the respective motif as set forth in SEQ ID NO:10. Thus, in some embodiments, the amino acid at position $X_{b11}$, if substituted, is not H, P, D, S, Q, or A. In some embodiments, amino acid substitutions at position $X_{b11}$ include R, N, C, E, G, I, L, K, M, F, T, W, Y, or V. In certain embodiments, amino acid substitutions include Leucine (L), Isoleucine (I), Methionine (M), or Valine (V) at position $X_{b11}$. In certain embodiments, amino acid substitutions include Leucine (L) at position $X_{b11}$.

In some embodiments, the improved manganese peroxidase is a mutant manganese peroxidase comprising a sequence substantially identical (e.g., at least 40%, 45%, 50%, 55%, 60%, 65%, 70%, 75%, 80%, 85%, 90%, 91%, 92%, 93%, 94%, 95%, 96%, 97%, 98%, 99% sequence identity) to any of SEQ ID NOS:1, 2, 3, 4, 5, 6, 7, or 8 and having improved manganese peroxidase activity compared with a control manganese peroxidase (e.g., a manganese peroxidase comprising any of SEQ ID NOS:1, 2, 3, 4, 5, 6, 7, or 8), wherein the amino acid of the mutant manganese peroxidase corresponding to position $X_{b11}$, if substituted, is not H, P, D, S, Q, or A. In some embodiments, the amino acid of the mutant manganese peroxidase corresponding to position $X_{b11}$ include R, N, C, E, G, I, L, K, M, F, T, W, Y, or V. In certain embodiments, the amino acid of the mutant manganese peroxidase corresponding to position $X_{b11}$ includes Leucine (L), Isoleucine (I), Methionine (M), or Valine (V). In certain embodiments, the amino acid of the mutant manganese peroxidase corresponding to position $X_{b11}$ is Leucine (L).

In some embodiments, the amino acid substitution(s) comprise at least an amino acid substitution at position $X_{b13}$ of the motif set forth in SEQ ID NO:10. Amino acid substitution at this position confers improved manganese peroxidase activity, yielding a mutant manganese peroxidase with an improved manganese peroxidase activity relative to the unmodified manganese peroxidase. In some embodiments, the amino acid at position $X_{b13}$ is substituted with an amino acid that does not correspond to the respective motif as set forth in SEQ ID NO:10. Thus, in some embodiments, the amino acid at position $X_{b13}$, if substituted, is not N or S. In some embodiments, amino acid substitutions at position $X_{b13}$ include A, R, D, C, E, Q, G, H, I, L, K, M, F, P, T, W, Y, or V. In certain embodiments, amino acid substitutions include Leucine (L), Isoleucine (I), Methionine (M), or Valine (V) at position $X_{b13}$. In certain embodiments, amino acid substitutions include Leucine (L) at position $X_{b13}$.

In some embodiments, the improved manganese peroxidase is a mutant manganese peroxidase comprising a sequence substantially identical (e.g., at least 40%, 45%, 50%, 55%, 60%, 65%, 70%, 75%, 80%, 85%, 90%, 91%, 92%, 93%, 94%, 95%, 96%, 97%, 98%, 99% sequence identity) to any of SEQ ID NOS:1, 2, 3, 4, 5, 6, 7, or 8 and having improved manganese peroxidase activity compared with a control manganese peroxidase (e.g., a manganese peroxidase comprising any of SEQ ID NOS:1, 2, 3, 4, 5, 6, 7, or 8), wherein the amino acid of the mutant manganese peroxidase corresponding to position $X_{b13}$, if substituted, is not N or S. In some embodiments, the amino acid of the mutant manganese peroxidase corresponding to position $X_{b13}$ include A, R, D, C, E, Q, G, H, I, L, K, M, F, P, T, W, Y, or V. In certain embodiments, the amino acid of the mutant manganese peroxidase corresponding to position $X_{b13}$ includes Leucine (L), Isoleucine (I), Methionine (M), or Valine (V). In certain embodiments, the amino acid of the mutant manganese peroxidase corresponding to position $X_{b13}$ is Leucine (L).

In some embodiments, the amino acid substitution(s) comprise at least an amino acid substitution at position $X_{c11}$ of the motif set forth in SEQ ID NO:11. Amino acid substitution at this position confers improved manganese peroxidase activity, yielding a mutant manganese peroxidase with an improved manganese peroxidase activity relative to the unmodified manganese peroxidase. In some embodiments, the amino acid at position $X_{c11}$ is substituted with an amino acid that does not correspond to the respective motif as set forth in SEQ ID NO:11. Thus, in some embodiments, the amino acid at position $X_{c11}$, if substituted, is not A, Q, or R. In some embodiments, amino acid substitutions at position $X_{c11}$ include N, D, C, E, G, H, I, L, K, M, F, P, T, W, Y, S or V. In some embodiments, the amino acid at position $X_{c11}$, if substituted, is not Q or R. In certain embodiments, amino acid substitutions include Alanine (A) or Glycine (G) at position $X_{c11}$. In certain embodiments, amino acid substitutions include Alanine (A) at position $X_{c11}$.

In some embodiments, the improved manganese peroxidase is a mutant manganese peroxidase comprising a sequence substantially identical (e.g., at least 40%, 45%, 50%, 55%, 60%, 65%, 70%, 75%, 80%, 85%, 90%, 91%, 92%, 93%, 94%, 95%, 96%, 97%, 98%, 99% sequence identity) to any of SEQ ID NOS:1, 2, 3, 4, 5, 6, 7, or 8 and having improved manganese peroxidase activity compared with a control manganese peroxidase (e.g., a manganese peroxidase comprising any of SEQ ID NOS:1, 2, 3, 4, 5, 6, 7, or 8), wherein the amino acid of the mutant manganese peroxidase corresponding to position $X_{c11}$, if substituted, is not A, Q, or R. In some embodiments, the amino acid of the mutant manganese peroxidase corresponding to position $X_{c11}$ include N, D, C, E, G, H, I, L, K, M, F, P, T, W, Y, S or V. In some embodiments, the amino acid of the mutant manganese peroxidase corresponding to position $X_{c11}$, if substituted, is not Q or R. In certain embodiments, the amino acid of the mutant manganese peroxidase corresponding to position $X_{c11}$ includes Alanine (A) or Glycine (G). In certain embodiments, the amino acid of the mutant manganese peroxidase corresponding to position $X_{c11}$ is Alanine (A).

In some embodiments, the amino acid substitution(s) comprise at least an amino acid substitution at position $X_{d3}$ of the motif set forth in SEQ ID NO:12. Amino acid substitution at this position confers improved manganese peroxidase activity, yielding a mutant manganese peroxidase with an improved manganese peroxidase activity relative to the unmodified manganese peroxidase. In some embodiments, the amino acid at position $X_{d3}$ is substituted with an amino acid that does not correspond to the respective motif as set forth in SEQ ID NO:12. Thus, in some embodiments, the amino acid at position $X_{d3}$, if substituted, is not S or T. In some embodiments, amino acid substitutions at position $X_{d3}$ include A, R, N, D, C, E, Q, G, H, I, L, K, M, F, P, W, Y, or V. In some embodiments, the amino acid at position $X_{d3}$, if substituted, is not T. In certain embodiments, amino acid substitutions include Serine (S) at position $X_{d3}$.

In some embodiments, the improved manganese peroxidase is a mutant manganese peroxidase comprising a sequence substantially identical (e.g., at least 40%, 45%, 50%, 55%, 60%, 65%, 70%, 75%, 80%, 85%, 90%, 91%, 92%, 93%, 94%, 95%, 96%, 97%, 98%, 99% sequence identity) to any of SEQ ID NOS:1, 2, 3, 4, 5, 6, 7, or 8 and having improved manganese peroxidase activity compared with a control manganese peroxidase (e.g., a manganese peroxidase comprising any of SEQ ID NOS:1, 2, 3, 4, 5, 6, 7, or 8), wherein the amino acid of the mutant manganese peroxidase corresponding to position $X_{d3}$, if substituted, is not S or T. In some embodiments, the amino acid of the mutant manganese peroxidase corresponding to position $X_{d3}$ include A, R, N, D, C, E, Q, G, H, I, L, K, M, F, P, W, Y, or V. In some embodiments, the amino acid of the mutant manganese peroxidase corresponding to position $X_{d3}$, if substituted, is not T. In certain embodiments, the amino acid of the mutant manganese peroxidase corresponding to position $X_{d3}$ is Serine (S).

In some embodiments, the amino acid substitution(s) comprise at least an amino acid substitution at position $X_{e9}$ of the motif set forth in SEQ ID NO:13. Amino acid substitution at this position confers improved manganese peroxidase activity, yielding a mutant manganese peroxidase with an improved manganese peroxidase activity relative to the unmodified manganese peroxidase. In some embodiments, the amino acid at position $X_{e9}$ is substituted with an amino acid that does not correspond to the respective motif as set forth in SEQ ID NO:13. Thus, in some embodiments, the amino acid at position $X_{e9}$, if substituted, is not W. In some embodiments, amino acid substitutions at position $X_{e9}$ include A, R, N, D, C, E, Q, G, H, I, L, K, M, F, P, S, T, Y, or V. In certain embodiments, amino acid substitutions include Alanine (A) or Glycine (G) at position $X_{e9}$. In certain embodiments, amino acid substitutions include Alanine (A) at position $X_{e9}$.

In some embodiments, the improved manganese peroxidase is a mutant manganese peroxidase comprising a sequence substantially identical (e.g., at least 40%, 45%, 50%, 55%, 60%, 65%, 70%, 75%, 80%, 85%, 90%, 91%, 92%, 93%, 94%, 95%, 96%, 97%, 98%, 99% sequence identity) to any of SEQ ID NOS:1, 2, 3, 4, 5, 6, 7, or 8 and having improved manganese peroxidase activity compared with a control manganese peroxidase (e.g., a manganese peroxidase comprising any of SEQ ID NOS:1, 2, 3, 4, 5, 6, 7, or 8), wherein the amino acid of the mutant manganese peroxidase corresponding to position $X_{e9}$, if substituted, is not W. In some embodiments, the amino acid of the mutant manganese peroxidase corresponding to position $X_{e9}$ include A, R, N, D, C, E, Q, G, H, I, L, K, M, F, P, S, T, Y, or V. In certain embodiments, the amino acid of the mutant manganese peroxidase corresponding to position $X_{e9}$ includes Alanine (A) or Glycine (G). In certain embodiments, the amino acid of the mutant manganese peroxidase corresponding to position $X_{e9}$ is Alanine (A).

In some embodiments, the improved manganese peroxidase is a mutant manganese peroxidase comprising a sequence substantially identical (e.g., at least 40%, 45%, 50%, 55%, 60%, 65%, 70%, 75%, 80%, 85%, 90%, 91%, 92%, 93%, 94%, 95%, 96%, 97%, 98%, 99%) to SEQ ID NO:1 and having improved manganese peroxidase activity compared with a control manganese peroxidase (e.g., a manganese peroxidases comprising SEQ ID NO:1), wherein the amino acid of the mutant manganese peroxidase corresponding to position 17 of SEQ ID NO:1, if substituted, is not Q. In some embodiments, the amino acid of the mutant manganese peroxidase corresponding to position 17 of SEQ ID NO:1 include A, R, N, D, C, E, G, H, I, L, K, M, F, P, S, T, Y, W or V. In certain embodiments, the amino acid of the mutant manganese peroxidase corresponding to position 17 of SEQ ID NO:1 is Serine (S).

In some embodiments, the improved manganese peroxidase is a mutant manganese peroxidase comprising a sequence substantially identical (e.g., at least 40%, 45%, 50%, 55%, 60%, 65%, 70%, 75%, 80%, 85%, 90%, 91%, 92%, 93%, 94%, 95%, 96%, 97%, 98%, 99%) to SEQ ID NO:1 and having improved manganese peroxidase activity compared with a control manganese peroxidase (e.g., a manganese peroxidases comprising SEQ ID NO:1), wherein the amino acid of the mutant manganese peroxidase corresponding to position 80 of SEQ ID NO:1, if substituted, is not S. In some embodiments, the amino acid of the mutant manganese peroxidase corresponding to position 80 of SEQ ID NO:1 include A, R, N, D, C, E, G, H, I, L, K, M, F, P, T, Y, W, Q or V. In certain embodiments, the amino acid of the mutant manganese peroxidase corresponding to position 80 of SEQ ID NO:1 is Asparagine (N).

Other suitable amino acid substitution(s) at one or more of the sites identified above can be determined using, e.g., known methods of site-directed mutagenesis and determination of manganese peroxidase activity in assays described further herein or otherwise known to persons of skill in the art. In some embodiments, the improved manganese peroxidases comprise at least non-naturally encoded amino acid. For example, in some embodiments, any of the amino acid substitutions discussed herein can be an amino acid substitution by a non-naturally encoded amino acid.

In some embodiments, the improved manganese peroxidases comprise various combinations of substitutions discussed above. For example, in some embodiments, the improved manganese peroxidases comprise two, three, four, five, or more mutations selected from the group consisting of: (a) an amino acid substitution at position $X_{a1}$ of the motif set forth in SEQ ID NO:9; (b) an amino acid substitution at position $X_{b9}$ of the motif set forth in SEQ ID NO:10; (c) an amino acid substitution at position $X_{b11}$ of the motif set forth in SEQ ID NO:10; (d) an amino acid substitution at position $X_{b13}$ of the motif set forth in SEQ ID NO:10; (e) an amino acid substitution at position $X_{c11}$ of the motif set forth in SEQ ID NO:11; (f) an amino acid substitution at position $X_{d3}$ of the motif set forth in SEQ ID NO:12; and (g) an amino acid substitution at position $X_{e9}$ of the motif set forth in SEQ ID NO:13, wherein the control manganese peroxidase has the same amino acid sequence as the mutant manganese peroxidase except that the amino acid of the control manganese peroxidase comprises SEQ ID NOS:9-13.

In some embodiments, the improved manganese peroxidase is a mutant manganese peroxidase comprising a sequence substantially identical (e.g., at least 40%, 45%, 50%, 55%, 60%, 65%, 70%, 75%, 80%, 85%, 90%, 91%, 92%, 93%, 94%, 95%, 96%, 97%, 98%, 99% sequence identity) to any of SEQ ID NOS:1, 2, 3, 4, 5, 6, 7, or 8 and having improved manganese peroxidase activity compared with a control manganese peroxidase (e.g., a manganese peroxidase comprising any of SEQ ID NOS:1, 2, 3, 4, 5, 6, 7, or 8), wherein the improved manganese peroxidases comprise two, three, four, five, six, seven or more mutations selected from the group consisting of: (a) an amino acid substitution at a position corresponding to position $X_{a1}$; (b) an amino acid substitution at a position corresponding to position $X_{b9}$; (c) an amino acid substitution at a position corresponding to position $X_{b11}$; (d) an amino acid substitution at a position corresponding to position $X_{b13}$; (e) an amino acid substitution at a position corresponding to position $X_{c11}$; (f) an amino acid substitution at a position corresponding to position $X_{d3}$; and (g) an amino acid substitution at a position corresponding to position $X_{e9}$, wherein the control manganese peroxidase has the same amino acid sequence as the mutant manganese peroxidase except that the control manganese peroxidase does not have these mutations.

In some embodiments, unmodified forms of manganese peroxidase amenable to mutation in accordance with the present invention are those having an active site domain comprising Motif B. In some embodiments, the amino acid substitution(s) comprise at least amino acid substitutions at positions $X_{b9}$, $X_{b11}$, and $X_{b13}$ of the motif set forth in SEQ ID NO:10. Amino acid substitutions at these positions confer improved manganese peroxidase activity, yielding a mutant manganese peroxidase with an improved manganese peroxidase activity relative to the unmodified manganese peroxidase. In some embodiments, the amino acid at position $X_{b9}$ is substituted with an amino acid that does not correspond to the respective motif as set forth in SEQ ID NO:10, the amino acid at position $X_{b11}$ is substituted with an amino acid that does not correspond to the respective motif as set forth in SEQ ID NO:10, and the amino acid at position $X_{b13}$ is substituted with an amino acid that does not correspond to the respective motif as set forth in SEQ ID NO:10. Thus, in some embodiments, the amino acid at position $X_{b9}$, if substituted, is not N, T, A, or E, the amino acid at position $X_{b11}$, if substituted, is not H, P, D, S, Q, or A, the amino acid at position $X_{b13}$, if substituted, is not N or S. In certain embodiments, amino acid substitutions include Serine (S) at position $X_{b9}$, Leucine (L) at position $X_{b11}$, and Leucine (L) at position $X_{b13}$.

In some embodiments, the improved manganese peroxidase is a mutant manganese peroxidase comprising a sequence substantially identical (e.g., at least 40%, 45%, 50%, 55%, 60%, 65%, 70%, 75%, 80%, 85%, 90%, 91%, 92%, 93%, 94%, 95%, 96%, 97%, 98%, 99% sequence identity) to any of SEQ ID NOS:1, 2, 3, 4, 5, 6, 7, or 8 and having improved manganese peroxidase activity compared with a control manganese peroxidase (e.g., a manganese peroxidase comprising any of SEQ ID NOS:1, 2, 3, 4, 5, 6, 7, or 8), wherein the amino acid of the mutant manganese peroxidase corresponding to position $X_{b9}$ is not N, T, A, or E, the amino acid of the mutant manganese peroxidase corresponding to position $X_{b11}$ is not H, P, D, S, Q, or A, the amino acid of the mutant manganese peroxidase corresponding to position $X_{b13}$ is not N or S. In certain embodiments, the amino acid of the mutant manganese peroxidase corresponding to position $X_{b9}$ is Serine (S), the amino acid of the mutant manganese peroxidase corresponding to position $X_{b11}$ is Leucine (L), and the amino acid of the mutant manganese peroxidase corresponding to position $X_{b13}$ is Leucine (L).

In some embodiments, unmodified forms of manganese peroxidase amenable to mutation in accordance with the present invention are those having an active site domain comprising both Motif B and Motif E. In some embodiments, the amino acid substitution(s) comprise at least amino acid substitutions at positions $X_{b9}$, $X_{b11}$, and $X_{b13}$ of the motif set forth in SEQ ID NO:10, and position $X_{e9}$ of the motif set forth in SEQ ID NO:13. Amino acid substitutions at these positions confer improved manganese peroxidase activity, yielding a mutant manganese peroxidase with an improved manganese peroxidase activity relative to the unmodified manganese peroxidase. In some embodiments, the amino acid at position $X_{b9}$ is substituted with an amino acid that does not correspond to the respective motif as set forth in SEQ ID NO:10, the amino acid at position $X_{b11}$ is substituted with an amino acid that does not correspond to the respective motif as set forth in SEQ ID NO:10, the amino acid at position $X_{b13}$ is substituted with an amino acid that does not correspond to the respective motif as set forth in SEQ ID NO:10, and the amino acid at position $X_{e9}$ is substituted with an amino acid that does not correspond to the respective motif as set forth in SEQ ID NO:13. Thus, in some embodiments, the amino acid at position $X_{b9}$, if substituted, is not N, T, A, or E, the amino acid at position $X_{b11}$, if substituted, is not H, P, D, S, Q, or A, the amino acid at position $X_{b13}$, if substituted, is not N or S, the amino acid at position $X_{e9}$, if substituted, is not W. In certain embodiments, amino acid substitutions include Serine (S) at position $X_{b9}$, Leucine (L) at position $X_{b11}$, Leucine (L) at position $X_{b13}$, and Alanine (A) at position $X_{e9}$.

In some embodiments, the improved manganese peroxidase is a mutant manganese peroxidase comprising a sequence substantially identical (e.g., at least 40%, 45%, 50%, 55%, 60%, 65%, 70%, 75%, 80%, 85%, 90%, 91%, 92%, 93%, 94%, 95%, 96%, 97%, 98%, 99% sequence identity) to any of SEQ ID NOS:1, 2, 3, 4, 5, 6, 7, or 8 and having improved manganese peroxidase activity compared with a control manganese peroxidase (e.g., a manganese peroxidase comprising any of SEQ ID NOS:1, 2, 3, 4, 5, 6, 7, or 8), wherein the amino acid of the mutant manganese peroxidase corresponding to position $X_{b9}$ is not N, T, A, or E, and the amino acid of the mutant manganese peroxidase corresponding to position $X_{e9}$ is not W. In certain embodiments, the amino acid of the mutant manganese peroxidase corresponding to position $X_{b9}$ is Serine (S), and the amino acid of the mutant manganese peroxidase corresponding to position $X_{e9}$ is Alanine (A).

In some embodiments, unmodified forms of manganese peroxidase amenable to mutation in accordance with the present invention are those having all three motifs of Motif A, Motif B and Motif C. In some embodiments, the amino acid substitution(s) comprise at least amino acid substitutions at position $X_{a1}$ of the motif set forth in SEQ ID NO:9, positions $X_{b9}$, $X_{b11}$, and $X_{b13}$ of the motif set forth in SEQ ID NO:10, and position $X_{c11}$ of the motif set forth in SEQ ID NO:11. Amino acid substitutions at these positions confer improved manganese peroxidase activity, yielding a mutant manganese peroxidase with an improved manganese peroxidase activity relative to the unmodified manganese peroxidase. In some embodiments, the amino acid at position $X_{a1}$ is substituted with an amino acid that does not correspond to the respective motif as set forth in SEQ ID NO:9, the amino acid at position $X_{b9}$ is substituted with an amino acid that does not correspond to the respective motif as set forth in SEQ ID NO:10, the amino acid at position $X_{b11}$ is substituted with an amino acid that does not correspond to the respective motif as set forth in SEQ ID NO:10, the amino acid at position $X_{b13}$ is substituted with an amino acid that does not correspond to the respective motif as set forth in SEQ ID NO:10, and the amino acid at position $X_{c11}$ is substituted with an amino acid that does not correspond to the respective motif as set forth in SEQ ID NO:11. Thus, in some embodiments, the amino acid at position $X_{a1}$, if substituted, is not D, H, G, Q or E, the amino acid at position $X_{b9}$, if substituted, is not N, T, A, or E, the amino acid at position $X_{b11}$, if substituted, is not H, P, D, S, Q, or A, the amino acid at position $X_{b13}$, if substituted, is not N or S, the amino acid at position $X_{c11}$, if substituted, is not A, Q, or R. In certain embodiments, amino acid substitutions include Lysine (K) at position $X_{a1}$, Serine (S) at position $X_{b9}$, Leucine (L) at position $X_{b11}$, Leucine (L) at position $X_{b13}$, Alanine (A) at position $X_{c11}$.

In some embodiments, the improved manganese peroxidase is a mutant manganese peroxidase comprising a sequence substantially identical (e.g., at least 40%, 45%, 50%, 55%, 60%, 65%, 70%, 75%, 80%, 85%, 90%, 91%, 92%, 93%, 94%, 95%, 96%, 97%, 98%, 99% sequence identity) to any of SEQ ID NOS:1, 2, 3, 4, 5, 6, 7, or 8 and having improved manganese peroxidase activity compared with a control manganese peroxidase (e.g., a manganese peroxidase comprising any of SEQ ID NOS:1, 2, 3, 4, 5, 6, 7, or 8), wherein the amino acid of the mutant manganese peroxidase corresponding to position $X_{a1}$ is not D, H, G, Q or E, the amino acid of the mutant manganese peroxidase corresponding to position $X_{b9}$ is not N, T, A, or E, the amino acid of the mutant manganese peroxidase corresponding to position $X_{b11}$ is not H, P, D, S, Q, or A, the amino acid of the mutant manganese peroxidase corresponding to position $X_{b13}$ is not N or S, and the amino acid of the mutant manganese peroxidase corresponding to position $X_{c11}$ is not A, Q, or R. In certain embodiments, the amino acid of the mutant manganese peroxidase corresponding to position $X_{a1}$ is Lysine (K), the amino acid of the mutant manganese peroxidase corresponding to position $X_{b9}$ is Serine (S), the amino acid of the mutant manganese peroxidase corresponding to position $X_{b11}$ is Leucine (L), the amino acid of the mutant manganese peroxidase corresponding to position $X_{b13}$ is Leucine (L), and the amino acid of the mutant manganese peroxidase corresponding to position $X_{c11}$ is Alanine (A).

Other suitable amino acid substitution(s) at one or more of the sites identified above can be determined using, e.g., known methods of site-directed mutagenesis and determination of manganese peroxidase activity in assays described further herein or otherwise known to persons of skill in the art.

Further provided herein are improved manganese peroxidases having improved MnP activity compared to a control manganese peroxidase (e.g., a manganese peroxidase comprising SEQ ID NO:1). In some embodiments, the improved manganese peroxidase is a mutant manganese peroxidase having at least 90% sequence identity to SEQ ID NO:1 and improved manganese peroxidase activity compared with a control manganese peroxidase (e.g., a manganese peroxidase comprising SEQ ID NO:1).

In some embodiments, the amino acid of the mutant manganese peroxidase corresponding to position 57 of SEQ ID NO:1 is any amino acid other than D, and the control manganese peroxidase has the same amino acid sequence as the mutant manganese peroxidase except that the amino acid of the control manganese peroxidase corresponding to position 57 of SEQ ID NO:1 is D. In some embodiments, the amino acid of the mutant manganese peroxidase corresponding to position 57 of SEQ ID NO:1 is K.

In some embodiments, the amino acid of the mutant manganese peroxidase corresponding to position 107 of SEQ ID NO:1 is any amino acid other than N, and the control manganese peroxidase has the same amino acid sequence as the mutant manganese peroxidase except that the amino acid of the control manganese peroxidase corresponding to position 107 of SEQ ID NO:1 is N. In some embodiments, the amino acid of the mutant manganese peroxidase corresponding to position 107 of SEQ ID NO:1 is S.

In some embodiments, the amino acid of the mutant manganese peroxidase corresponding to position 109 of SEQ ID NO:1 is any amino acid other than H, and the control manganese peroxidase has the same amino acid sequence as the mutant manganese peroxidase except that the amino acid of the control manganese peroxidase corresponding to position 109 of SEQ ID NO:1 is H. In some embodiments, the amino acid of the mutant manganese peroxidase corresponding to position 109 of SEQ ID NO:1 is L.

In some embodiments, the amino acid of the mutant manganese peroxidase corresponding to position 111 of SEQ ID NO:1 is any amino acid other than N, and the control manganese peroxidase has the same amino acid sequence as the mutant manganese peroxidase except that the amino acid of the control manganese peroxidase corresponding to position 111 of SEQ ID NO:1 is N. In some embodiments, the amino acid of the mutant manganese peroxidase corresponding to position 111 of SEQ ID NO:1 is L.

In some embodiments, the amino acid of the mutant manganese peroxidase corresponding to position 152 of SEQ ID NO:1 is any amino acid other than Q, and the control manganese peroxidase has the same amino acid sequence as the mutant manganese peroxidase except that the amino acid of the control manganese peroxidase corresponding to position 152 of SEQ ID NO:1 is Q. In some embodiments, the amino acid of the mutant manganese peroxidase corresponding to position 152 of SEQ ID NO:1 is A.

In some embodiments, the amino acid of the mutant manganese peroxidase corresponding to position 278 of SEQ ID NO:1 is any amino acid other than W, and the control manganese peroxidase has the same amino acid sequence as the mutant manganese peroxidase except that the amino acid of the control manganese peroxidase corresponding to position 278 of SEQ ID NO:1 is W. In some embodiments, the amino acid of the mutant manganese peroxidase corresponding to position 278 of SEQ ID NO:1 is A.

In some embodiments, the amino acid of the mutant manganese peroxidase corresponding to position 204 of SEQ ID NO:1 is any amino acid other than T, and the control manganese peroxidase has the same amino acid sequence as the mutant manganese peroxidase except that the amino acid of the control manganese peroxidase corresponding to position 204 of SEQ ID NO:1 is T. In some embodiments, the amino acid of the mutant manganese peroxidase corresponding to position 204 of SEQ ID NO:1 is S.

In some embodiments, the amino acid of the mutant manganese peroxidase corresponding to position 17 of SEQ ID NO:1 is any amino acid other than Q, and the control manganese peroxidase has the same amino acid sequence as the mutant manganese peroxidase except that the amino acid of the control manganese peroxidase corresponding to position 17 of SEQ ID NO:1 is Q. In some embodiments, the amino acid of the mutant manganese peroxidase corresponding to position 17 of SEQ ID NO:1 is S.

In some embodiments, the amino acid of the mutant manganese peroxidase corresponding to position 80 of SEQ ID NO:1 is any amino acid other than S, and the control manganese peroxidase has the same amino acid sequence as the mutant manganese peroxidase except that the amino acid of the control manganese peroxidase corresponding to position 80 of SEQ ID NO:1 is S. In some embodiments, the amino acid of the mutant manganese peroxidase corresponding to position 80 of SEQ ID NO:1 is N.

In some embodiments, the mutant manganese peroxidase comprises two, three, four, five, or more mutations as described herein. For example, the mutant manganese peroxidase comprises two, three, four, five, six, seven, eight, nine or more mutations selected from the group consisting of (a) position 57 of SEQ ID NO:1 having an amino acid other than D (e.g., Lysine); (b) position 107 of SEQ ID NO:1 having an amino acid other than N (e.g., Serine); (c) position 109 of SEQ ID NO:1 having an amino acid other than H (e.g., Leucine); (d) position 111 of SEQ ID NO:1 having an amino acid other than N (e.g., Leucine); (e) position 152 of SEQ ID NO:1 having an amino acid other than Q (e.g., Alanine); (f) position 278 of SEQ ID NO:1 having an amino acid other than W (e.g., Alanine); (g) position 204 of SEQ ID NO:1 having an amino acid other than T (e.g., Serine); (h) position 17 of SEQ ID NO:1 having an amino acid other than Q (e.g., Serine); (i) position 80 of SEQ ID NO: 1 having an amino acid other than S (e.g., Asparagine); and the control manganese peroxidase has the same amino acid sequence as the mutant manganese peroxidase except that the amino acid of the control manganese peroxidase corresponding to position 57 of SEQ ID NO:1 is D, the amino acid of the control manganese peroxidase corresponding to position 107 of SEQ ID NO:1 is N, the amino acid of the control manganese peroxidase corresponding to position 109 of SEQ ID NO:1 is H, the amino acid of the control manganese peroxidase corresponding to position 111 of SEQ ID NO:1 is N, the amino acid of the control manganese peroxidase corresponding to position 152 of SEQ ID NO:1 is Q, the amino acid of the control manganese peroxidase corresponding to position 278 of SEQ ID NO:1 is W, the amino acid of the control manganese peroxidase corresponding to position 204 of SEQ ID NO:1 is T, the amino acid of the control manganese peroxidase corresponding to position 17 of SEQ ID NO:1 is Q, and the amino acid of the control manganese peroxidase corresponding to position 80 of SEQ ID NO:1 is S. In some embodiments, the mutant manganese peroxidase comprises (a) position 107 of SEQ ID NO:1 having an amino acid other than N (e.g., Serine); (b) position 109 of SEQ ID NO:1 having an amino acid other than H (e.g., Leucine); (c) position 111 of SEQ ID NO:1 having an amino acid other than N (e.g., Leucine); and the control manganese peroxidase has the same amino acid sequence as the mutant manganese peroxidase except that the amino acid of the control manganese peroxidase corresponding to position 107 of SEQ ID NO:1 is N, the amino acid of the control manganese peroxidase corresponding to position 109 of SEQ ID NO:1 is H, the amino acid of the control manganese peroxidase corresponding to position 111 of SEQ ID NO:1 is N. In some embodiments, the mutant manganese peroxidase comprises (a) position 107 of SEQ ID NO:1 having an amino acid other than N (e.g., Serine); (b) position 109 of SEQ ID NO:1 having an amino acid other than H (e.g., Leucine); (c) position 111 of SEQ ID NO:1 having an amino acid other than N (e.g., Leucine); (d) position 278 of SEQ ID NO:1 having an amino acid other than W (e.g., Alanine); and the control manganese peroxidase has the same amino acid sequence as the mutant manganese peroxidase except that the amino acid of the control manganese peroxidase corresponding to position 107 of SEQ ID NO:1 is N, the amino acid of the control manganese peroxidase corresponding to position 109 of SEQ ID NO:1 is H, the amino acid of the control manganese peroxidase corresponding to position 111 of SEQ ID NO:1 is N, and the amino acid of the control manganese peroxidase corresponding to position 278 of SEQ ID NO:1 is W. In some embodiments, the mutant manganese peroxidase comprises (a) position 107 of SEQ ID NO:1 having an amino acid other than N (e.g., Serine); (b) position 109 of SEQ ID NO:1 having an amino acid other than H (e.g., Leucine); (c) position 111 of SEQ ID NO:1 having an amino acid other than N (e.g., Leucine); (d) position 57 of SEQ ID NO:1 having an amino acid other than D (e.g., Lysine); (e) position 152 of SEQ ID NO:1 having an amino acid other than Q (e.g., Alanine); and the control manganese peroxidase has the same amino acid sequence as the mutant manganese peroxidase except that the amino acid of the control manganese peroxidase corresponding to position 107 of SEQ ID NO:1 is N, the amino acid of the control manganese peroxidase corresponding to position 109 of SEQ ID NO:1 is H, the amino acid of the control manganese peroxidase corresponding to position 111 of SEQ ID NO:1 is N, the amino acid of the control manganese peroxidase corresponding to position 57 of SEQ ID NO:1 is D, and the amino acid of the control manganese peroxidase corresponding to position 152 of SEQ ID NO:1 is Q. In some embodiments, the mutant manganese peroxidase comprises (a) position 107 of SEQ ID NO:1 having an amino acid other than N (e.g., Serine); (b) position 109 of SEQ ID NO:1 having an amino acid other than H (e.g., Leucine); (c) position 111 of SEQ ID NO:1 having an amino acid other than N (e.g., Leucine); (d) position 57 of SEQ ID NO:1 having an amino acid other than D (e.g., Lysine); (e) position 152 of SEQ ID NO:1 having an amino acid other than Q (e.g., Alanine); (f) position 17 of SEQ ID NO:1 having an amino acid other than Q (e.g., Serine); (g) position 80 of SEQ ID NO:1 having an amino acid other than S (e.g., Asparagine); and the control manganese peroxidase has the same amino acid sequence as the mutant manganese peroxidase except that the amino acid of the control manganese peroxidase corresponding to position 107 of SEQ ID NO:1 is N, the amino acid of the control manganese peroxidase corresponding to position 109 of SEQ ID NO:1 is H, the amino acid of the control manganese peroxidase corresponding to position 111 of SEQ ID NO:1 is N, the amino acid of the control manganese peroxidase corresponding to position 57 of SEQ ID NO:1 is D, the amino acid of the control manganese peroxidase corresponding to position 152 of SEQ ID NO:1 is Q; the amino acid of the control manganese peroxidase corresponding to position 17 of SEQ ID NO:1 is Q, the amino acid of the control manganese peroxidase corresponding to position 80 of SEQ ID NO:1 is S.

The improved manganese peroxidases or other enzymes discussed herein may be recombinantly expressed by molecular cloning into an expression vector containing a suitable promoter and other appropriate transcription regulatory elements, and transferred into prokaryotic or eukaryotic host cells to produce recombinant enzymes. Techniques for such manipulations are fully described by Sambrook et al. (Molecular Cloning: A Laboratory Manual; Cold Spring Harbor Laboratory, Cold Spring Harbor, N.Y., (1989); Current Protocols in Molecular Biology, Ausubel et al., Green Pub. Associates and Wiley-Interscience, New York (1988); Yeast Genetics: A Laboratory Course Manual, Rose et al., Cold Spring Harbor Laboratory, Cold Spring Harbor, N.Y., (1990)).

A variety of techniques are available and known to those skilled in the art for introduction of nucleic acid constructs into a cellular host. Transformation of microbial cells may be accomplished through, e.g., use of polyethylene glycol, calcium chloride, viral infection, DEAE dextran, phage infection, electroporation and other methods known in the art. Transformation of fungus, in particular *Pichia*, may be accomplished, for example, according to "*Pichia* Protocols", in *Methods Mol. Biol.*, Higgins, David R. and Cregg, James M.; Eds. (Humana, Totowa, N.J.) (1998). Introduction of the recombinant vector into yeasts can be accomplished by methods including electroporation, use of spheroplasts, lithium acetate, and the like.

Polynucleotides comprising a nucleic acid encoding the improved manganese peroxidases are also provided. In some embodiments, the polynucleotide comprises an expression cassette comprising a heterologous promoter operably linked to the nucleic acid. Also provided herein are vectors comprising the polynucleotides provided herein, and isolated cells or culture of cells comprising the polynucleotides that is heterologous to the cell. In some embodiments, the cell is a bacteria or yeast cell. In some embodiments, the cell is a *Saccharomyces cerevisiae*.

III. Yeasts

In some embodiments, the improved manganese peroxidases or other enzymes discussed herein are expressed in one or more yeast strain. Any yeast strain can be used according to the present invention. Yeast are unicellular microorganisms that belong to one of three classes: Ascomycetes, Basidiomycetes and Fungi Imperfecti. While pathogenic yeast strains, or nonpathogenic mutants thereof, can be used in accordance with the present invention, nonpathogenic yeast strains will generally be used. Exemplary genera of yeast strains include *Saccharomyces, Candida, Cryptococcus, Hansenula, Kluyveromyces, Pichia, Rhodotorula, Schizosaccharomyces* and *Yarrowia*. Exemplary species of yeast strains include *Saccharomyces cerevisiae, Saccharomyces carlsbergensis, Candida albicans, Candida kefyr, Candida tropicalis, Cryptococcus laurentii, Cryptococcus neoformans, Hansenula anomala, Hansenula polymorphs, Kluyveromyces fragilis, Kluyveromyces lactis, Kluyveromyces marxianus* var. *lactis, Pichia pastoris, Rhodotorula rubra, Schizosaccharomyces pombe*, and *Yarrowia lipolytica*. It is to be appreciated that a number of these species include a variety of subspecies, types, subtypes, etc. that are meant to be included within the aforementioned species. In some embodiments, a yeast strain capable of replicating plasmids to a particularly high copy number is used. In some embodiments, a temperature-tolerant yeast strain is used. In some embodiments, an inhibitor-tolerant yeast strain is used.

The present invention provides for yeast strains that express the improved manganese peroxidases or other enzymes discussed herein. Yeast expressing the improved manganese peroxidases or other enzymes discussed herein can be generated as is known in the art. For example, expression cassettes comprising a promoter operably linked to a coding sequence for the improved manganese peroxidases or other enzymes discussed herein can be (optionally inserted into a nucleic acid vector and) introduced into the yeast. A number of expression vectors for various yeast species are known in the art and some can be obtained commercially. Vectors can optionally include an origin of replication and/or a marker gene for identifying cells transformed with the vector. In some embodiments, the expression cassettes are stably introduced into a yeast chromosome or extrachromosomal DNA.

Any number of promoters can be used to drive expression from the expression cassettes of the invention. Exemplary promoters include, e.g., constitutive or inducible promoters. Recombinant gene expression can be driven by promoters including, but not limited to, the yeast GAL10 gene promoter, the phosphoglycerate kinase (PGK) promoter (see, e.g., Tuite, M. F. et. al. (1982) *EMBO Journal* 1, 603-608.; WO 84/04757), GAL10/PGK promoter chimeras (see, e.g., U.S. Pat. No. 5,739,007) or other yeast promoters such as alcohol dehydrogenase (see, e.g., Bennetzen, J. L. and Hall, B. D. *J. Biol. Chem.* 257:3018 (1982); Ammerer, G. in *Methods in Enzymology* Vol. 101, p. 192 (1983)) phosphoglycerate kinase (see, e.g., Derynck, R., Hitzemann, R. A., Gray, P. W., Goeddel, D. V., in *Experimental Manipulation of Gene Expression,* 1983, p. 247, ed. M. Inouye, Academic Press), triose phosphate isomerase (see, e.g., Alber, T. and Kawasaki, G., *J. Molec and Applied Genet.* 1: 419-434 (1982)), or enolase (see, e.g., Innes, M. A. et al. *Science* 226:21 (1985)) can be used in a similar manner.

The yeast can be engineered to secrete proteins into a cellulose source (e.g., a fermentation "mash") at a balanced rate of production that uniquely controls the rate of fermentation by control of enzyme expression. By the careful selection of promoters driving expression of the enzymes, the level of protein production can be gated, permitting fermentations to proceed at measured or controlled rates. In other words, the rate of sugar production (or ethanol production) is controlled by release of enzymes.

Expression vectors used in yeast cells can also contain sequences necessary for the termination of transcription and for stabilizing the mRNA. Such sequences are commonly available from 3' to the translation termination codon, in untranslated regions of eukaryotic or viral DNAs or cDNAs. These regions contain nucleotide segments transcribed as polyadenylated fragments in the untranslated portion of the mRNA.

Yeast cells can be engineered to secrete the improved manganese peroxidases or other enzymes discussed herein or optionally can be engineered such that the proteins are active and attached to the surface of the yeast cells. A variety of methods are known for secretion of heterologous proteins from yeast. See, for example, US Patent Publication Nos. 2007/0077619 and 2006/0234351 and European Patent EP0256421. In some embodiments, secretion is achieved by inclusion of an appropriate signal sequence as a fusion with the enzyme. Exemplary signal sequences are described in the art, including not limited to, U.S. Pat. No. 5,521,086.

Optionally, one or more of the enzymes expressed from a yeast strain is attached to the surface to the yeast cell surface. In some embodiments, the proteins of the present invention are fused to α-agglutinin or a fragment thereof, resulting in surface expression. See, e.g., Murai et al., *Applied and Environmental Microbiology,* 64(12):4857-4861 (1998).

IV. Method for Converting a Cellulose-containing Biomass Feedstock to Ethanol

In some embodiments, the cellulose-containing biomass feedstock is added directly to the mutant manganese peroxidases provided herein (e.g., as expressed in yeast cultures/suspensions) to form an aqueous mixture and incubated under conditions to allow for efficient conversion of the cellulose-containing biomass feedstock to simple sugars. If desired, the sugars can then be further converted to ethanol via fermentation or can be converted to other desired products. Accordingly, provided herein are methods for converting a cellulose-containing biomass feedstock to ethanol by using procedures including treating the biomass with a mutant manganese peroxidase provided herein. In some embodiments, the cellulose-containing biomass feedstock is first converted into sugar, and the resulting sugar is subsequently converted into ethanol (e.g., by other components or by a yeast cell). In some embodiments, the cellulose-containing biomass feedstock is corn grain or corn stover.

In some embodiments, the cellulose-containing biomass feedstock is contacted with a cell expressing a heterologous manganese peroxidase, e.g., the mutant manganese peroxidase provided herein. The heterologous manganese peroxidase-expressing cell can be any cell known in the art, including bacteria, yeast, insect, or mammalian cells.

Mixture of the cellulose-containing biomass feedstock with a cell (e.g., a yeast cell) expressing the heterologous manganese peroxidase allows for efficient conversion of the cellulose-containing biomass feedstock into sugars without costly purification of enzymes. Further, in some embodiments, the cell (e.g., a yeast cell) also ferments the resulting sugar into alcohol (e.g., ethanol and/or butanol). This aspect is particularly advantageous because accumulation of sugars can in some instances act to inhibit the enzymes' activities. By fermenting the sugars into alcohols, the cell (e.g., a yeast cell) increases the overall production and speed of conversion of the cellulose-containing biomass feedstock into sugars and ultimately into alcohols. Thus, in some embodiments, the cell (e.g., a yeast cell) expresses the heterologous manganese peroxidase provided herein during fermentation and/or saccharification, and optionally such that saccharification and fermentation occur simultaneously. Accordingly, provide herein are methods for converting a cellulose-containing biomass feedstock to ethanol by treating the biomass with a cell (e.g., a yeast cell) expressing a heterologous manganese peroxidase. In some embodiments, the cell is a yeast cell. In some embodiments, the cell is a *Saccharomyces cerevisiae*. In some embodiments, the cell is a *Pichia*. In some embodiments, the cellulose-containing biomass feedstock is first converted into sugar, and the resulting sugar is subsequently converted into ethanol. In some embodiments, the cellulose-containing biomass feedstock is corn grain.

Heterologous manganese peroxidases useful for the methods provided herein include native manganese peroxidases from various species of fungus: *Trametes versicolor* (SEQ ID NO:1), *Laccaria bicolor* S238N-H82 (SEQ ID NO:2), *Pleurotus ostreatus* (SEQ ID NO:3), *Lentinula edodes* (SEQ ID NO:4), *Ganoderma applanatum* (SEQ ID NO:5), *Phlebia radiata* (SEQ ID NO:6), *Phanerochaete chrysosporium* (SEQ ID NO:7), *Gelatoporia subvermispora* (SEQ ID NO:8). Heterologous manganese peroxidases useful for the methods provided herein also include improved manganese peroxidases provided herein.

In some embodiments, the cellulose-containing biomass feedstock is first pre-treated to render the cellulose more available to the enzymes. In some embodiments, the feedstock is ground into finer pieces or otherwise treated to increase surface area of the material. In some embodiments, the pre-treatment comprises at least one of the following: acid hydrolysis (see, e.g., U.S. Pat. Nos. 4,174,976 and 5,597,714; and PCT Publication WO/2006/086861), steam explosion (see, e.g., U.S. Pat. No. 6,506,282 and PCT Publication WO/2000/039387), autohydrolysis, ionic liquids (see, e.g., U.S. Pat. No. 6,824,599), hot water, ammonia explosion (see, e.g., U.S. Pat. No. 5,037,663), extrusion (see, e.g., U.S. Pat. No. 7,037,096;), or microwave treatment (see, e.g., U.S. Pat. No. 5,196,069).

In some embodiments, the cellulose-containing biomass feedstock is first pre-treated to render biomass particles having small sizes (e.g., milled). It has been noted that yield of biofuel (e.g., ethanol) can be improved by using biomass particles having small sizes, e.g., biomass particles having a relatively uniform particle size of less than 1600 microns. For example, at least 95% of the pretreated biomass particles have a particle size from about 100 microns to about 800 microns, or a particle size from about 100 microns to about 500 microns. Pretreated biomass particles can be generated by, e.g., a hammer mill or a colloid mill or a shear mill or a cavitation mill; serial combinations of any two or more of these can also be employed. For example, the colloidal mill can be used to select the resulting particle size distribution through the use of gap rotational controls. A relatively precise particle size distribution can be obtained from much larger biomass material using a colloid mill in contrast to alternative pretreatment techniques such as comminution with a hammer mill. An appropriate gap size on the colloid mill can produce a highly uniform suspension of biomass, where the maximum particle size of the biomass is greatly reduced and significantly more uniform compared to using only the comminution device. The radial gap size for a colloidal mill used in a corn ethanol plant can range from 0.104-0.728 millimeters, e.g., from 0.104-0.520 millimeters, e.g., from 0.208-0.520 millimeters, such that the resulting particle sizes are in the range of 100-800 microns. For example, in some embodiments, a gap setting of 0.1-0.15 is used for corn stover or other cellulosic biomass and a gap setting of 0.2-0.3 mm is used for grains including but not limited to corn kernels. As a second example, a shear mill can be used to reduce particle size of cellulose-containing materials under high shear action, especially for fibrous woody material. In shear milling, the material is processed through several generator stages (typically three) of a dispersing device which produces very fine suspensions. The stages consist of rotor-stator combinations to reduce particle size and create a very narrow size distribution from larger-sized woody feedstock material. Various combinations of generators can be used to achieve desired particle size reductions, such as suspensions containing particles in the range of 100 to 300 microns. Techniques for generating biomass particles having small sizes are fully described by, e.g., U.S. Patent Application Publication No. 20100055741, the content of which is incorporated in its entirety herein.

In some embodiments, fermentation temperatures will be controlled between 28-35° C. and pH 4.0-5.5. In some embodiments, a temperature-tolerant yeast cell strain can be used, and accordingly a higher fermentation temperatures can be used (e.g., at or above 35° C., 36° C., 37° C., 38° C., 39° C., or 40° C.). There are other factors affecting enzyme activity (e.g., MnP activity) include surface area, pore volume, pore size distribution of the cellulose-containing biomass feedstock, pretreatment method, the presence or absence of inhibitors such as furfurals, and the presence of various enzyme cofactors (e.g., manganese). Many enzymes require the presence of an additional, nonprotein, cofactor. Some of these are metal ions such as $Ca^{2+}$, $Zn^{2+}$, $Cu^{2+}$, $Mn^{2+}$, $K^+$, and $Na^+$, which are commonly present in biomass. In some embodiments, ligninases and manganese peroxidases will specifically require manganese for generation of hydrogen peroxide. Some cofactors are small organic molecules called coenzymes. The B vitamins thiamine (B1), riboflavin (B2) and nicotinamide are precursors of some coenzymes. Coenzymes may be covalently bound to the protein part (called the apoenzyme) of enzymes as a prosthetic group. Others bind more loosely and, in fact, may bind only transiently to the enzyme as it performs its catalytic act. These are normally present in enough concentration in typical fermentations, however if they are deficient, they can be added to the fermenter in order to enhance the conversion.

In some embodiments, the cellulose-containing biomass feedstock can be used as an inexpensive form of sugar (i.e., for value added products). In some of these embodiments, excess sugar is bled from the saccharification tank(s) (i.e., where the enzymes are converting plant material to sugar), for example using a sequential membrane, filtrate wash, or other sugar removal system. This reduces the sugar concentration in the saccharification tank(s) and allows for hydrolysis to continue without being inhibited by excess sugar. Residual non-sugar producing solids can be optionally purged forward for further processing or for other uses (such as for fuel value in a cogeneration system).

Furfurals can accumulate in some saccharification reactions. Furfurals can in some embodiments act as yeast growth inhibitors. Thus, bacteria that consume furfurals can also be added to the fermentation to selectively reduce or eliminate the furfurals.

In some embodiments, the mixture of yeast cells and the cellulose-containing biomass feedstock are incubated to result in production of sugars from cellulose or other plant material and subsequent fermentation of the sugars into alcohols. Industrial fermentation conditions are known in the art. In some embodiments, a modified form of Simultaneous Saccharification and Fermentation (SSF) can be accomplished by using a small saccharification step in order to produce a small amount of sugar to promote yeast growth. This partially converted media is then sent to the fermenter. After the fermenter volume is approximately 10-20% of the total fermenter volume the yeast inoculum is added. The tank is then continuously filled in a fed batch mode over a period of 25-35 hours and then held at 35° C. until the fermentation is complete (~72 hrs). This allows sufficient use of the sugars to prevent inhibition of the process. To improve alcohol production, yeast strains with a high ethanol tolerance can be selected. In some embodiments, yeast growth stimulants can also be added to the mixture. For example, sterols can be added to stimulate yeast growth and enzyme production.

In some embodiments, the yeasts provided herein are exceptionally efficient for the production of ethanol. However, some of the same yeasts can be used for saccharification without subsequent fermentation. This can be accomplished, for example, by, e.g., allowing the yeasts to generate biomass hydrolysate, limiting ethanol production, followed by deactivation of the yeast so the fluid contains free enzymes and proteins. In the case of yeasts that have the expressed enzymes attached to the surface, the yeasts can be cultivated, deactivated with ultrasound and then used as immobilized enzymes within the saccharification vessel. The yeast can be filtered at the end of the saccharification process along with the other solids in this manner.

In some embodiments, the mixture of yeast cells and the cellulose-containing biomass feedstock are incubated to result in production of biomass-derived intermediates from cellulose or other plant material. As defined herein, the term "biomass-derived intermediate" refers to a carbohydrate intermediate derived from biomass hydrolysis. In some embodiments, the biomass-derived intermediates are simple sugars, e.g., monosaccharides and disaccharides such as glucose, fructose, mannose, and galactose, sucrose, maltose, lactose, cellobiose, and derivatives thereof. In some embodiments, the biomass-derived intermediates are partial hydrolysis or partial depolymerization intermediates, e.g., cellobiose. In some embodiments, the biomass-derived intermediates are non-sugar biomass-derived intermediates. In some embodiments, the non-sugar biomass-derived intermediates are polyols, e.g., sorbitol, anhydrosorbitol, glycerol, and propanediol. In some embodiments, the non-sugar biomass-derived intermediates are isomerization and dehydration products derived from biomass hydrolysis and fermentation process, e.g., "reversion products," "acyclic intermediates," and "fructofuranosyl intermediates" as described in Chheda et al., *Angew. Chem. Int. Ed.* 46:7164-7183, 2007. In some embodiments, the non-sugar biomass-derived intermediates are additional dehydration and fragmentation products of acyclic intermediates and fructofuranosyl intermediates as described in Chheda et al., *Angew. Chem. Int. Ed.* 46:7164-7183, 2007. In some embodiments, the non-sugar biomass-derived intermediates include furans, e.g., furfural, 5-hydroxymethylfurfural, di-formylfuran, and derivatives thereof (e.g., 2,5-funandicarboxylic acid, di(hydroxymethyl)tetrahydrofuran, methyl tetrahydrofuran). Additional examples of biomass-derived intermediates are known in the art and disclosed in Chheda et al., *Angew. Chem. Int. Ed.* 46:7164-7183, 2007. In some embodiments, the non-sugar biomass-derived intermediates are amino acids and organic acids, such as levulinic acid, formic acid, fumaric acid, aspartic acid, succinic acid, malic acid, 3-hydroxypropionic acid, aspartic acid, itaconic acid, glutamic acid, glucaric acid, gluconic acid. If desired, any of the above products (i.e., sugar biomass-derived intermediates or non-sugar biomass-derived intermediates) can be further purified from the remainder of the reaction mixtures and/or chemically or enzymatically converted to yet another desired product.

The activity or amount of substrate hydrolysis of the improved manganese peroxidases described herein can be determined either directly or indirectly. Examples of direct measurements include activity assays such as the MBTH/DMAB assay described in Example 1. The improved activity can also be determined by measuring the amount of carbohydrates produced by enzymatic treatment of cellulosic biomass using an improved manganese peroxidase described herein. In some embodiments, the improved activity can be determined indirectly, such as by measuring a secondary product resulting from the digestion of lignocellulosic biomass. Examples of secondary products include ethanol, inhibitors and phenolic compounds, and sugar and non-sugar biomass-derived intermediates.

As is well understood in the art, the production of ethanol is dependent on the properties of individual yeast strains. Further, the properties of individual yeast strains can change over time and under different culture conditions. Thus, two yeast strains derived from the same parental strain can produce different amounts of ethanol or convert sugars to ethanol at different rates under the same culture conditions. These differences between strains can be due to changes that are independent of the mutations described herein, such that the amount of ethanol obtained during fermentation can result from efficient glucose to ethanol conversion that is due to strain genetics and/or increased MnP activity.

In some embodiments, the amount of substrate hydrolysis by an improved manganese peroxidase can be determined indirectly by measuring the carbohydrate composition remaining after a fermentation reaction. For example, in some embodiments, there is a decrease in the amount of carbohydrates that are derived from cellulose and hemicellulose in the post-fermentation sample when the biomass is fermented with yeast expressing an improved manganese peroxidase. As described in the examples, a decrease in carbohydrates in the post-fermentation carbohydrate composition indicates that more complex carbohydrates, such as glucan and xylan, were converted to fermentable sugars glucose and xylose, which serves as an indirect way to determine the activity of the improved manganese peroxidases described herein. Thus, in some embodiments, the improved manganese peroxidases described herein disrupt lignin to produce better access to cellulose and hemicellulose by enzymes that convert carbohydrates into fermentable sugars.

In some embodiments, the activity of the improved manganese peroxidases described herein can be determined by measuring the amount of byproducts of lignin hydrolysis. For example, in some embodiments, the byproducts of lignin hydrolysis are inhibitors and/or phenolic compounds. Thus, in some embodiments, the amount of inhibitors and/or phenolic compounds produced during fermentation are decreased at a greater rate by yeast expressing an improved manganese peroxidase described herein. In some embodiments, the inhibitors syringaldehyde and ferulic acid are decreased at a greater rate when biomass is fermented with yeast expressing an improved manganese peroxidase described herein.

EXAMPLES

The following examples are offered to illustrate, but not limit the claimed invention.

Example 1

Manganese Peroxidase Functional Assay

A 50 mM MBTH stock solution (stored at 4° C.) was made by dissolving 58.43 mg MBTH (FW=233.72) in 5 ml 500 mM Lactic acid buffer (pH 4.5). 1 mM MBTH working solution stored at 4° C., kept no longer than a week) was then made using 50 mM stock solution. 50 mM DMAB (stored at room temperature, kept no longer than a month) was made by dissolving 49.557 mg DMAB (FW=165.19) in 6 ml ethanol. 10 mM working solution (stored at room temperature, kept no longer than a week) was then made using 50 mM stock solution. 10 mM $MnSO_4$ (stored at 4° C., kept no longer than a month) was made by dissolving 67.608 mg $MnSO_4$ (FW=169.02) in 40 ml water. 1 M succinic lactic acid buffer was made by dissolving 40.51 g succinic acid disodium (FW=162.05) in 250 ml water, with pH adjusted to 4.5 using lactic acid.

Water at 590 nm was used as blank for the spectroscopy. 2 ml reaction solution was made by mixing 800 µl 1 M succinic lactic acid buffer, 198 µl 10 mM DMAB, 140 µl 1 mM MBTH, 60 µl 10 mM $MnSO_4$, 115 µl 3% hydrogen peroxide, manganese peroxidase, yeast MnP culture and water. The final concentrations of various components are 0.07 mM MBTH, 0.99 mM DMAB, 0.3 mM $MnSO_4$, 400 mM succinic-lactic acid buffer (pH 4.5), 0.05 mM $H_2O_2$. 115 µl 3% hydrogen peroxide was added at last. Once the hydrogen peroxide was added, the first measurement was taken immediately (time zero). Additional measurements were taken at following time points: 0, 5, 10, 20, 30, and 60 minutes.

Example 2

Mutant MNP Corn Mash Fermentation

Abbreviations: 4° C.=4 degrees Celsius; ANOVA=Analysis of Variance Analysis; C/Htec=Ctec and Htec; Ctec=Enzyme mix sold by Novozymes (Cellic Ctec); Htec=Enzyme mix sold by Novozymes (Cellic Htec); DMAB=3-(dimethylamino)benzoic acid; FAE=Ferulic Acid Esterase; FW=Formula Weight; $H_2O_2$=Hydrogen Peroxide; HPLC=High Performance Liquid Chromatography; HSD=Honestly Significant Difference; M=Molar; MBTH=3-methyl-2-benzothiazolinone hydrazone; mg=Milligram; ml=Milliliter; mM=Millimolar; MnP=Manganese Peroxidase; Mnptv=Manganese Peroxidase from *Trametes versicolor*; $MnSO_4$=Manganese Sulfate; nm=Nanometer; PCR=Polymerase Chain Reaction; pH=Potential of Hydrogen; Spec=Spectrophotometer; µl=Microliter; XR=Yeast strain sold by North American Bioproducts Corporation (NABC).

Introduction and Experimental Design: A corn fermentation was set up using corn mash milled as described in U.S. Patent Application Publication No. 20100055741 and unmilled corn mash to test the effects of MnP mutants without flag-tag. Initial mutagenesis work was done using MnP with a flag tag, so that expression can be checked via a western blot. Since flag tagged proteins are known to have decreased protein activity, subsequently yeast strains having a MnP without the flag tag were created to obtain yeast with improved MnP activity. Two MnP mutants, yEdQ318 (comprising N107S/H109L/N111L/W278A) and yEdQ324 (comprising D57K/N107S/H109L/N111L/Q152A), were chosen for the screening. For each of yEdQ318 and yEdQ324, a PCR product was obtained by pooling all colonies on the plate respectively. Yeast strains having a MnP without the flag tag were created for yEdQ318 and yEdQ324. MnP activity was tested using MBTH/DMAB assay. Based on this assay, three strains were used in corn fermentation, yEdQ464, yEdQ481, and yEdQ486. Information for each strain is below:

yEdQ464=parental is yEdQ324, site of integration unknown.

yEdQ481=parental is yEdQ318, site of integration is Tau3 site.

yEdQ486=parental is yEdQ324, site of integration is Tau3 site.

Figure 3:
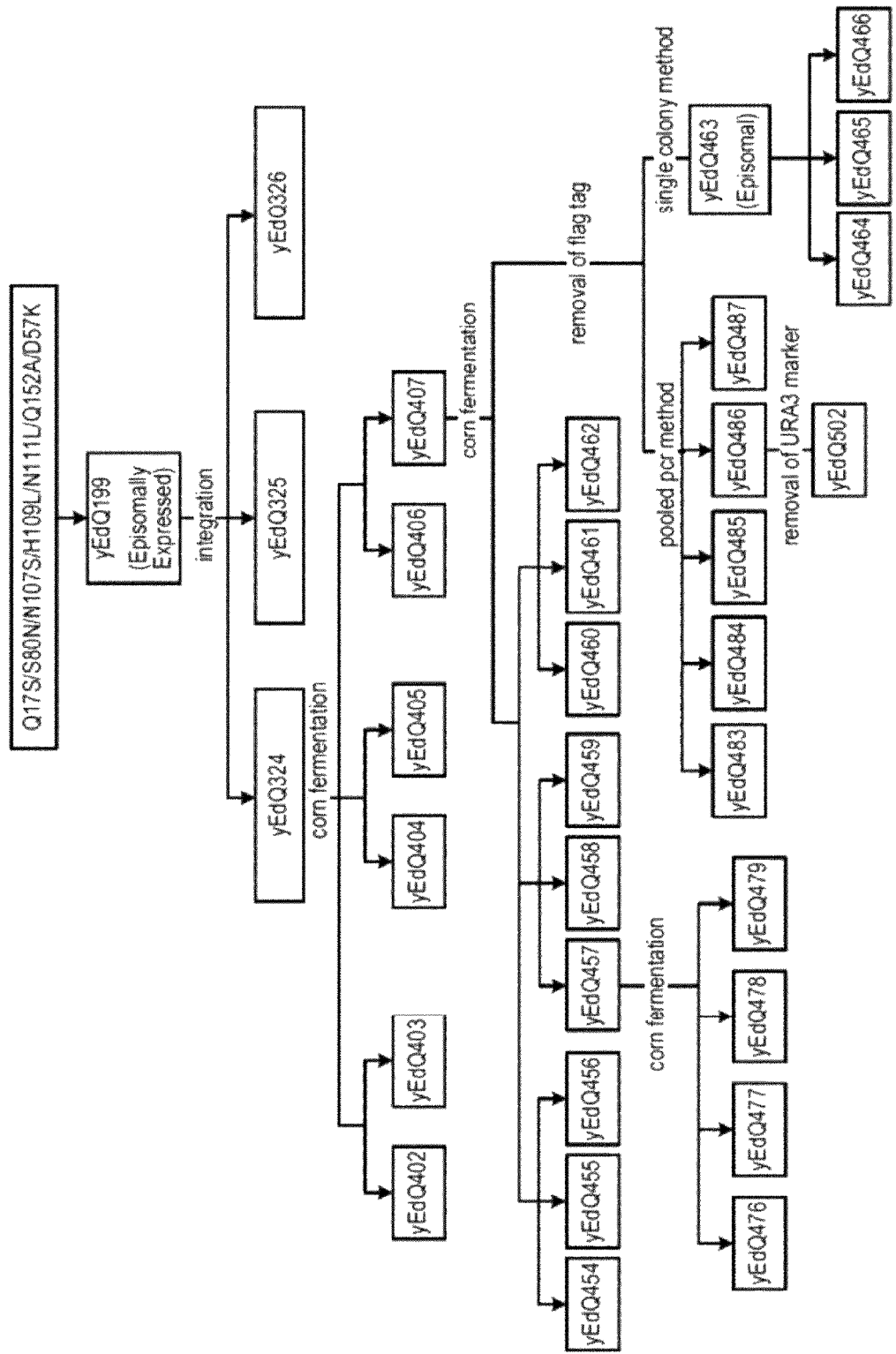
FIG. 3 depicts evolutionary diagram for mutant yEdQ324. Mutation Q17S/S80N/N107S/H109L/N111L/Q152A/D57K was generated using a site directed mutagenesis kit from Stratagene. The plasmid with the mutation was initially incorporated into bacteria. After sequence was confirmed, the plasmid was transformed into yeast and designated yEdQ199. Next, the mutation was integrated into the yeast genome and three colonies from that transformation were kept, yEdQ324, yEdQ325, and yEdQ326. Randomly, yEdQ324 was chosen to be tested in corn. This corn fermentation was done in triplicate. A sample of corn mash from each flask after the fermentation was obtained and streaked onto media plate for growth. Colonies collected thereafter were denoted as being adapted. Adaptation is defined as exposing the yeast to a specific environment and allowing it to react accordingly. Additional corn fermentation experiments were conducted with different adapted versions of yEdQ324. Next, genomic sequence from yEdQ407 was used for flag tag removal. Flag tag removal was done via PCR. The sequence from PCR was incorporated into an in house vector. In parallel to finding a single colony that transformed the sequence correctly, many colonies were pooled together, and desired sequence was amplified. The amplified product was then integrated into the yeast genome. yEdQ483 through yEdQ487 was obtained using the pooled PCR method and yEdQ464 through yEdQ466 was obtained using the single colony method. Lastly, the genomic background of yEdQ486 was used for URACIL 3 marker removal, designated yEdQ502.

Sequencing was evaluated for yEdQ481 and yEdQ486. Based on the sequencing information, yEdQ481 does represent N107S/H109L/N111L/W278A and yEdQ486 has two additional mutations not originally created. yEdQ486 and all strains derived from yEdQ324 have the following MnP mutations, D57K/Q17S/S80N/N107S/H109L/N111L/Q152A. Evolutionary diagram for mutant yEdQ318 is shown in FIG. 2, and evolutionary diagram for mutant yEdQ324 is shown in FIG. 3.

We hypothesized that yeast strains having a MnP mutant without the flag tag will perform comparable to or better than the parental with a flag tag. The four mutant strains tested were yEdQ324, yEdQ464, yEdQ481, and yEdQ486. Each strain was PCR confirmed for the gene and the site of integration. yEdQ464 has an unknown site of integration for MnP.

All strains were tested in triplicates. Brix for unmilled corn mash was 29.1 with starting total sugars of approximately 36%. Brix for milled corn mash was 29.9 with starting total sugars of approximately 38%. Ctec was added at a loading of 1.5% based on cellulose content. Htec was added at a loading of 0.1% based on total solids. FAE loading was at 0.0086 units per gram of cellulose. Fermentations were performed at a scale of 300 grams of corn mash in a 500 ml flask and were initially inoculated with 25 million cells per gram. The temperature profile of this fermentation was 34° C. for the first 24 hours, followed by 32° C. for the remainder of the fermentation. Samples were taken for HPLC at 24, 36, 48, and 64 hours.

Figure 4:
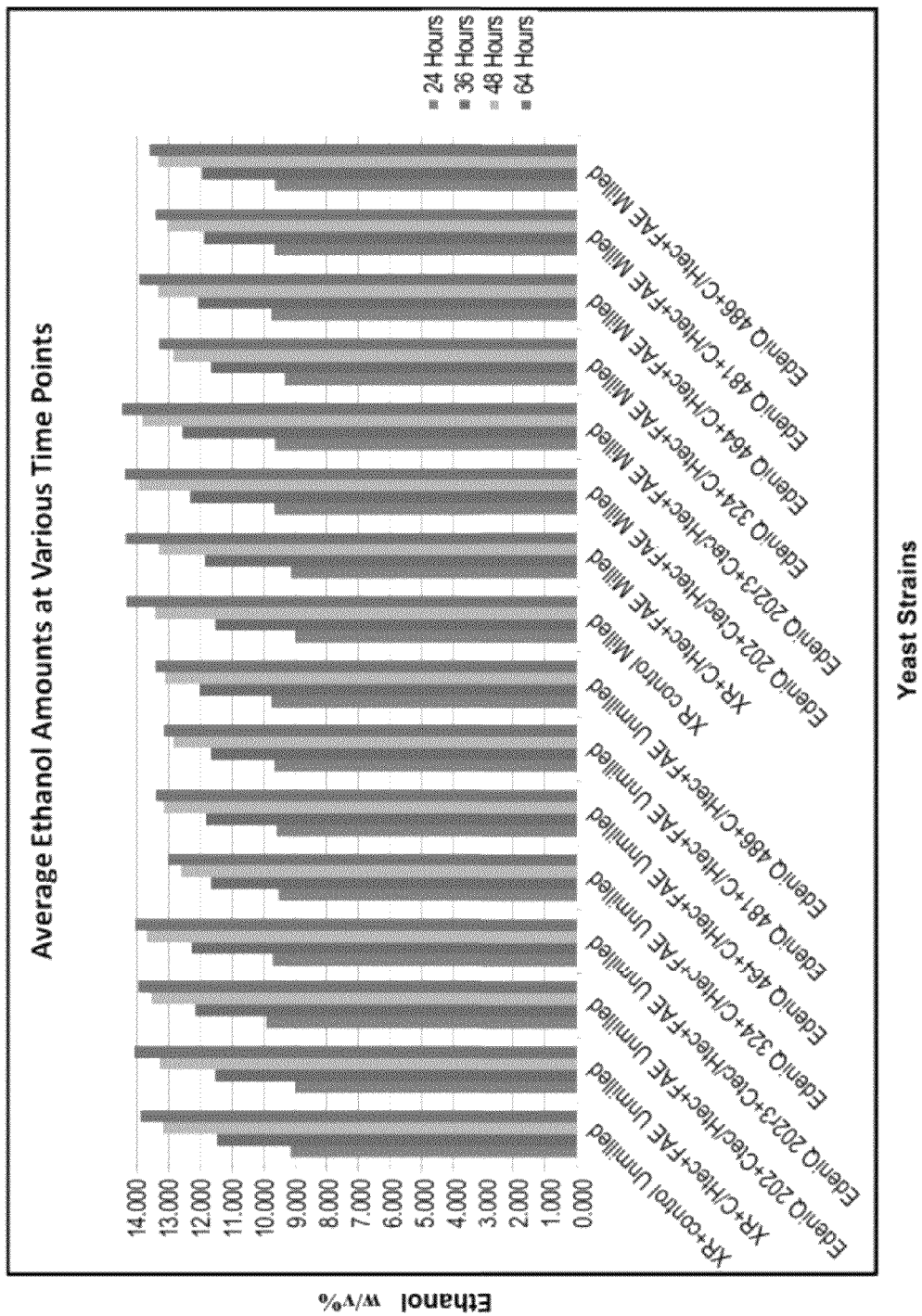
FIG. 4 depicts average ethanol amounts at various time points measured by HPLC. Bio-Ferm XR yeast (NABC) is a commercial yeast strain commonly used for industrial fermentation. FAE is ferulic acid esterase. EdeniQ 202 is wild type *Trametes versicolor* manganese peroxidase (MnP) coding region shown in FIG. 1, integrated into the EdeniQ base *Saccharomyces cerevisiae* yeast strain; the MnP gene product secreted extracellularly. Mutants yEdQ324, yEdQ464, yEdQ481 and yEdQ 486 are MnP mutants as shown in FIG. 3. Ctec/Htec is a commercial cellulase enzyme preparation used with cellulosic biomass for sugar release (Novozymes).
Figure 5:
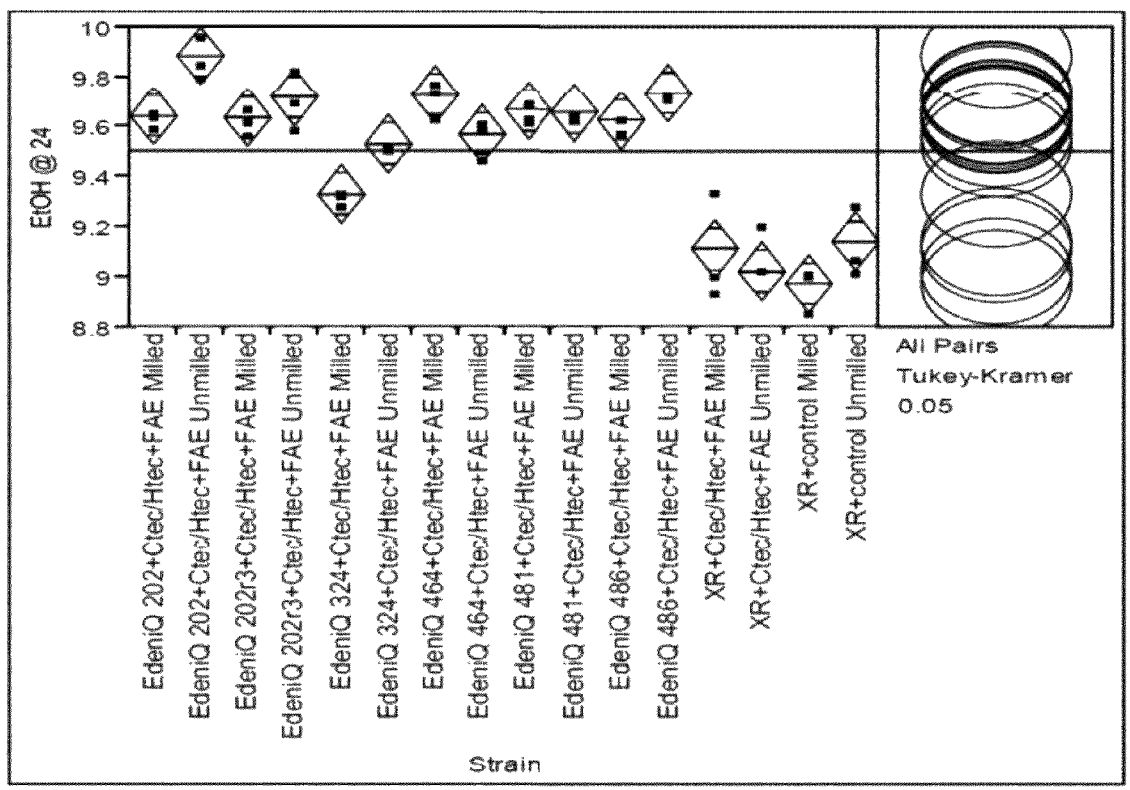
FIG. 5 depicts statistical analysis of average ethanol amounts at 24 hours using ANOVA and the Tukey-Kramer method as a single step multiple comparison procedure to determine significant differences of experimental mean values.
Figure 6:
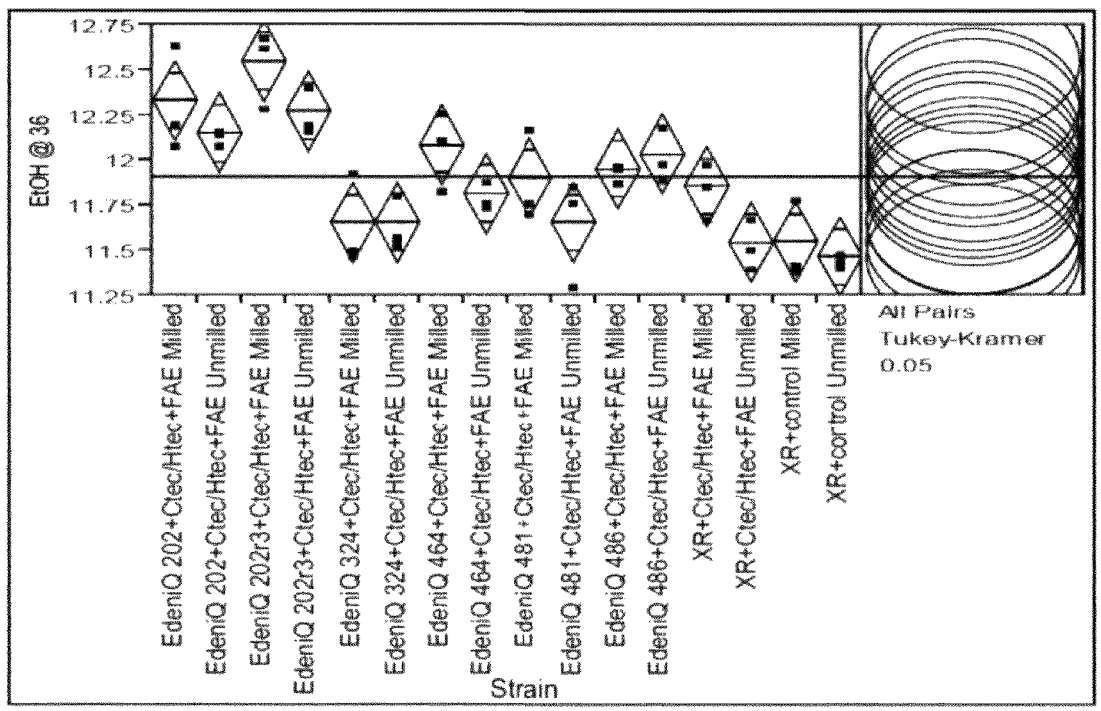
FIG. 6 depicts statistical analysis of average ethanol amounts at 36 hours using ANOVA and Tukey-Kramer method.
Figure 7:
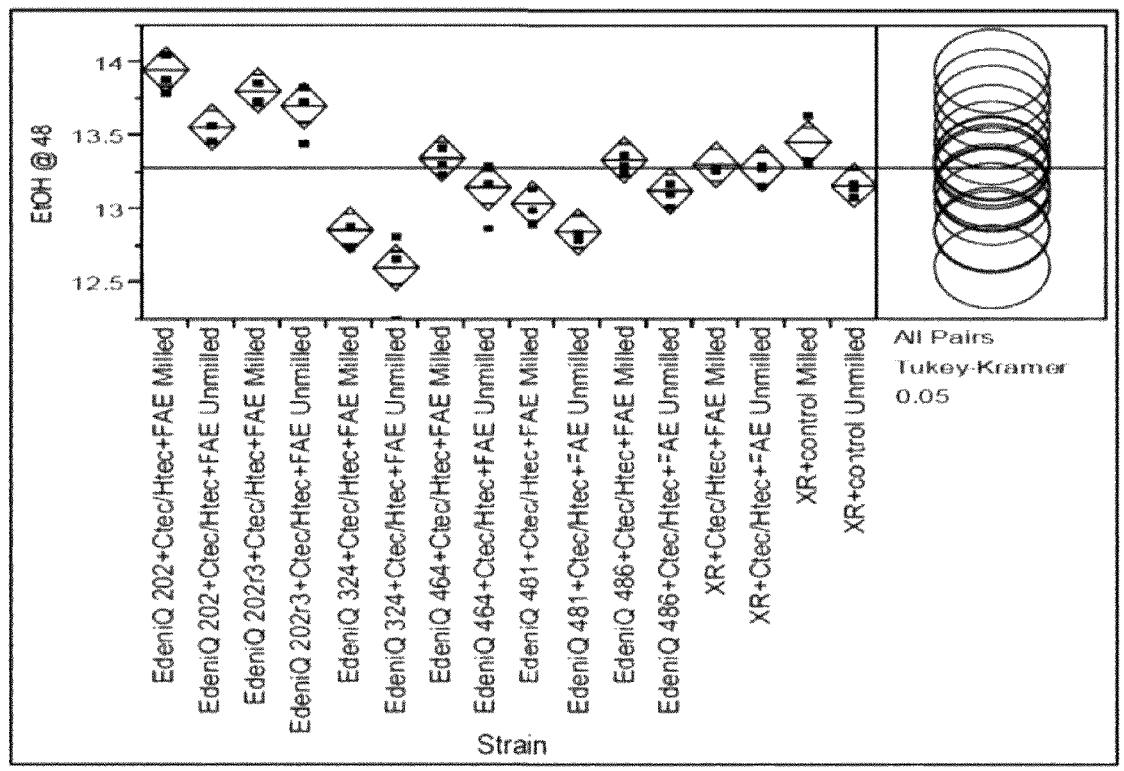
FIG. 7 depicts statistical analysis of average ethanol amounts at 48 hours using ANOVA and Tukey-Kramer method.
Figure 8:
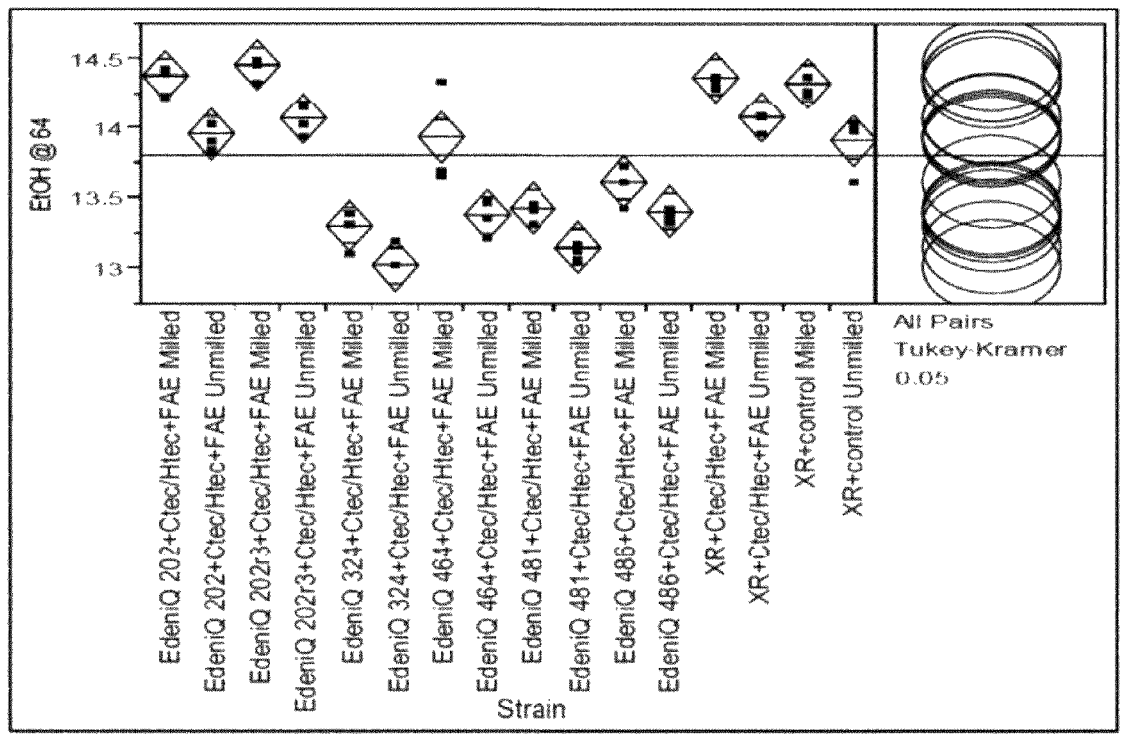
FIG. 8 depicts statistical analysis of average ethanol amounts at 64 hours using ANOVA and Tukey-Kramer method.
Figure 9:
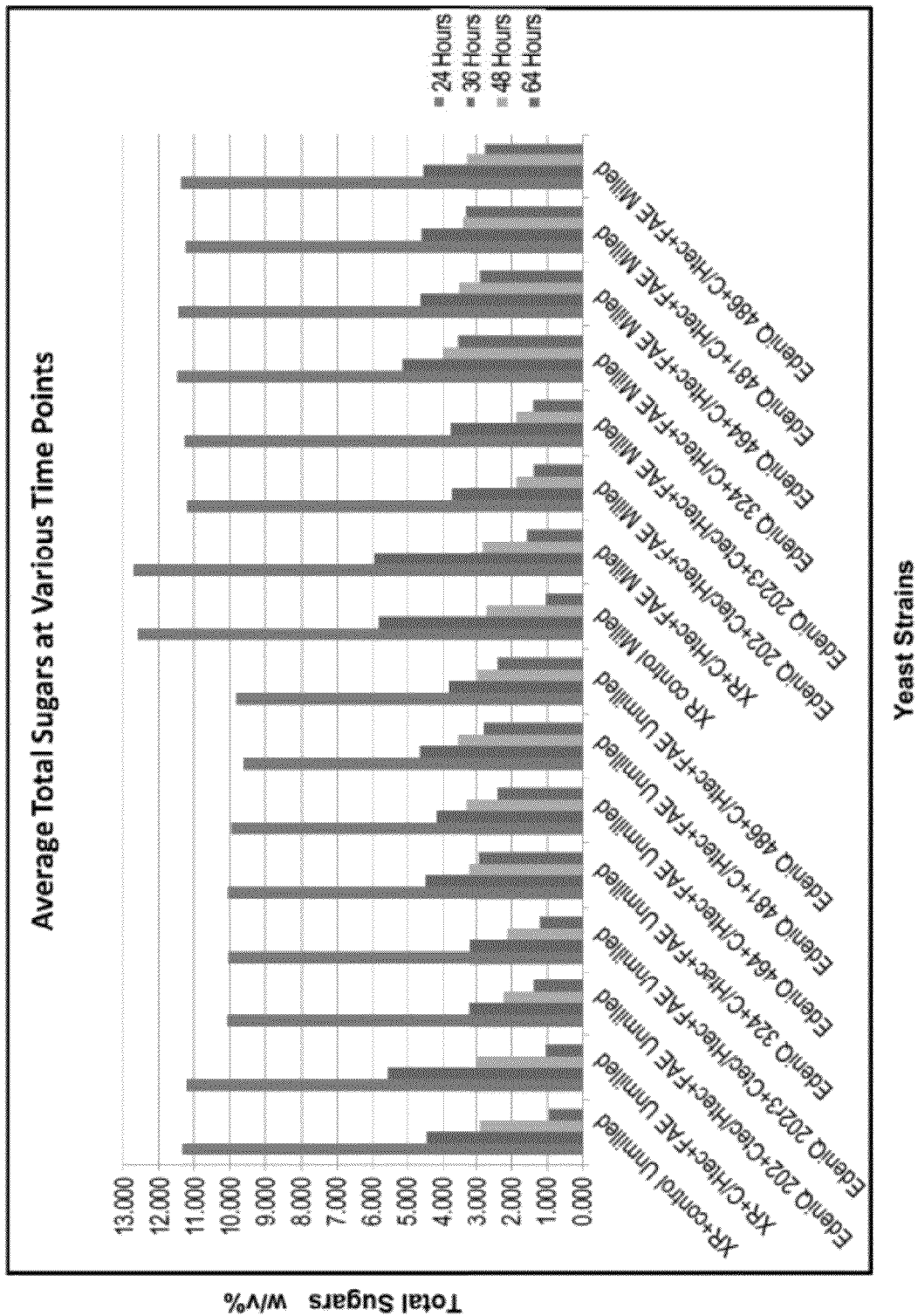
FIG. 9 depicts average total sugars at 64 hours measured by HPLC. Average total sugars values were calculated omitting time zero values, which were comparable among samples, to provide better resolution.
Figure 10:
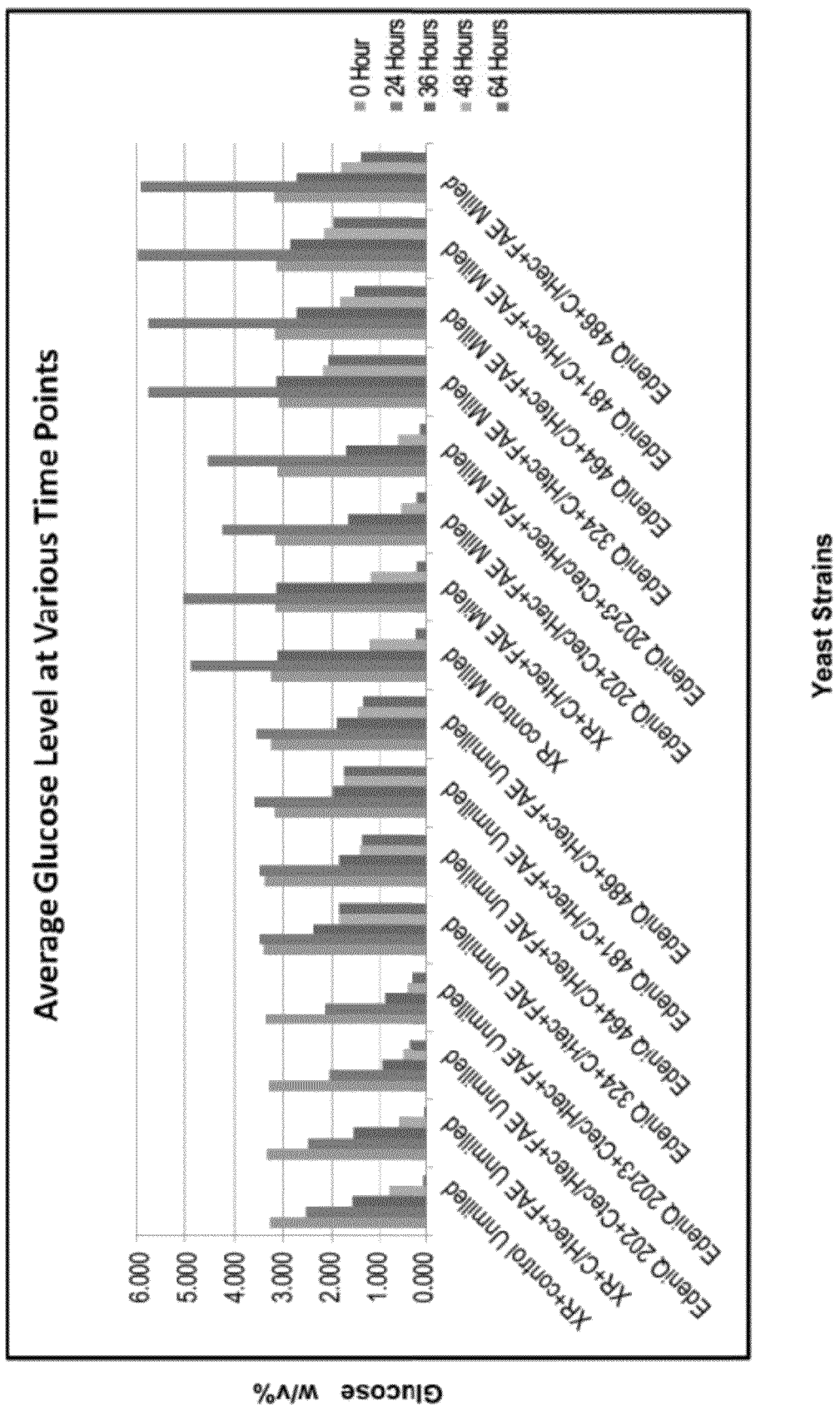
FIG. 10 depicts average total glucose levels at 24, 36, 48, and 64 hours measured by HPLC.
Figure 11:
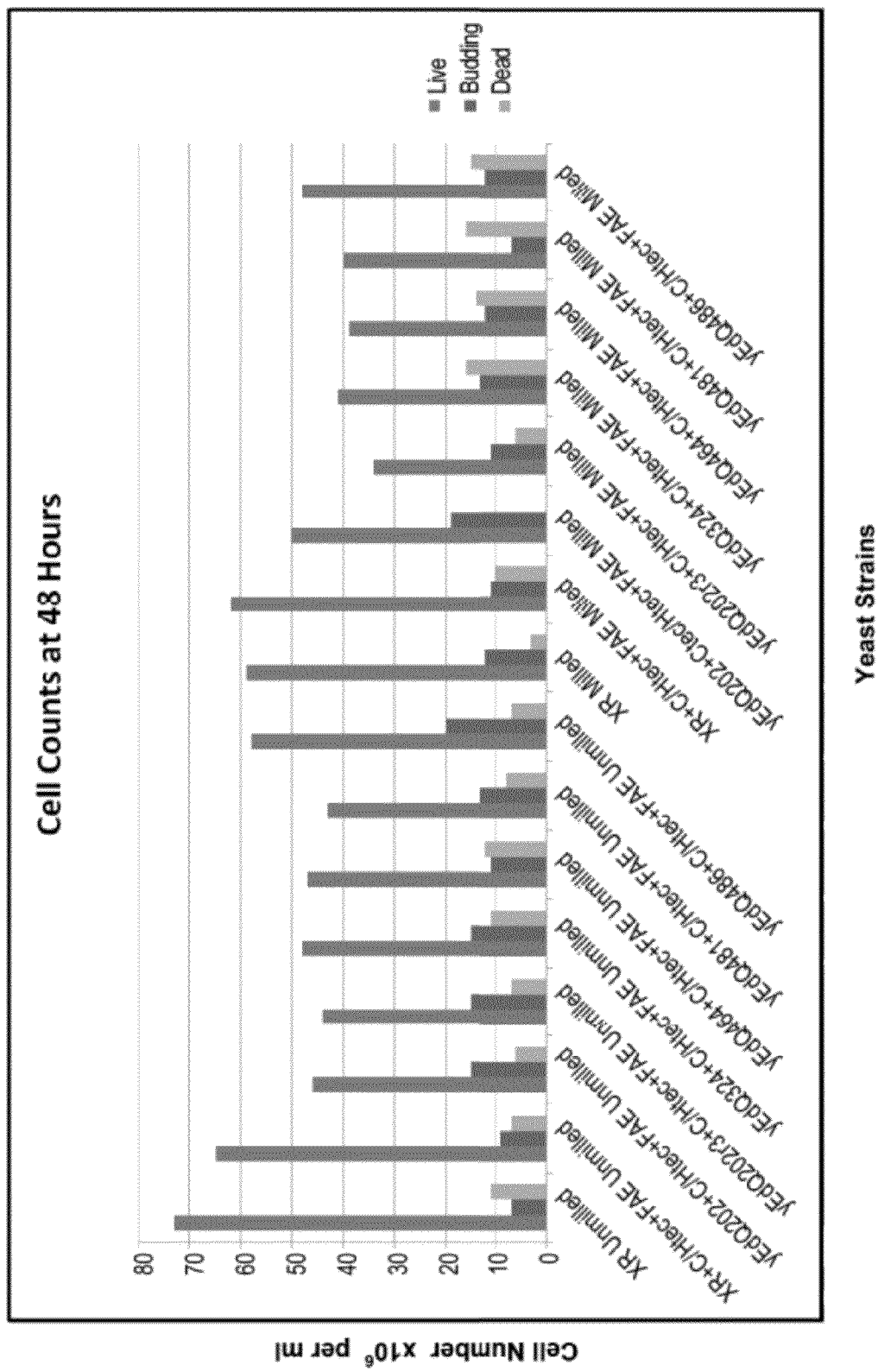
FIG. 11 depicts cell counts at 48 hours measured by hemocytometer counting with viability determination by methylene blue staining.
Figure 12:
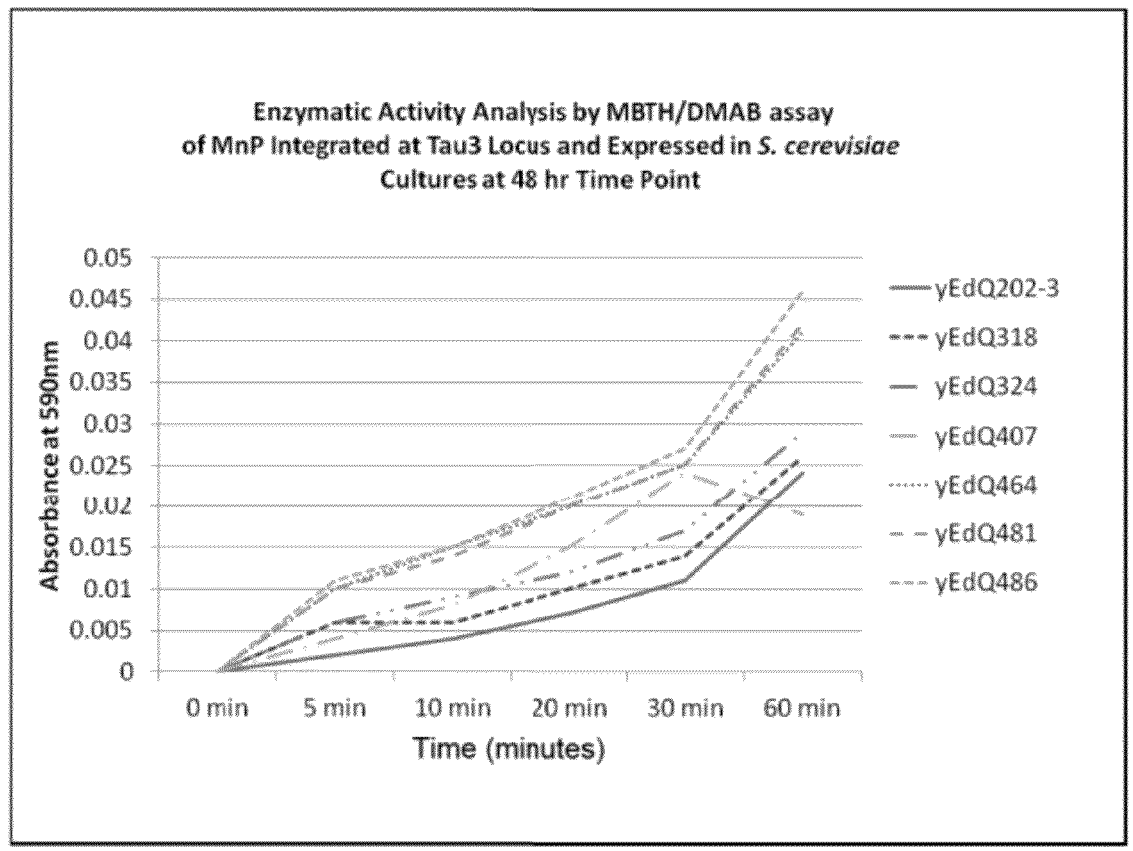
FIGS. 12 and 13 depict data from MBTH/DMAB assay used to test MnP activity as described in Castillo et al., Analytical Biochemistry, 218:399-404, 1994. Analysis was performed at 48 hours (FIG. 12) and 72 hours (FIG. 13) of yeast culture. 24 hour analysis was not conducted, as prior experiments have shown this data to be uninformative. Water was included as baseline control, and shown in FIG. 13 for the 72 hour time point. Based on these graphs, yEdQ464, yEdQ481, and yEdQ486 show greater activity than the parental yEdQ324, and the wild type, yEdQ202-3.
Figure 13:
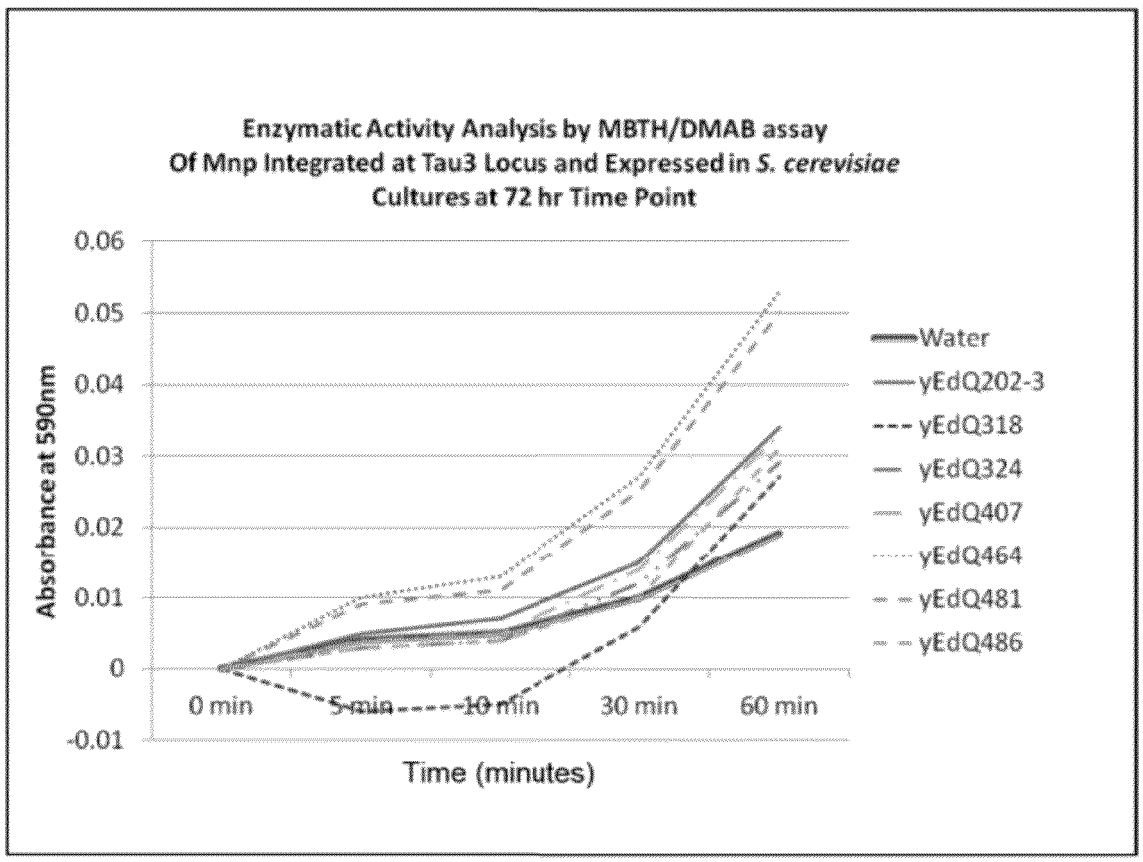
Figure 14A:
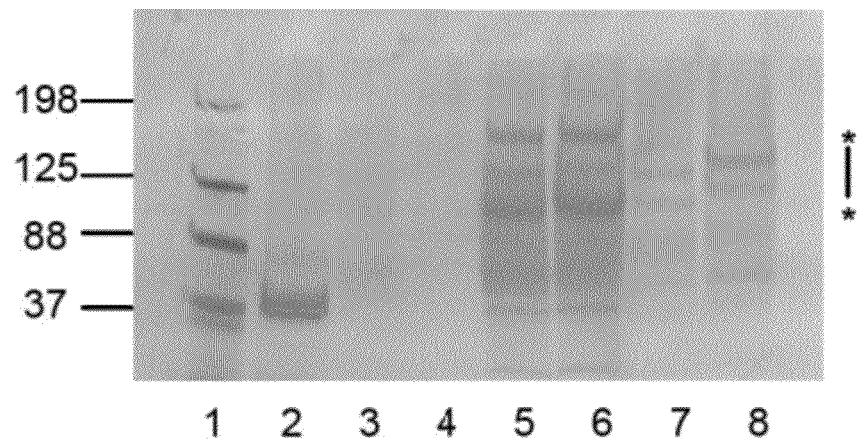
FIG. 14A depicts MnP expression from *Saccharomyces cerevisiae*. Wild type (yEdQ202) and mutant (yEdQ407) MnP expression from *Saccharomyces cerevisiae* detected by Western analysis of cell culture supernatant using a MnP-epitope custom synthesized polyclonal antiserum. Lane 1. Markers annotated in KDa to left; Lane 2. MnP control (Jena Biosciences); Lane 3. yEdQ202, medium; Lane 4. yEdQ407, medium; Lane 5. yEdQ202 medium concentrated 30-fold, 10 ul load; Lane 6. yEdQ202 medium concentrated 30-fold, 20 ul load; Lane 7. yEdQ407 medium concentrated 30-fold, 10 ul load; Lane 8. yEdQ407 medium concentrated 30-fold, 20 ul load. MnP expressed from yeast migrates at a higher apparent molecular weight than the control MnP due to extensive glycosylation (noted as stars). MnP identity is confirmed by treatment with deglycosylation enzyme and subsequent Western blotting with anti-MnP serum.

Results: Average ethanol amount at 24, 36, 48, and 64 hours can be seen in FIG. 4. Maximum ethanol amount after 64 hours was seen in yEdQ202r3+C/Htec+FAE in milled corn mash. FIGS. 5, 6, 7, and 8 represent the different MnP strains, plus their respective triplicates at 24, 36, 48, and 64 hours. Milled and unmilled data was separated for this analysis because the high standard deviation of the combined data would skew results. An ANOVA and Tukey-Kramer HSD analysis with an alpha of 0.05 was compiled for 24, 36, 48 and 64 hours. Below are results for each time points:

24 Hour Statistical Analysis: Based on the ANOVA data, there was a difference between strains at p-value of <0.0001 with an adjusted r-square of 0.89. Highest amount of ethanol was seen in yEdQ202+C/Htec+FAE in unmilled material at 9.89. Average ethanol amount was 9.50. Lowest amount of ethanol is seen in XR with no enzyme addition in milled material measuring at 8.97.

36 Hour Statistical Analysis: Based on the ANOVA data, there was a difference between strains at p-value of <0.0001 with an adjusted r-square of 0.80. Highest amount of ethanol was seen in yEdQ202r3+C/Htec+FAE in milled material at 12.55. Average ethanol amount was 11.90. Lowest amount of ethanol was seen in XR with no enzyme addition in unmilled material measuring at 11.46. Pair-wise comparison for ethanol amount showed that yEdQ324 in milled material was statistically comparable to yEdQ464, yEdQ481, and yEdQ486 in milled material. Pair-wise comparison for ethanol amount showed that yEdQ324 in unmilled material was statistically comparable to yEdQ464, yEdQ481, and yEdQ486 in unmilled material.

48 Hour Statistical Analysis: Based on the ANOVA data, there was a difference between strains at p-value of <0.0001 with an adjusted r-square of 0.87. Highest amount of ethanol was seen in yEdQ202+C/Htec+FAE in milled material at 13.95. Average ethanol amount was 13.29. Lowest amount of ethanol was seen in yEdQ324+C/Htec+FAE in unmilled material measuring at 12.61. Pair-wise comparison for ethanol amount showed that yEdQ464 and yEdQ486 in milled material were statistically better than yEdQ324 in milled material. Amongst each other, they are statistically comparable. yEdQ481 was comparable to yEdQ324. Pair-wise comparison for ethanol amount showed that yEdQ464 and yEdQ486 in unmilled material were statistically better than yEdQ324 in unmilled material. Amongst each other, they were statistically comparable. yEdQ481 was comparable to yEdQ324.

64 Hour Statistical Analysis: Based on the ANOVA data, there was a difference between strains at p-value of <0.0001 with an adjusted r-square of 0.90. Highest ethanol amount was seen in yEdQ202r+C/Htec+FAE in milled material at 14.46. Average ethanol amount was 13.80. Lowest amount of ethanol was seen in yEdQ324+C/Htec+FAE in unmilled material measuring at 13.02. Pair-wise comparison for ethanol amount showed that yEdQ464 in milled material was statistically better than yEdQ324 in milled material. yEdQ481 and yEdQ486 is comparable to yEdQ324. Pair-wise comparison for ethanol amount showed that yEdQ324 in unmilled material was statistically comparable to yEdQ464, yEdQ481, and yEdQ486 in unmilled material.

Conclusion: At 64 hours, yEdQ464 was statistically better than the parental yEdQ324 in milled material, in regards to ethanol production. A Tukey-Kramer HSD method was used in this example. Other tests, however, may be used.

yEdQ481 is comparable to yEdQ324, however, yEdQ481's parental is yEdQ318, so this observation is consistent with prior corn fermentations experiments in which yEdQ324 was shown to perform better than yEdQ318.

Example 3

Mutant MNP Corn Stover Fermentation

Abbreviations: 40° C.=40 degrees Celsius: Ctec2=Enzyme mix sold by Novozymes (Cellic Ctec); Htec2=Enzyme mix sold by Novozymes (Cellic Htec); Mnp=Manganese peroxidase; HPLC=High Performance Liquid Chromatography; ANOVA=Analysis of Variance; HSD=Honestly Significant Difference; ml=milliliter; YPDC=Yeast Peptone Dextrose with Chloramphenicol; ppm=Parts Per Million; HPHT=High Pressure High Temperature; XR=Yeast strain sold by North America Bioproducts Corporation (NABC); C6=Six Carbon Sugars; 4 HBA=4-hydroxybenzoic acid.

Introduction and Experimental Design: A corn stover fermentation was performed to test the efficacy of manganese peroxidase (Mnp) expressing yeast strains described herein on lignocellulosic material. One model for Mnp action is that lignin disruption by Mnp increases access to cellulose and hemicellulose for higher sugar release and increased fermentation product. Another model for Mnp action is that Mnp degrades lignin and related intermediates to cause a favorable change in yeast fermentation behavior by decreasing toxic effects of these inhibitors arising generally from biomass pretreatment methods.

Yeast propagation was initially carried out in 100 ml of yeast peptone dextrose with chloramphenicol (ypdc) media containing 8% glucose. The yeast were pelleted, washed with water, and propagated in 50% stover material and 50% ypdc media containing 8% glucose. The 50/50 solution was used for cell adaptation. This is to facilitate transition into a harsher stover fermentation environment. The HPHT corn stover material used for adaptation is the same material used for fermentation. Lactrol and allpen were supplemented at a concentration of 10 parts per million (ppm). The final concentration of glucose was ~7.1%. For inoculation, cells were first counted and then the appropriate amount of liquid was dispensed into tubes. The tubes were spun down, the supernatant removed, and the cells resuspended in 5 milliliters (ml) of water. The yeast was not washed in water in order to minimize potential shearing effects of the biomass.

In-house HPHT milled corn stover material was used for fermentation. After HPHT, the material was saccharified by adding Ctec2 and Htec2 and incubated for ~40 hours to provide nominal sugars for the yeast. Ctec2 was added at a loading of 10% based on cellulose content. Htec2 was added at a loading of 0.5% based on total solids. Total solid was ~13.74%.

The following strains were tested XR, yEdQ202, and yEdQ407. A 50/50 mix of yEdQ202 and yEdQ407 and a negative control containing just corn stover material was used. Fermentations were performed at a scale of 200 grams of corn stover material in a 500 ml flask, in triplicate. A nitrogen source of urea was added at 500 parts per million (ppm) in addition to antibiotics. Cellulosic material was inoculated with 40 million cells per gram cellulosic material. The temperature profile of this fermentation was 34° C. for the first 24 hours, followed by 32° C. for the remainder of the fermentation. Samples were taken for HPLC at 24 and 48 hours. Cell counts were taken at 24 and 48 hours. Fermentation was conducted in corn stover material according to the protocol for corn mash described in Example 2.

Figure 15:
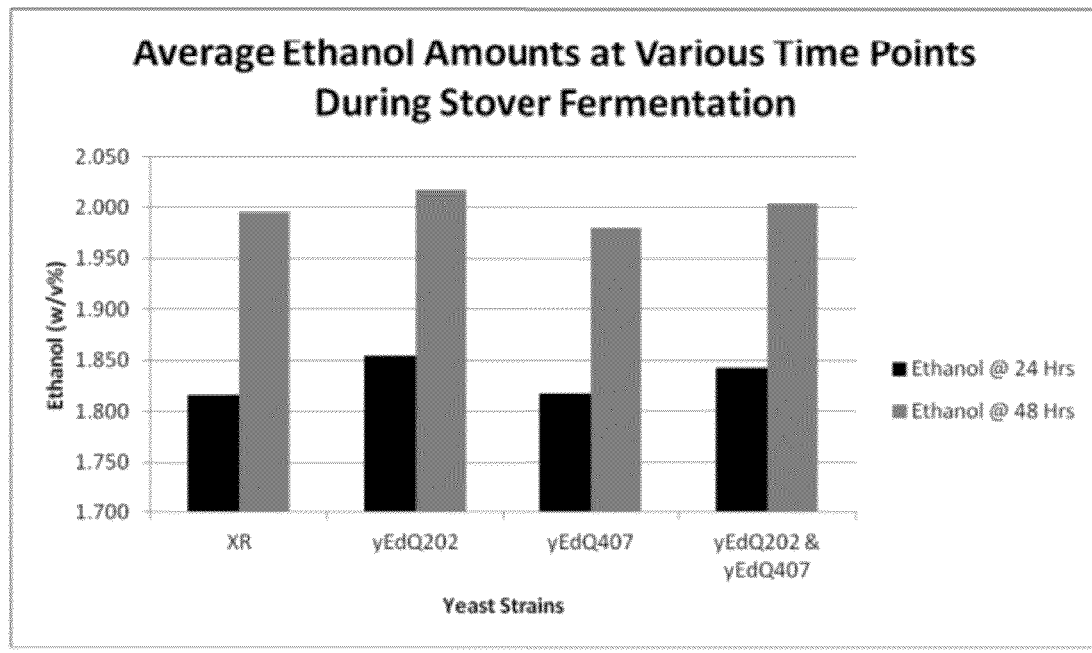
FIG. 15 depicts average ethanol amounts from 20% corn stover solids at 24 hrs and 48 hours fermentation at 32° C. Ethanol levels were measured in w/v % by HPLC. yEdQ202 is wild type MnP secreted from *Saccharomyces cerevisiae*; yEdQ407 is mutant MnP secreted from *Saccharomyces cerevisiae*.
Figure 16:
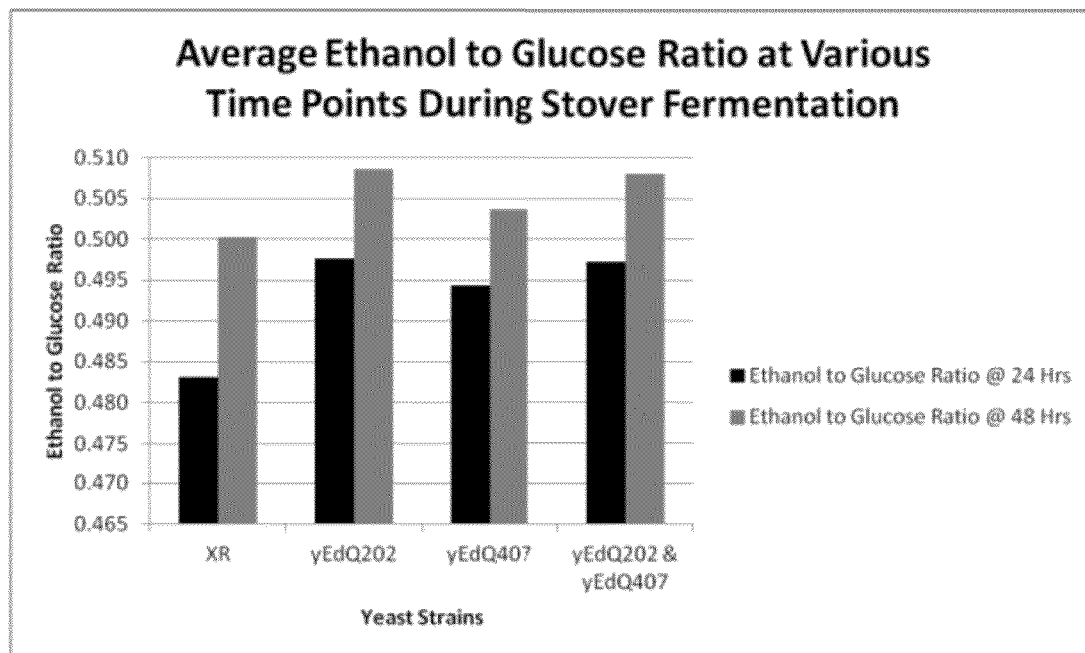
FIG. 16 depicts the glucose to ethanol conversion efficiency at 24 hr and 48 hr stover fermentation for experiment shown in FIG. 15, calculated as the average ethanol to glucose ratio. Fermentation by XR, yEdQ202 and yEdQ407 was performed at 32° C.
Figure 17A:
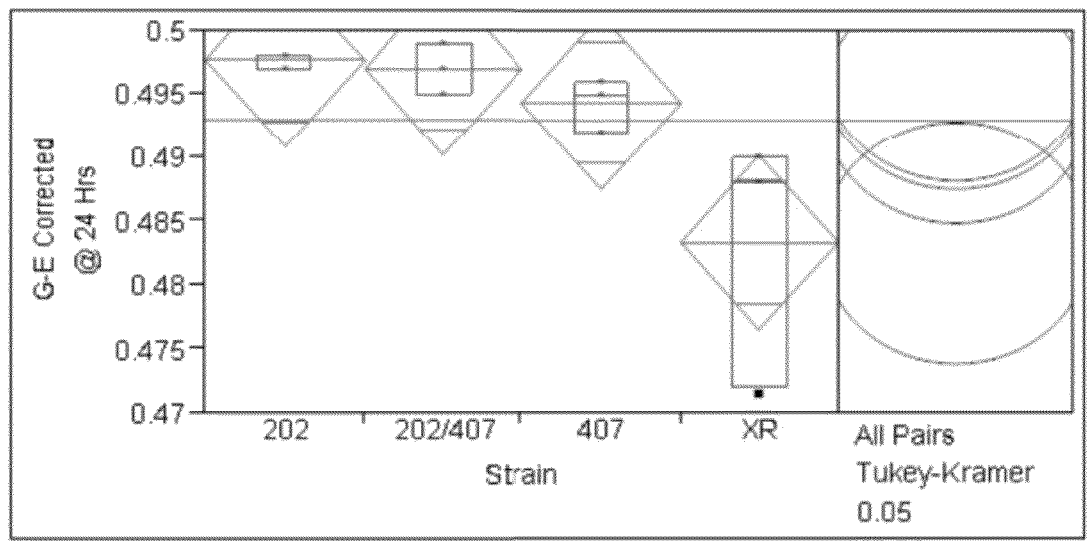
FIG. 17 depicts statistical analysis of average ethanol amounts at 24 hrs (top panel A) and at 48 hours (lower panel B) using ANOVA and Tukey-Kramer method.
Figure 17B:
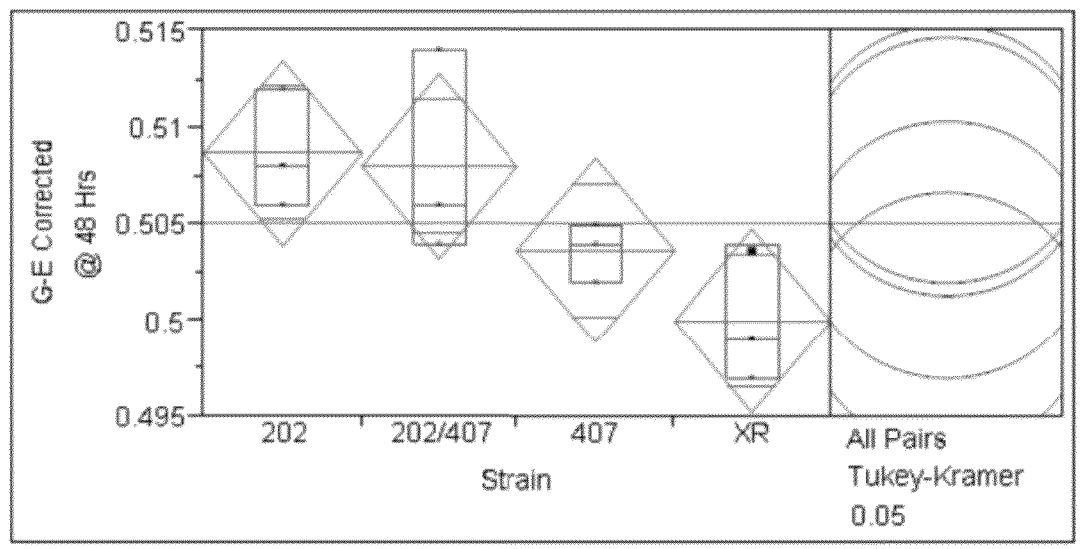

Results: Average ethanol amounts at 24 and 48 hours are shown in FIG. 15. Ethanol amount was corrected for by deducting amounts seen at time 0 from those at 24 and 48 hours. There were no statistically significant differences between strains. In contrast, average glucose to ethanol conversion, shown in FIG. 16, demonstrates significant increased conversion with flasks containing yEdQ202. Average glucose to ethanol conversion is calculated as the ethanol to glucose ratio; corrected values for ethanol were used and final glucose amount seen in the flask containing just corn stover material was used as theoretical maximum. This result is shown in FIG. 17 based on ANOVA and Tukey-Kramer HSD analysis with an alpha of 0.05. Below are the results for each time point:

24 Hour Statistical Analysis: Pair-wise comparison demonstrates that yEdQ202 and yEdQ202+yEdQ407 are statistically better than XR. Pair-wise comparison demonstrates that yEdQ407 is comparable to XR (FIG. 17, upper panel).

48 Hour Statistical Analysis: Pair-wise comparison demonstrates that XR is comparable to all strains (FIG. 17, lower panel).

Figure 18A:
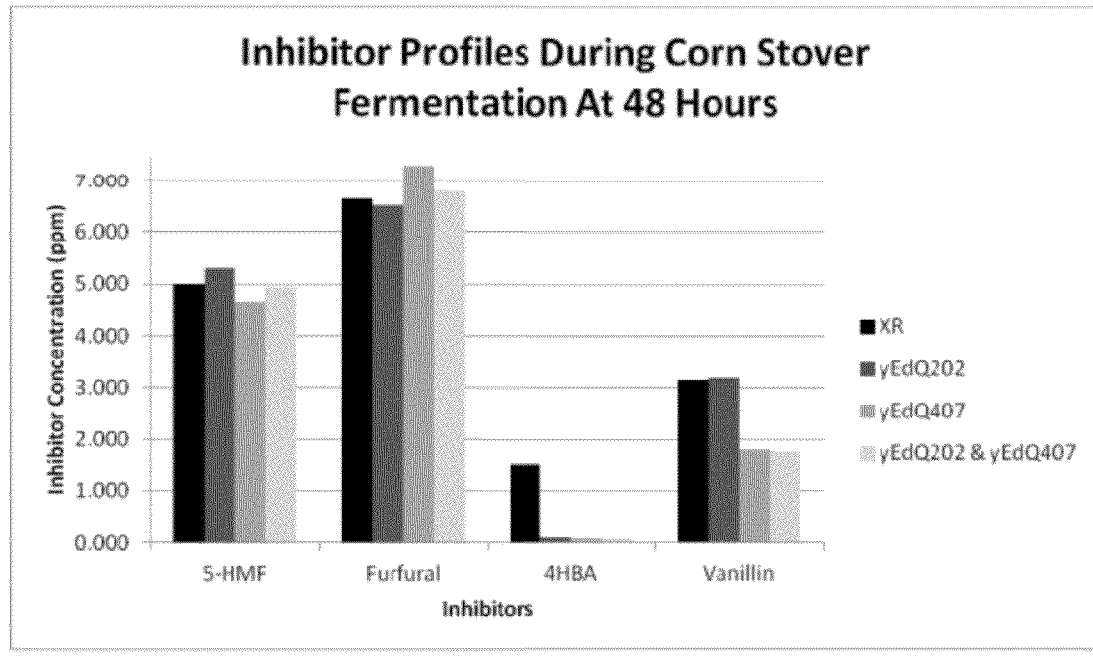
FIG. 18A illustrates 5-HMF, furfural, 4HBA and vanillin levels in ppm for XR control cells, and yEdQ strains 202 and 407.
Figure 18B:
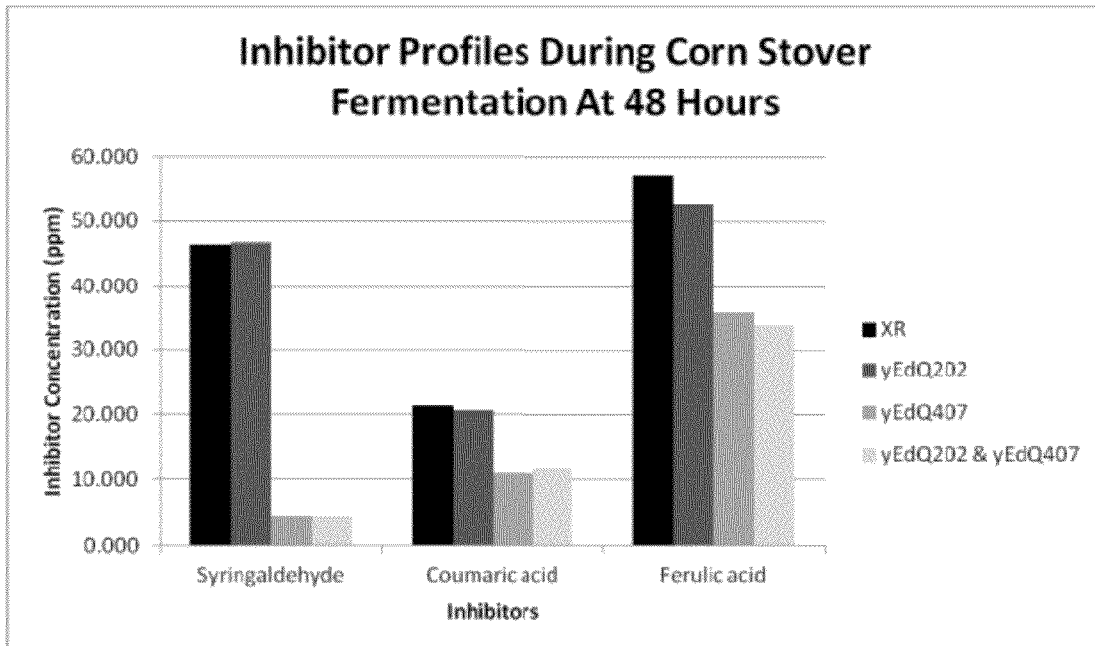
FIG. 18B illustrates syringaldehyde, coumaric acid and ferulic acid levels in ppm.

The concentrations of common inhibitors and phenolic compounds derived from biomass pretreatment were determined by HPLC at various times during fermentation, and the effect of Mnp expressed from yeast described herein is illustrated in FIG. 18A and FIG. 18B at the 48 hours time point Inhibitors with similar concentrations were graphed together for scale equivalence. FIG. 18 shows yEdQ202 decreased 4-HBA at 48 hours of fermentation, whereas yEdQ407 decreased a broader range of inhibitors at 48 hours, including 4-HBA, vanillin, syringaldehyde, coumaric acid and ferulic acid.

Conclusion: Mnp expressing yeast strains performed comparably to control strains in ethanol production. However, glucose to ethanol conversion at 24 hrs of corn stover fermentation by yEdQ202 and the combination of yedQ202/yEdQ407 is significantly higher than the control strain lacking MnP. This supports a model for increased access of cellulose and hemicellulose through disruption of lignin by Mnp. This may underlie a higher rate of glucose utilization at early times. At 48 hours, available glucose is depleted and ethanol production nears its theoretical limit.

Marked differences in inhibitor and phenolic levels were evident between wild type Mnp and mutant Mnp expressed from the yeast described herein. Coumaric acid, ferulic acid and syringaldehyde decreased during fermentation with yEdQ407 after 48 hours. These byproducts are phenolic compounds, which are degradable by Mnp, thus demonstrating enzymatic activity of Mnp. A delayed enzymatic effect is expected because the experiment was designed to remove any remaining growth medium from the cell before inoculation, including residual Mnp, which could have been used for immediate effect. Additionally, Mnp activity is generally detected between 48 and 72 hours after culture; yEdQ202 showing lower activity than yEdQ407, via MBTH/DMAB assay. A decrease in inhibitor and phenolic compounds suggest that Mnp has a detoxifying nature, which may provide protective benefits for yeast.

Example 4

Mutant MNP Corn Stover Fermentation Using Temperature Adapted *Saccharomyces cerevisiae* Yeast Strains Abbreviations: 40° C.=40 degrees Celsius: Ctec2=Enzyme mix sold by Novozymes (Cellic Ctec); Htec2=Enzyme mix sold by Novozymes (Cellic Htec); Mnp=Manganese peroxidase; HPLC=High Performance Liquid Chromatography; ml=milliliter; YPDC=Yeast Peptone Dextrose with Chloramphenicol; ppm=Parts Per Million; HPHT=High Pressure High Temperature; XR=Yeast strain sold by North America Bioproducts Corporation (NABC); DMAB=3-(dimethylamino)benzoic acid; MBTH=3-methyl-2-benzothiazolinone hydrazone; HPHT=High Pressure High Temperature; NREL=National Renewable Energy Laboratory; 5-HMF=Hydroxymethylfurfural.

Introduction and Experimental Design: A corn stover fermentation was performed to determine the effects of manganese peroxidase (Mnp) expressing yeast strains described herein on lignin disruption. Yeast strains described herein are yEdQ622, yEdQ623, and yEdQ747. yEdQ622 and yEdQ623 are Mnp expressing strains that have been adapted to grow at 40° C. and are derived from yEdQ202 and yEdQ407, respectively. yEdQ622 contains a wild type Mnp obtained from *Trametes versicolor*; yEdQ623 contain a mutated version of Mnp from *Trametes versicolor*. The mutated Mnp contains the following amino acid changes: D57K/Q17S/S80N/N107S/H109L/N111L/Q152A. yEdQ747 is a control yeast strain expressing cellobiohydrolase-1 (CBH1) likewise temperature adapted to grow at 40° C. Temperature adaption to 40° C. accommodates efficacy of Ctec2 and Htec2 activity, while promoting yeast viability and fermentation capability.

Figure 19:
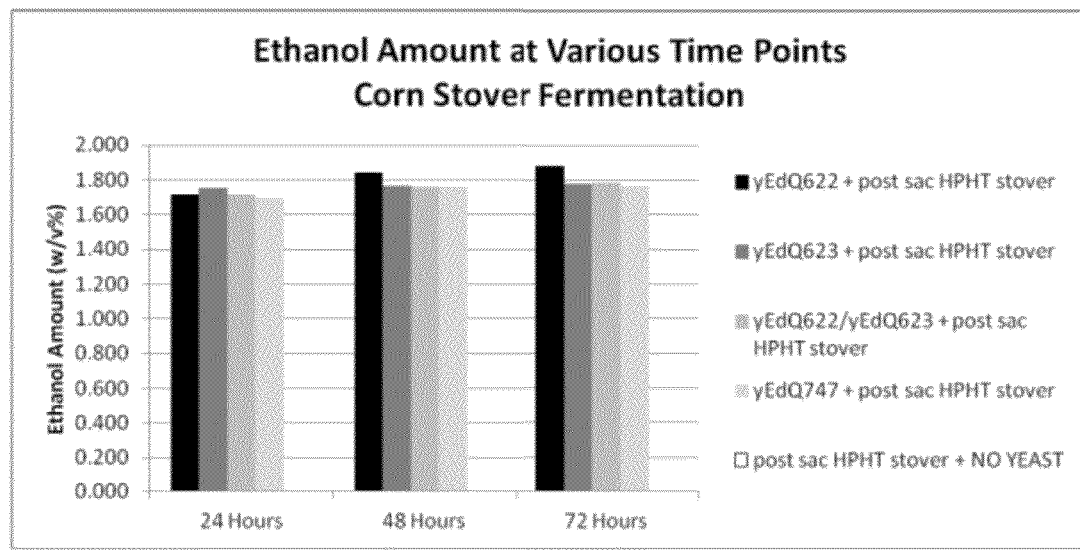
FIG. 19 depicts average ethanol amounts from triplicate samples at 24, 48, and 72 hrs fermentation incubated at 40° C. Ethanol levels were measured in w/v % by HPLC. Residual ethanol was present within inoculum, thus normalization was done by subtracting ethanol amount from time 0. yEdQ622 is the 40° C. temperature adapted strain derived from yEdQ202 expressing wild type MnP. yEdQ623 is the 40° C. temperature adapted strain derived from yEdQ407 expressing mutant MnP. yEdQ747 is a temperature adapted strain expressing cellobiohydrolase I (CBH1).
Figure 20:
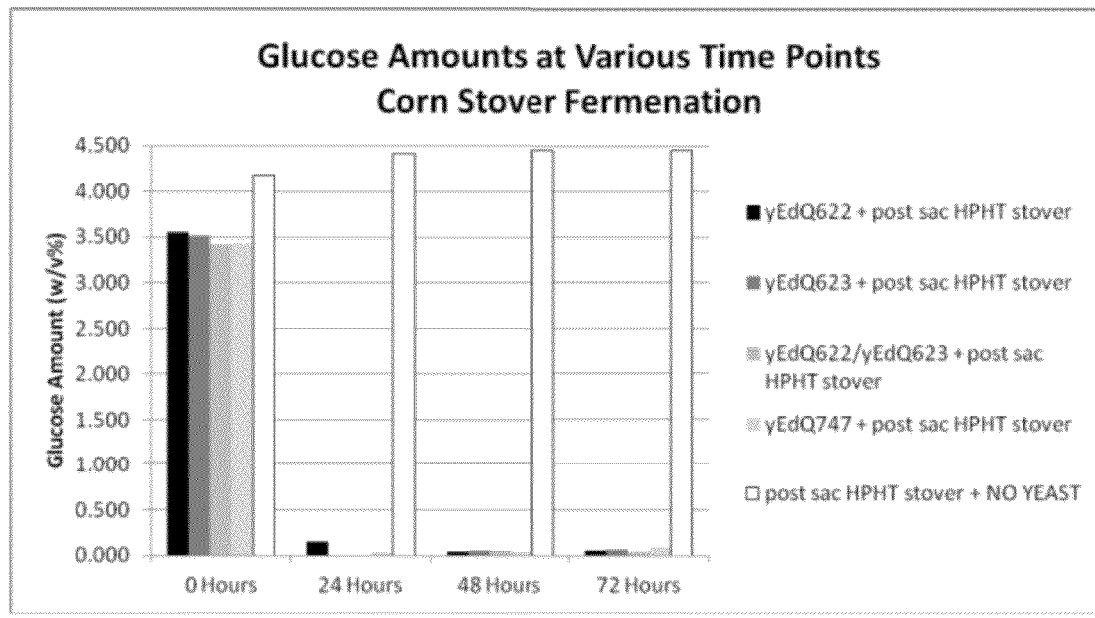
FIG. 20 depicts glucose levels at 0, 24, 48, and 72 hrs tracked by HPLC in corn stover fermentation experiment shown in FIG. 19.
Figure 21A:
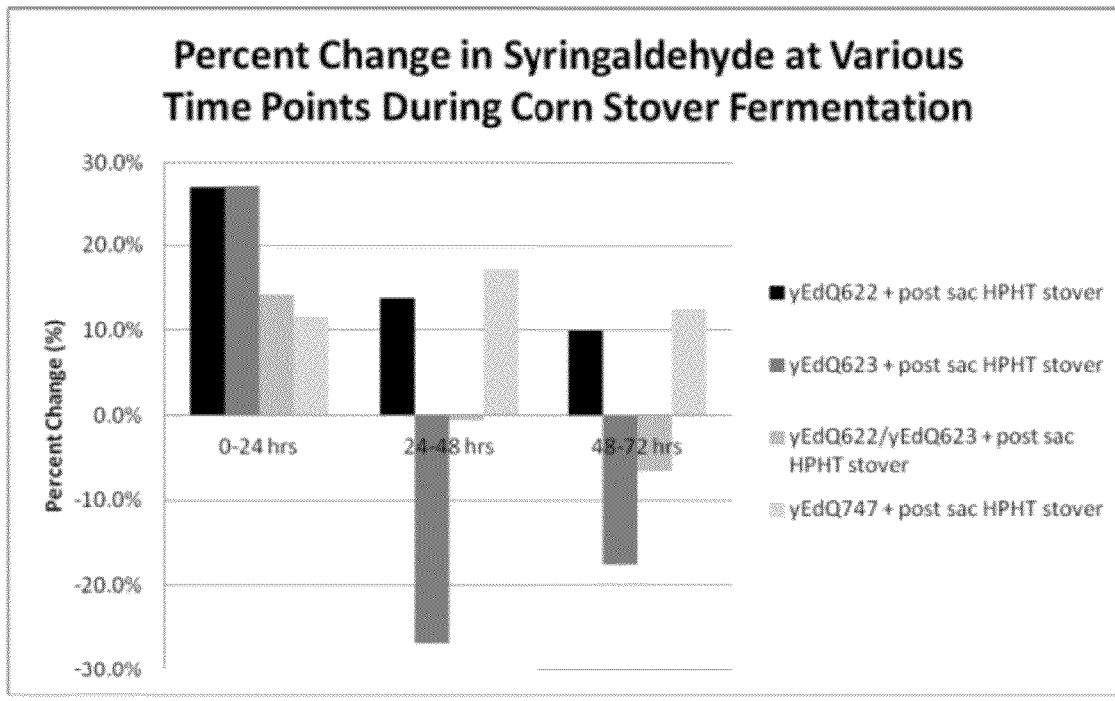
FIG. 21A illustrates syringaldehyde levels in ppm for control yeast strain yEdQ747, yEdQ Mnp-expressing strains 622 and 623.
Figure 21B:
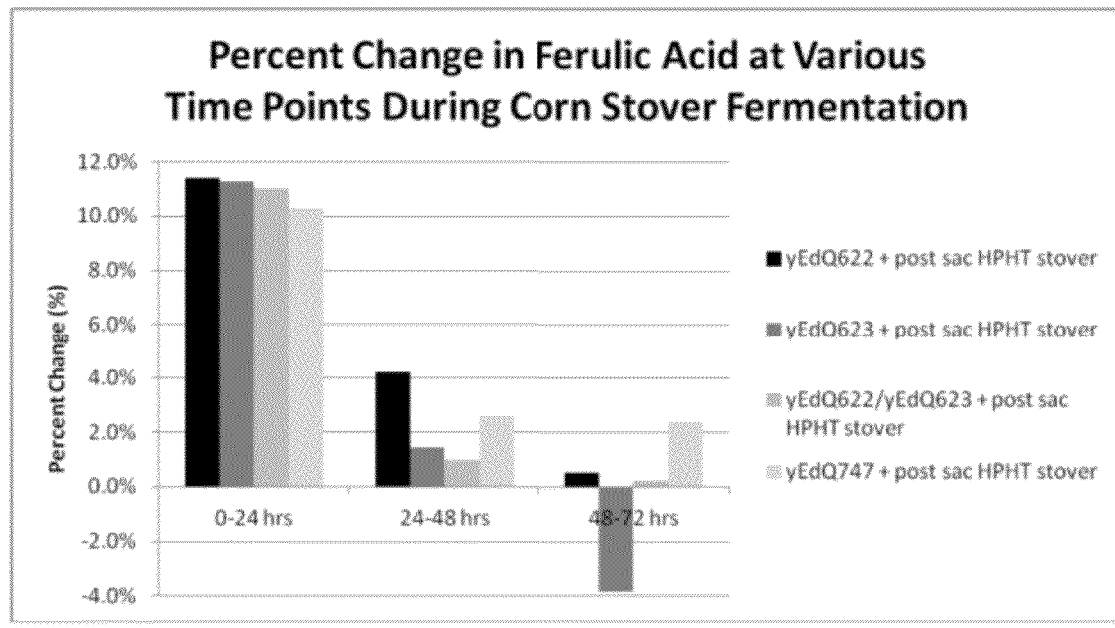
FIG. 21B illustrates ferulic acid levels in ppm.
Figure 21C:
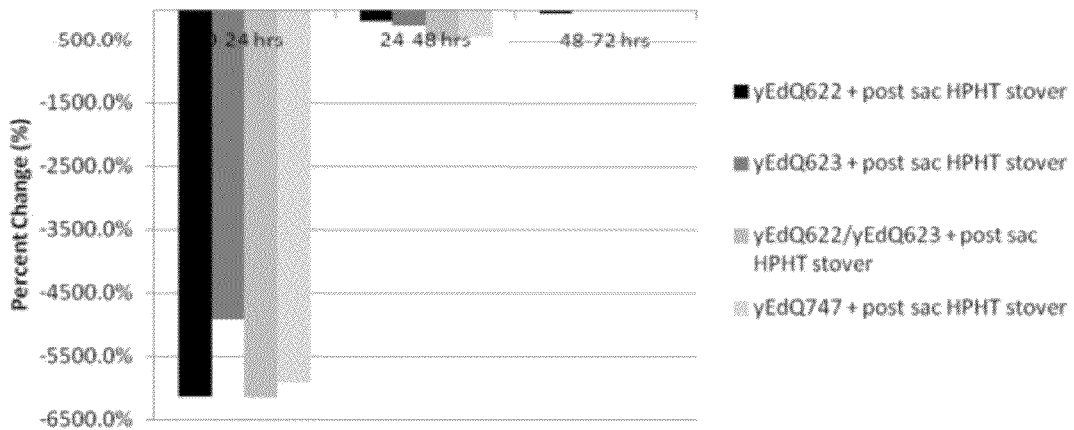
FIG. 21C illustrates furfural levels in ppm.
Figure 21D:
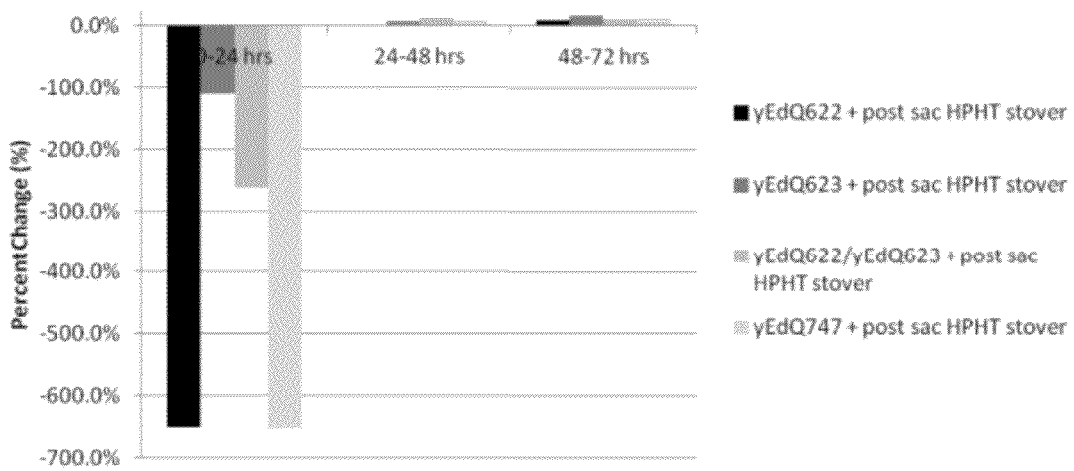
FIG. 21D illustrates 5-HMF levels in ppm. Percent change over time is calculated using the following equation: $[(T2-T1)/T2]*100$, where T represents product amount at set time point.

Ethanol production, glucose consumption, and inhibitor/phenolic compounds level were quantified as a function of time, as seen in FIGS. 19, 20, and 21. Remaining carbohydrate and lignin after 72 hours of fermentation were determined by compositional analysis shown in FIGS. 22 and 23. The compositional analysis protocol used is developed by the National Renewable Energy Laboratory (NREL) entitled, "Determination of Structural Carbohydrates and Lignin in Biomass." Compositional analysis is important because previous experiments showed an increase in ethanol amount using Mnp expressing yeast strains, in comparison to a non-Mnp expressing yeast strain. The additional ethanol obtained could be the result of efficient glucose to ethanol conversion due to strain genetics or due to the effect of Mnp. Based on Mnp activity results using the MBTH/DMAB assay, the mutant Mnp expressed in yEdQ407 has higher activity, suggesting that yEdQ623 has a more active Mnp while yEdQ622 may have additional strain dependent characteristics for increase ethanol production along with Mnp activity.

In-house HPHT milled corn stover material was used for fermentation. After HPHT, the material was saccharified by adding Ctec2 and Htec2 and incubated for ~40 hours to provide nominal sugars for the yeast. Ctec2 was added at a loading of 10% based on cellulose content. Htec2 was added at a loading of 0.5% based on total solids.

Yeast strains described herein are yEdQ622, yEdQ623, and yEdQ747. Propagation was done at 37° C. using yeast peptone dextrose chloramphenicol (ypdc) media with 8% glucose for the first seven hours, and then a 50/50 mixture of stover material and ypdc media was used for overnight adaptation. The next morning, the temperature was increased to 39° C. Due to differences in inoculum material, solids between parameters vary slightly. The parameters tested are as follows, along with subsequent solid %:

1. yEdQ622+post saccharified HPHT stover; ~17% solids
2. yEdQ623+post saccharified HPHT stover; 12.8% solids
3. yEdQ622/yEdQ623+post saccharified stover; 14.7% solids
4. yEdQ747+post saccharified HPHT stover; ~17% solids
5. post saccharified HPHT stover+NO YEAST; 18.9% solids
6. pre saccharified HPHT stover+NO YEAST; 18.6% solids Fermentations were performed at a scale of 200 grams of corn stover material in a 500 ml flask, in triplicate. A nitrogen source of urea was added at 500 parts per million (ppm) in addition to antibiotics. Cyclohexamide was added to flasks containing no yeast. Cellulosic material was inoculated at 40 million cells per gram cellulosic material. For inoculation, cells were first counted and the appropriate amount of liquid dispensed into the flasks. A spin down and removal of supernatant was not done to enable Mnp contained in the supernatant to work immediately on the biomass. The temperature profile of this fermentation was 40° C. for 72 hours. Samples were taken for HPLC at 0, 24, 48, and 72 hours. However, fermentation was finished at 24 hours. After 72 hours, triplicate flasks were pooled and dried for carbohydrate/lignin compositional analysis.

Results: Average ethanol amounts at 24, 48, and 72 hours are shown in FIG. 19. Residual ethanol from propagation was corrected for by deducting amounts at time 0 with those at 24, 48, and 72 hours. Average glucose amounts are comparable among strains as shown in FIG. 20.

24 Hour Analysis: Highest average ethanol amount was observed with yEdQ623+post saccharified HPHT stover material at 1.751 w/v %. Lowest average ethanol amount was observed with control strain yEdQ747+post saccharified HPHT stover material at 1.694 w/v %.

48 Hours Analysis: Highest average ethanol amount was observed with yEdQ622+post saccharified HPHT stover material at 1.845 w/v %. Lowest average ethanol amount was observed with yEdQ747+post saccharified HPHT stover material and yEdQ622/yEdQ623+post saccharified stover material at 1.756 w/v %.

72 Hours Analysis: Highest average ethanol amount was observed with yEdQ622+post saccharified HPHT stover material at 1.880 w/v %. Lowest average ethanol amount was observed with yEdQ747+post saccharified HPHT stover material at 1.763 w/v %.

Inhibitor/phenolic compound levels are presented in FIG. 21A-D. Of the panel of inhibitor compounds screened during fermentation, syringaldehyde, ferulic acid, 5-HMF, and furfural are presented here as illustrative examples Inhibitors/phenolic compounds levels were graphed based on percent change between different time points. Since inoculum amounts varied among strains, initial inhibitor/phenolic amounts likewise varied, thus were normalized and graphed by percent change. A positive percent change indicates an increase in a compound between one time point versus another, whereas a negative percent change indicates a decrease in the compound. Differences in phenolic compound levels are evident in fermentations containing yEdQ623. yEdQ623 selectively decreased syringaldehyde at 24-72 hours. yEdQ623 selective decreased ferulic acid at 48-72 hours. In contrast, all strains decreased furfural predominantly at early times within 24 hours of fermentation. yEdQ622 and control strain yEdQ747 decreased 5-HMF also within 24 hours of fermentation. The inhibitor profiles for 5-HMF and furfural were as expected, since detoxification of these products is likely a property of yeast metabolics, rather than an Mnp-mediated property.

Figure 22:
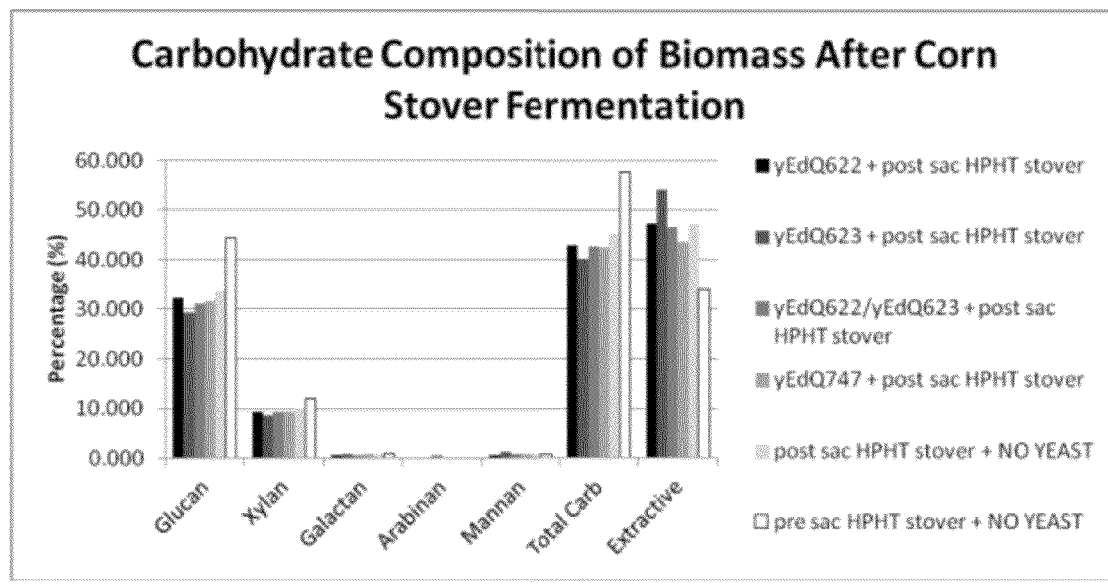
FIG. 22 depicts carbohydrate compositional analysis after 72 hours fermentation at 40° C.; experiment shown in FIG. 19. and measured by HPLC. Samples were analyzed in triplicate for changes in % carbohydrate. Quantification and protocol is outlined in NREL's document titled "Determination of Structural Carbohydrates and Lignin in Biomass." Carbohydrate levels are shown for control yeast strain yEdQ747, yEdQ MnP-expressing strains 622 and 623, and additional control conditions of HPHT material containing no yeast before (pre-sacc) and after (post-sacc) saccharification. Compositional levels are measured as a relative percentage. "Extractives" refers to the soluble fraction removed from the material prior to the carbohydrate determination, in accordance with the referenced protocol.
Figure 23:
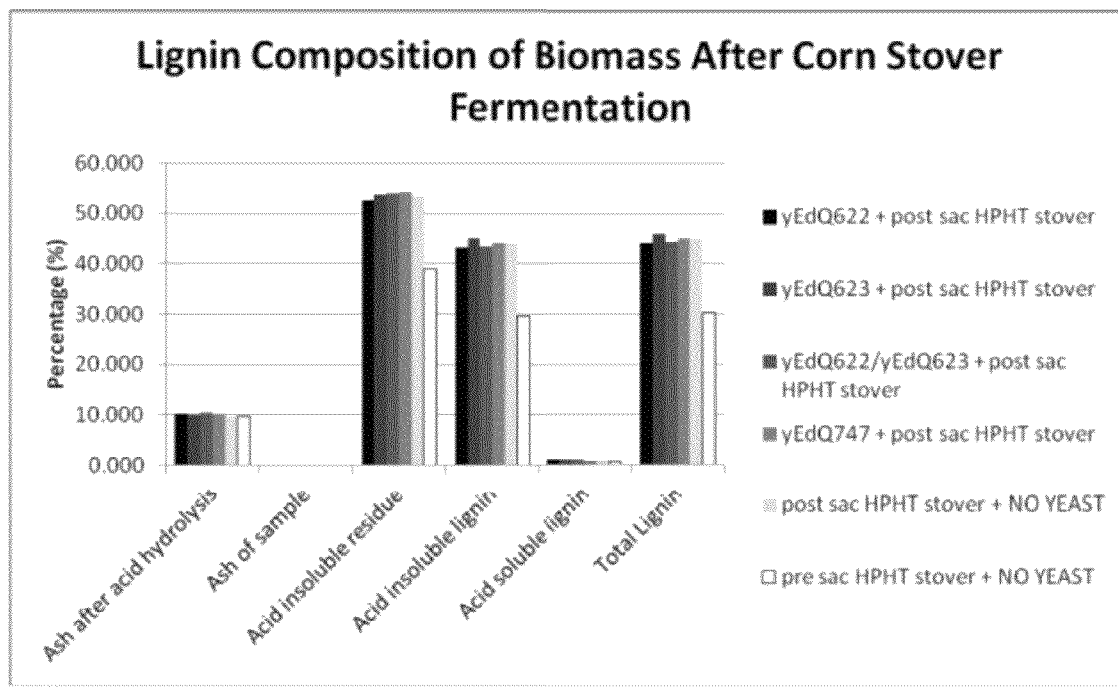
FIG. 23 depicts lignin compositional analysis after 72 hours fermentation at 40° C.; experiment shown in FIG. 19 and measured by HPLC. Samples were analyzed in triplicate for changes in % lignin. Quantification and protocol is outlined in NREL's document titled "Determination of Structural Carbohydrates and Lignin in Biomass." Lignin levels are shown for control yeast strain yEdQ747, yEdQ MnP-expressing strains 622 and 623, and additional control conditions of HPHT material containing no yeast before (pre-sacc) and after (post-sacc) saccharification. Compositional levels are measured as a relative percentage.

Carbohydrate/lignin composition analysis after 72 hours of fermentation was performed and is presented in FIG. 22 and FIG. 23. After fermentation, triplicate flasks were pooled and processed in triplicates, according to procedures outlined in NREL's protocol. Carbohydrate compositional analysis shows a decrease in glucan and xylan from biomass containing yEdQ623, whereas all other parameters were comparable to one another, excluding pre-saccharified HPHT corn stover material. Lastly, lignin compositional analysis shows comparable lignin amounts amongst all parameters, excluding pre-saccharified HPHT corn stover material.

Conclusion: The data presented here illustrates that Mnp produced by the yeast described herein has an effect on lignocellulosic biomass, as demonstrated by a) the selective decrease in syringaldehyde and ferulic acid by yEdQ623 and b) the decrease in glucan and xylan levels on post fermentation sample.

Regarding the first case, syringaldehyde is a byproduct of lignin disruption, which can be further broken down by Mnp due to its ubiquitous attack on phenolic compounds. It is apparent that syringaldehyde decreased at a greater rate by yEdQ623 versus other strains, suggesting a more active Mnp. Additionally, ferulic acid levels observed show substantial decrease by strain yEdQ623, another indication that is it is a more active Mnp. Ferulic acid is an organic acid that has the property of chelating Mn(III), which is generated by Mnp. Mn(III) acts as a diffusible redox-mediator of phenolic substrates, thus its decrease is potentially a result of uptake by Mn(III). All other parameters showed comparable syringaldehyde and ferulic acid levels.

Regarding the second case, there is a substantial decrease in glucan and xylan from biomass fermented with yEdQ623. This data supports the model that Mnp will disrupt lignin to provide additional access to cellulose and hemicellulose for Ctec2 and Htec2. Glucan is broken down into glucose by Ctec2; therefore a decrease in glucan is a result of Ctec2 activity. Biomass treated with yEdQ623 yielded less glucan. A decrease in glucan can be associated to additional cellulose access for Ctec2 due to lignin disruption by Mnp. Additionally, xylan is broken down into xylose by Htec2; therefore a decrease in xylan is a result of Htec2 activity. Biomass treated with yEdQ623 yielded less xylan. A decrease in xylan can be associated to additional hemicellulose access for Htec2. Thus, the carbohydrate compositional analysis supports the hypothesis that the mutant Mnp has higher activity. However, Mnp's lignin degradation function did not cause a detectable decrease in lignin composition of the biomass after fermentation. Mnp promotes lignin degradation via oxidation of phenolic compounds found in lignin. The oxidized phenolic compound may repolymerize to lignin creating an altered lignin state due to a lack of additional ligninolytic enzymes that can further degrade and expel the oxidized product. This altered state appears to be compatible with cellulase activity. Such observations have been seen in published literature. Though degradation of lignin was not directly observed, an indirect measurement of lignin disruption can be seen in the carbohydrate analysis via reduced glucan and xylan levels in biomass fermented with yEdQ623.

In conclusion, these examples together indicate that the mutant Mnp of yEdQ623 is more active than the wild type Mnp of yEdQ622. However, yEdQ622 may have additional strain dependent characteristics promoting efficient glucose to ethanol conversion, along with Mnp activity. Additionally, the carbohydrate analysis provides insight into the potential mechanism of Mnp and suggests beneficial uses for the improved Mnp yeast strains described herein to enable a more efficient process for ethanol production from lignocellulosic biomass.

It is understood that the examples and embodiments described herein are for illustrative purposes only and that various modifications or changes in light thereof will be suggested to persons skilled in the art and are to be included within the spirit and purview of this application and scope of the appended claims. All publications, sequence accession numbers, patents, and patent applications cited herein are hereby incorporated by reference in their entirety for all purposes.

What is claimed is:

1. An isolated polynucleotide comprising a modified nucleic acid encoding an improved manganese peroxidase, the improved manganese peroxidase comprising a polypeptide having at least 90% sequence identity to the amino acid sequence of SEQ ID NO:1, and having improved manganese peroxidase activity compared to a control manganese peroxidase comprising the amino acid sequence of SEQ ID NO:1.

2. The polynucleotide of claim 1, wherein the improved manganese peroxidase comprises an amino acid at one or more positions corresponding to a position selected from the group consisting of:
   (a) position 17 of SEQ ID NO:1, when the amino acid corresponding to position 17 is an amino acid other than Q;
   (b) position 57 of SEQ ID NO:1, when the amino acid corresponding to position 57 is an amino acid other than D;
   (c) position 80 of SEQ ID NO:1, when the amino acid corresponding to position 80 is an amino acid other than S;
   (d) position 107 of SEQ ID NO:1, when the amino acid corresponding to position 107 is an amino acid other than N;
   (e) position 109 of SEQ ID NO:1, when the amino acid corresponding to position 109 is an amino acid other than H;
   (f) position 111 of SEQ ID NO:1, when the amino acid corresponding to position 111 is an amino acid other than N;
   (g) position 152 of SEQ ID NO:1, when the amino acid corresponding to position 152 is an amino acid other than Q;
   (h) position 278 of SEQ ID NO:1, when the amino acid corresponding to position 278 is an amino acid other than W; and/or
   (i) position 204 of SEQ ID NO:1, when the amino acid corresponding to position 204 is an amino acid other than T.

3. The polynucleotide of claim 1, wherein the improved manganese peroxidase comprises an amino acid at one or more positions corresponding to a position selected from the group consisting of:
   (a) position 17 of SEQ ID NO:1, when the amino acid corresponding to position 17 is S;
   (b) position 57 of SEQ ID NO:1, when the amino acid corresponding to position 57 is K;
   (c) position 80 of SEQ ID NO:1, when the amino acid corresponding to position 80 is N;
   (d) position 107 of SEQ ID NO:1, when the amino acid corresponding to position 107 is S;
   (e) position 109 of SEQ ID NO:1, when the amino acid corresponding to position 109 is L;
   (f) position 111 of SEQ ID NO:1, when the amino acid corresponding to position 111 is L;
   (g) position 152 of SEQ ID NO:1, when the amino acid corresponding to position 152 is A;
   (h) position 278 of SEQ ID NO:1, when the amino acid corresponding to position 278 is A; and/or
   (i) position 204 of SEQ ID NO:1, when the amino acid corresponding to position 204 is S.

4. The polynucleotide of claim 1, wherein the polynucleotide comprises an expression cassette, the expression cassette comprising a heterologous promoter operably linked to the modified nucleic acid.

5. A vector comprising the polynucleotide of claim 1.

6. An isolated cell or culture of cells, wherein the cell(s) comprise the polynucleotide of claim 1, wherein the polynucleotide is heterologous to the cell.

7. The cell of claim 6, wherein the cell is a yeast cell.

8. The cell of claim 7, wherein the cell is a *Saccharomyces cerevisiae*.

9. The cell of claim 6, wherein the improved manganese peroxidase is secreted from the cell.

10. The polynucleotide of claim 1, wherein the improved manganese peroxidase comprises a polypeptide having at least 90% sequence identity to SEQ ID NO:1, wherein the amino acid corresponding to position 17 of SEQ ID NO:1 is S, the amino acid corresponding to position 57 of SEQ ID NO:1 is K, the amino acid corresponding to position 80 of SEQ ID NO:1 is N, the amino acid corresponding to position 107 of SEQ ID NO:1 is S, the amino acid corresponding to position 109 of SEQ ID NO:1 is L, the amino acid corresponding to position 111 of SEQ ID NO:1 is L, the amino acid corresponding to position 152 of SEQ ID NO:1 is A, the amino acid corresponding to position 278 of SEQ ID NO:1 is A, and/or the amino acid corresponding to position 204 of SEQ ID NO:1 is S.

11. A method for converting a cellulose-containing biomass feedstock to a sugar or a non-sugar biomass-derived intermediate, the method comprising treating the biomass with an improved manganese peroxidase encoded by the modified polynucleotide of claim 1, or contacting the biomass with a cell that expresses the improved manganese peroxidase encoded by the modified polynucleotide of claim 1.

12. The method of claim 11, wherein the cellulose-containing biomass feedstock is converted into sugar.

13. The method of claim 12, further comprising fermenting the sugar to ethanol.

14. The method of claim 11, wherein the cellulose-containing biomass feedstock is converted into a non-sugar biomass-derived intermediate.

15. The method of claim 11, wherein the cell is a *Saccharomyces Cerevisiae*.

16. The method of claim 11, wherein the cellulose-containing biomass feedstock is a woody material.

17. The method of claim 16, wherein the woody material is cellulosic or lignocellulosic plant material selected from the group consisting of orchard prunings, chaparral, mill waste, urban wood waste, municipal waste, logging waste, forest thinnings, short-rotation woody crops, and industrial waste.

18. The method of claim 11, wherein the cellulose-containing biomass feedstock is a non-woody material.

19. The method of claim 18, wherein the non-woody material is selected from the group consisting of gramineous agricultural residue, wheat straw, oat straw, rice straw, barley straw, rye straw, flax straw, sugar cane, corn stover, corn stalks, corn cobs, corn husks, prairie grass, switchgrass, gamagrass, foxtail, sugar beet pulp, citrus fruit pulp, seed hulls, cellulosic animal wastes, lawn clippings, seaweed, bagasse, energy cane, and giant reed.

20. The method of claim 11, wherein the cellulose-containing biomass feedstock is corn grain, barley grain, milo grain, wheat grain or rice grain.

\* \* \* \* \*

SEQUENCE LISTING

<160> NUMBER OF SEQ ID NOS: 37

<210> SEQ ID NO 1
<211> LENGTH: 365
<212> TYPE: PRT
<213> ORGANISM: Trametes versicolor
<220> FEATURE:
<223> OTHER INFORMATION: Trametes versicolor wild-type fungus manganese peroxidase

<400> SEQUENCE: 1

Met Ala Phe Lys Thr Leu Ala Ser Leu Leu Ser Val Leu Val Thr Ile
1               5                   10                  15

Gln Val Ala Ser Gly Ala Leu Thr Arg Arg Val Ala Cys Pro Asp Gly
            20                  25                  30

Val Asn Thr Ala Thr Asn Ala Ala Cys Cys Gln Leu Phe Ala Val Arg
        35                  40                  45

Asp Asp Ile Gln Gln Asn Leu Phe Asp Gly Gly Glu Cys Gly Glu Glu
    50                  55                  60

Val His Glu Ser Leu Arg Leu Thr Phe His Asp Ala Ile Gly Ile Ser
65                  70                  75                  80

Pro Ser Ile Ala Ser Arg Gly Gln Phe Gly Gly Gly Ala Asp Gly
                85                  90                  95

Ser Ile Ala Leu Phe Glu Asp Ile Glu Thr Asn Phe His Ala Asn Leu
            100                 105                 110

Gly Val Asp Glu Ile Ile Asp Glu Gln Arg Pro Phe Ile Ala Arg His
        115                 120                 125

Asn Leu Thr Thr Ala Asp Phe Ile Gln Phe Ala Gly Ala Ile Gly Val
130                 135                 140

Ser Asn Cys Pro Gly Ala Pro Gln Leu Asp Val Phe Ile Gly Arg Pro
145                 150                 155                 160

Asp Ala Thr Gln Pro Ala Pro Asp Leu Thr Val Pro Glu Pro Phe Asp
                165                 170                 175

Thr Val Asp Ser Ile Ile Glu Arg Phe Ser Asp Ala Gly Gly Phe Thr
            180                 185                 190

Pro Ala Glu Ile Val Ala Leu Leu Val Ser His Thr Ile Ala Ala Ala
        195                 200                 205

Asp His Val Asp Pro Ser Ile Pro Gly Thr Pro Phe Asp Ser Thr Pro
    210                 215                 220

Glu Glu Phe Asp Thr Gln Phe Phe Ile Glu Thr Gln Leu Arg Gly Thr
225                 230                 235                 240

Leu Phe Pro Gly Thr Gly Gly Asn Gln Gly Glu Val Glu Ser Pro Leu
                245                 250                 255

Arg Gly Glu Leu Arg Leu Gln Ser Asp Ser Glu Leu Ala Arg Asp Ser
            260                 265                 270

Arg Thr Ala Cys Glu Trp Gln Ser Phe Val Asn Asn Gln Ala Lys Leu
        275                 280                 285

Gln Ser Ala Phe Lys Ala Ala Phe Arg Lys Met Thr Val Leu Gly His
    290                 295                 300

Asp Glu Ser Leu Leu Ile Glu Cys Ser Glu Leu Val Pro Thr Pro Pro
305                 310                 315                 320

Pro Ala Thr Ser Val Ala His Phe Pro Ala Gly Leu Ser Asn Ala Asp
                325                 330                 335

Val Glu Gln Ala Cys Ala Asp Thr Pro Phe Pro Thr Leu Pro Thr Asp
            340                 345                 350

```
Pro Gly Pro Val Thr Thr Val Ala Pro Val Pro Pro Ser
        355                 360                 365

<210> SEQ ID NO 2
<211> LENGTH: 345
<212> TYPE: PRT
<213> ORGANISM: Laccaria bicolor
<220> FEATURE:
<223> OTHER INFORMATION: Laccaria bicolor S238N-H82 wild-type fungus
      manganese peroxidase

<400> SEQUENCE: 2

Met Ala Val Ala Leu Phe Ser Thr Leu Ile Thr Leu Leu Phe Gly Ala
1               5                   10                  15

Gln Ile Ala Asn Ala Ala Gly Leu Ser Asn Gln Val Thr Cys Ser Thr
            20                  25                  30

Gly His Val Thr Ser Asn Lys Ala Cys Cys Pro Leu Phe Pro Ile Val
        35                  40                  45

Asp Asn Ile Gln Gln Asn Leu His Gly Gly Ala Cys Gly Phe Gly
    50                  55                  60

Ala His Thr Ala Leu Arg Leu Ser Phe His Asp Ala Ile Gly Phe Ser
65                  70                  75                  80

Ile His Gly Gly Lys Gly Gly Ala Asp Gly Ser Ile Leu Ile Phe
                85                  90                  95

Asn Thr Thr Glu Leu Ala Tyr Asp Ala Asn Val Gly Ile Asp Asp Ile
            100                 105                 110

Thr Ala Asp Gln Trp Pro Val Phe Gln Thr Thr Gly Leu Ser Ala Gly
        115                 120                 125

Asp Phe Leu His Leu Ala Ala Ala Val Gly Thr Ala Asn Cys Pro Gly
130                 135                 140

Ala Pro Arg Leu Gln Tyr Met Phe Gly Arg Pro Pro Val Ala Pro
145                 150                 155                 160

Ala Pro Asp Asn Thr Val Pro Lys Pro Thr Asp Ser Val Asp Ser Met
                165                 170                 175

Leu Ala Arg Met Ala Asp Ala Gly Phe Ser Pro Ala Glu Leu Val Ala
            180                 185                 190

Leu Leu Ala Ser His Ser Ile Ala Asn Val Val Asp Ile Asp Pro Thr
        195                 200                 205

Val Ala Gly Ile Pro Leu Asp Ser Thr Ser Thr Phe Asp Ser Gln
    210                 215                 220

Leu Phe Leu Glu Val Leu Leu Lys Gly Thr Val Phe Pro Gly Ser Gly
225                 230                 235                 240

Ala Asn Ser Gly Glu Val Gln Ser Phe Thr Thr Ala Glu Met Arg Leu
                245                 250                 255

Gln Ser Asp Ser Ala Ile Ala Arg Asp His Arg Thr Ala Cys Ser Trp
            260                 265                 270

Gln Ser Met Ile Asn Asn Gln Ala Arg Met Met Thr Gln Phe Lys Ala
        275                 280                 285

Ala Met Ala Lys Leu Gln Val Leu Gly Gln Asp Thr Ser Lys Leu Ile
290                 295                 300

Asp Cys Ser Asp Val Ile Pro Val Pro Lys Pro Phe Ala Gly Pro Ile
305                 310                 315                 320

Lys Tyr Pro Ser Ser Phe Ser Gln Ala Asn Ile Glu Gln Lys Cys Thr
                325                 330                 335

Glu Phe Lys Phe Pro Ser Val Gly Arg
            340                 345
```

```
<210> SEQ ID NO 3
<211> LENGTH: 361
<212> TYPE: PRT
<213> ORGANISM: Pleurotus ostreatus
<220> FEATURE:
<223> OTHER INFORMATION: Pleurotus ostreatus wild-type fungus manganese
      peroxidase

<400> SEQUENCE: 3

Met Thr Phe Ala Ser Leu Ser Ala Leu Val Leu Val Phe Ala Val Thr
1               5                   10                  15

Val Gln Val Ala Gln Ala Val Ser Leu Pro Gln Lys Arg Ala Thr Cys
            20                  25                  30

Ala Gly Gly Gln Val Thr Ala Asn Ala Ala Cys Cys Val Leu Phe Pro
        35                  40                  45

Leu Met Glu Asp Leu Gln Lys Asn Leu Phe Asp Asp Gly Ala Cys Gly
    50                  55                  60

Glu Asp Ala His Glu Ala Leu Arg Leu Thr Phe His Asp Ala Ile Gly
65                  70                  75                  80

Phe Ser Pro Ser Arg Gly Val Met Gly Gly Ala Asp Gly Ser Val Ile
                85                  90                  95

Thr Phe Ser Asp Thr Glu Val Asn Phe Pro Ala Asn Leu Gly Ile Asp
            100                 105                 110

Glu Ile Val Glu Ala Glu Lys Pro Phe Leu Ala Arg His Asn Ile Ser
        115                 120                 125

Ala Gly Asp Leu Val His Phe Ala Gly Thr Leu Ala Val Thr Asn Cys
    130                 135                 140

Pro Gly Ala Pro Arg Ile Pro Phe Phe Leu Gly Arg Pro Pro Ala Lys
145                 150                 155                 160

Ala Ala Ser Pro Ile Gly Leu Val Pro Glu Pro Phe Asp Thr Ile Thr
                165                 170                 175

Asp Ile Leu Ala Arg Met Asp Asp Ala Gly Phe Val Ser Val Glu Val
            180                 185                 190

Val Trp Leu Leu Ser Ala His Ser Val Ala Ala Ala Asp His Val Asp
        195                 200                 205

Glu Thr Ile Pro Gly Thr Pro Phe Asp Ser Thr Pro Asn Leu Phe Asp
    210                 215                 220

Ser Gln Ile Phe Ile Glu Thr Gln Leu Arg Gly Ile Ser Phe Pro Gly
225                 230                 235                 240

Thr Gly Gly Asn His Gly Glu Val Gln Ser Pro Leu Lys Gly Glu Met
                245                 250                 255

Arg Leu Gln Ser Asp His Leu Phe Ala Arg Asp Asp Arg Thr Ser Cys
            260                 265                 270

Glu Trp Gln Ser Met Thr Asn Asp Gln Gln Lys Ile Gln Asp Arg Phe
        275                 280                 285

Ser Asp Thr Leu Phe Lys Met Ser Met Leu Gly Gln Asn Gln Asp Ala
    290                 295                 300

Met Ile Asp Cys Ser Asp Val Ile Pro Val Pro Ala Ala Leu Val Thr
305                 310                 315                 320

Lys Pro His Leu Pro Ala Gly Lys Ser Lys Thr Asp Val Glu Gln Ala
                325                 330                 335

Cys Ala Thr Gly Ala Phe Pro Ala Leu Gly Ala Asp Pro Gly Pro Val
            340                 345                 350

Thr Ser Val Pro Arg Val Pro Pro Ala
        355                 360
```

<210> SEQ ID NO 4
<211> LENGTH: 377
<212> TYPE: PRT
<213> ORGANISM: Lentinula edodes
<220> FEATURE:
<223> OTHER INFORMATION: Lentinula edodes wild-type fungus manganese peroxidase

<400> SEQUENCE: 4

```
Met Ala Phe Ser Thr Met Ile Leu Pro Phe Val Ala Leu Ala Leu Ser
1               5                   10                  15

Thr Val Asn Ala Ala Pro Ala Ala Gln Asn Ala Arg Cys Ser Asp Gly
            20                  25                  30

Thr Val Val Pro Asn Ser Ile Cys Cys Asp Phe Ile Pro Leu Ala Gln
        35                  40                  45

Asp Leu Thr Glu Thr Leu Phe Glu Asn Gln Cys Gly Glu Thr Ala His
    50                  55                  60

Glu Val Leu Arg Leu Ser Phe His Asp Ala Ile Ala Ile Ser Gln Ser
65                  70                  75                  80

Leu Gly Pro Ser Ala Gly Gly Ala Asp Gly Ser Met Leu Ile Phe
                85                  90                  95

Pro Asp Val Glu Pro Asn Phe Ala Ala Asn Leu Gly Ile Ser Asp Ser
            100                 105                 110

Val Asn Asp Leu Ala Pro Phe Leu Ala Ser Gly Lys Phe Pro Thr Ile
        115                 120                 125

Thr Ala Gly Asp Met Ile Gln Phe Gly Ala Ala Val Ala Val Gly Leu
    130                 135                 140

Cys Pro Gly Ala Pro Gln Leu Glu Phe Arg Ala Gly Arg Pro Asn Ala
145                 150                 155                 160

Thr Ala Pro Ala Val Asp Gly Leu Ile Pro Glu Pro Gln Asn Thr Val
                165                 170                 175

Asp Glu Ile Leu Ala Arg Phe Gln Asp Ala Ala Asn Met Asn Ala Glu
            180                 185                 190

Asp Ile Val Ser Leu Leu Val Ser His Thr Val Ala Arg Ala Asp His
        195                 200                 205

Val Asp Pro Thr Leu Asp Ala Ala Pro Phe Asp Ser Thr Pro Phe Thr
    210                 215                 220

Phe Asp Ser Gln Phe Phe Leu Glu Thr Leu Leu Thr Gly Val Gly Phe
225                 230                 235                 240

Pro Gly Thr Thr Asn Asn Thr Gly Glu Val Ser Ser Pro Leu Pro Leu
                245                 250                 255

Thr Val Gly Asp Asn Val Gly Glu Leu Arg Leu Gln Ser Asp Phe Glu
            260                 265                 270

Leu Ala Arg Asp Ser Arg Thr Ala Cys Phe Trp Gln Ser Met Ile Asn
        275                 280                 285

Gln Glu Ala Leu Met Ala Ser Arg Phe Lys Ala Ala Met Ala Lys Met
    290                 295                 300

Ala Val Ile Gly His Asn Ala Asn Asp Leu Ile Asp Cys Ser Ala Val
305                 310                 315                 320

Val Pro Lys Pro Val Pro Ala Leu Asn Lys Pro Ala Thr Phe Pro Ala
                325                 330                 335

Thr Lys Thr Lys Ala Asp Val Gln Gln Ala Cys Pro Glu Pro Phe Pro
            340                 345                 350

Asn Leu Thr Thr Asp Arg Ala Pro Arg Glu Thr Glu Ile Pro His Cys
        355                 360                 365
```

```
Pro Asp Asn Glu Ala Thr Cys Thr Ser
    370                 375

<210> SEQ ID NO 5
<211> LENGTH: 364
<212> TYPE: PRT
<213> ORGANISM: Ganoderma applanatum
<220> FEATURE:
<223> OTHER INFORMATION: Ganoderma applanatum wild-type fungus manganese
      peroxidase

<400> SEQUENCE: 5

Met Phe Ser Lys Val Phe Leu Ser Leu Val Val Leu Ala Ser Ser Val
1               5                   10                  15

Ala Ala Ala Val Pro Thr Val Gly Arg Arg Ala Thr Cys Ala Asn Gly
            20                  25                  30

Lys Thr Thr Ala Asn Asp Ala Cys Cys Val Trp Phe Asp Val Leu Asp
        35                  40                  45

Asp Ile Gln Glu Asn Leu Phe His Gly Gly Gln Cys Gly Glu Asp Ala
    50                  55                  60

His Glu Ser Leu Arg Leu Thr Phe His Asp Ala Ile Ala Phe Ser Pro
65                  70                  75                  80

Ala Leu Thr Ala Ala Gly Gln Phe Gly Gly Gly Ala Asp Gly Ser
                85                  90                  95

Ile Ile Ala His Ser Asp Val Glu Leu Thr Tyr Pro Val Asn Asp Gly
                100                 105                 110

Leu Asp Glu Ile Val Glu Ala Ser Arg Pro Phe Ala Ile Lys His Asn
            115                 120                 125

Val Ser Phe Gly Asp Phe Ile Gln Phe Ala Gly Ala Val Gly Val Ala
        130                 135                 140

Asn Cys Asn Gly Gly Pro Gln Leu Ser Phe Phe Ala Gly Arg Ser Asn
145                 150                 155                 160

Asp Ser Gln Pro Ser Pro Pro Asn Leu Val Pro Leu Pro Ser Asp Thr
                165                 170                 175

Ala Asp Thr Ile Leu Ser Arg Phe Ser Asp Ala Gly Phe Asp Ala Val
            180                 185                 190

Glu Val Val Trp Leu Leu Val Ser His Thr Val Gly Ser Gln Asn Thr
        195                 200                 205

Val Asp Ser Ser Ile Pro Gly Ala Pro Phe Asp Ser Thr Pro Ser Asp
    210                 215                 220

Phe Asp Ala Gln Phe Phe Val Glu Thr Met Leu Asn Gly Thr Leu Val
225                 230                 235                 240

Pro Gly Asn Gly Leu Gln Asp Gly Glu Val Leu Ser Pro Tyr Pro Gly
                245                 250                 255

Glu Phe Arg Leu Gln Ser Asp Phe Ala Leu Ser Arg Asp Ser Arg Thr
            260                 265                 270

Thr Cys Glu Trp Gln Lys Met Ile Ala Asp Arg Ala Asn Met Leu Glu
        275                 280                 285

Lys Phe Glu Ile Thr Met Leu Lys Met Ser Leu Leu Gly Phe Asp Gln
    290                 295                 300

Ser Ala Leu Thr Asp Cys Ser Asp Val Ile Pro Thr Ala Thr Gly Thr
305                 310                 315                 320

Val Gln Asp Pro Phe Ile Pro Ala Gly Leu Thr Val Asp Asp Leu Gln
                325                 330                 335

Pro Ala Cys Ser Ser Ser Ala Phe Pro Thr Val Thr Val Ala Gly
            340                 345                 350
```

```
Ala Val Thr Ser Ile Pro Ala Val Pro Leu Asn Ser
        355                 360

<210> SEQ ID NO 6
<211> LENGTH: 362
<212> TYPE: PRT
<213> ORGANISM: Phlebia radiate
<220> FEATURE:
<223> OTHER INFORMATION: Phlebia radiate wild-type fungus manganese
      peroxidase

<400> SEQUENCE: 6

Met Ala Phe Lys Gln Leu Leu Thr Ala Ile Ser Ile Val Ser Val Ala
1               5                   10                  15

Asn Ala Ala Leu Thr Arg Arg Val Ala Cys Pro Asp Gly Val Asn Thr
            20                  25                  30

Ala Thr Asn Ala Val Cys Cys Ser Leu Phe Ala Val Arg Asp Leu Ile
        35                  40                  45

Gln Asp Gln Leu Phe Asp Gly Gly Glu Cys Gly Glu Glu Val His Glu
    50                  55                  60

Ser Leu Arg Leu Thr Phe His Asp Ala Ile Gly Ile Ser Pro Thr Ile
65                  70                  75                  80

Ala Ser Thr Gly Val Phe Gly Gly Gly Ala Asp Gly Ser Ile Ala
                85                  90                  95

Ile Phe Ala Glu Ile Glu Thr Asn Phe His Ala Asn Asn Gly Val Asp
            100                 105                 110

Glu Ile Ile Gly Glu Gln Ala Pro Phe Ile Gln Met Thr Asn Met Thr
        115                 120                 125

Thr Ala Asp Phe Ile Gln Phe Ala Gly Ala Val Gly Val Ser Asn Cys
    130                 135                 140

Pro Gly Ala Pro Ala Leu Pro Val Phe Val Gly Arg Pro Asp Ala Thr
145                 150                 155                 160

Gln Pro Ala Pro Asp Lys Thr Val Pro Glu Pro Phe Asp Thr Val Asp
                165                 170                 175

Ser Ile Leu Ala Arg Phe Ala Asp Ala Gly Gly Phe Ser Ser Ala Glu
            180                 185                 190

Val Val Ala Leu Leu Ala Ser His Thr Ile Ala Ala Ala Asp His Val
        195                 200                 205

Asp Pro Ser Ile Pro Gly Thr Pro Phe Asp Ser Thr Pro Glu Ile Phe
    210                 215                 220

Asp Thr Gln Phe Phe Ile Glu Thr Gln Leu Arg Gly Ile Leu Phe Pro
225                 230                 235                 240

Gly Thr Gly Gly Asn Gln Gly Glu Val Glu Ser Pro Leu His Gly Glu
                245                 250                 255

Ile Arg Leu Gln Ser Asp Ser Glu Leu Ala Arg Asp Ser Arg Thr Ala
            260                 265                 270

Cys Glu Trp Gln Ser Phe Val Asn Asn Gln Ala Lys Ile Gln Ser Ala
        275                 280                 285

Phe Lys Ala Ala Phe Arg Lys Met Thr Ile Leu Gly His Ser Glu Ser
    290                 295                 300

Ser Leu Ile Glu Cys Ser Glu Val Ile Gln Thr Pro Pro Ala Leu Glu
305                 310                 315                 320

Gly Asn Ala His Leu Pro Ala Gly Gln Thr Met Asn Asp Ile Glu Gln
                325                 330                 335

Ala Cys Ala Thr Thr Pro Phe Pro Ser Leu Ser Ala Asp Pro Gly Pro
            340                 345                 350
```

```
Ala Thr Ser Val Ala Pro Val Pro Pro Ser
        355                 360

<210> SEQ ID NO 7
<211> LENGTH: 378
<212> TYPE: PRT
<213> ORGANISM: Phanerochaete chrysosporium
<220> FEATURE:
<223> OTHER INFORMATION: Phanerochaete chrysosporium wild-type fungus
      manganese peroxidase

<400> SEQUENCE: 7

Met Ala Phe Lys Ser Leu Ile Ala Phe Val Ala Leu Ala Ala Ala Val
1               5                   10                  15

Arg Ala Ala Pro Thr Ala Val Cys Pro Asp Gly Thr Arg Val Ser His
            20                  25                  30

Ala Ala Cys Cys Ala Phe Ile Pro Leu Ala Gln Asp Leu Gln Glu Thr
        35                  40                  45

Ile Phe Gln Asn Glu Cys Gly Glu Asp Ala His Glu Val Ile Arg Leu
    50                  55                  60

Thr Phe His Asp Ala Ile Ala Ile Ser Arg Ser Gln Gly Pro Lys Ala
65                  70                  75                  80

Gly Gly Gly Ala Asp Gly Ser Met Leu Leu Phe Pro Thr Val Glu Pro
                85                  90                  95

Asn Phe Ser Ala Asn Asn Gly Ile Asp Asp Ser Val Asn Asn Leu Ile
            100                 105                 110

Pro Phe Met Gln Lys His Asn Thr Ile Ser Ala Ala Asp Leu Val Gln
        115                 120                 125

Phe Ala Gly Ala Val Ala Leu Ser Asn Cys Pro Gly Ala Pro Arg Leu
    130                 135                 140

Glu Phe Leu Ala Gly Arg Pro Asn Lys Thr Ile Ala Ala Val Asp Gly
145                 150                 155                 160

Leu Ile Pro Glu Pro Gln Asp Ser Val Thr Lys Ile Leu Gln Arg Phe
                165                 170                 175

Glu Asp Ala Gly Gly Phe Thr Pro Phe Glu Val Val Ser Leu Leu Ala
            180                 185                 190

Ser His Ser Val Ala Arg Ala Asp Lys Val Asp Gln Thr Ile Asp Ala
        195                 200                 205

Ala Pro Phe Asp Ser Thr Pro Phe Thr Phe Asp Thr Gln Val Phe Leu
    210                 215                 220

Glu Val Leu Leu Lys Gly Val Gly Phe Pro Gly Ser Ala Asn Asn Thr
225                 230                 235                 240

Gly Glu Val Ala Ser Pro Leu Pro Leu Gly Ser Gly Ser Asp Thr Gly
                245                 250                 255

Glu Met Arg Leu Gln Ser Asp Phe Ala Leu Ala His Asp Pro Arg Thr
            260                 265                 270

Ala Cys Ile Trp Gln Gly Phe Val Asn Glu Gln Ala Phe Met Ala Ala
        275                 280                 285

Ser Phe Arg Ala Ala Met Ser Lys Leu Ala Val Leu Gly His Asn Arg
    290                 295                 300

Asn Ser Leu Ile Asp Cys Ser Asp Val Val Pro Val Pro Lys Pro Ala
305                 310                 315                 320

Thr Gly Gln Pro Ala Met Phe Pro Ala Ser Thr Gly Pro Gln Asp Leu
                325                 330                 335

Glu Leu Ser Cys Pro Ser Glu Arg Phe Pro Thr Leu Thr Thr Gln Pro
            340                 345                 350
```

```
Gly Ala Ser Gln Ser Leu Ile Ala His Cys Pro Asp Gly Ser Met Ser
            355                 360                 365

Cys Pro Gly Val Gln Phe Asn Gly Pro Ala
        370                 375

<210> SEQ ID NO 8
<211> LENGTH: 388
<212> TYPE: PRT
<213> ORGANISM: Gelatoporia subvermispora
<220> FEATURE:
<223> OTHER INFORMATION: Gelatoporia subvermispora wild-type fungus
      manganese peroxidase

<400> SEQUENCE: 8

Met Ala Phe Ala Ser Leu Leu Ala Leu Val Ala Leu Ala Ala Thr Val
1               5                   10                  15

Arg Ala Ala Pro Ser Ser Ser Val Thr Cys Ser Asp Gly Thr Val
                20                  25                  30

Val Pro Asp Ser Met Cys Cys Asp Phe Ile Pro Leu Ala Gln Asp Leu
            35                  40                  45

Gln Ser Met Val Leu Gln Asn Glu Cys Gly Glu Asp Ala His Glu Ile
    50                  55                  60

Ile Arg Leu Thr Phe His Asp Ala Ile Ala Ile Ser Gln Ser Leu Pro
65                  70                  75                  80

Pro Ser Ala Gly Thr Gly Ala Asp Gly Ser Met Leu Leu Phe Pro Leu
                85                  90                  95

Val Glu Pro Glu Phe Gln Ala Ser Asn Gly Ile Asp Asp Ser Val Asn
            100                 105                 110

Asn Leu Ile Pro Phe Leu Ser Ser His Pro Asn Ile Thr Ala Gly Asp
        115                 120                 125

Leu Val Gln Phe Ala Gly Ala Val Ala Leu Thr Asn Cys Pro Gly Ala
    130                 135                 140

Pro Arg Glu Leu Leu Ala Gly Arg Lys Asn Ala Val Ala Pro Ala Ile
145                 150                 155                 160

Asp Gly Leu Ile Pro Val Pro Gln Asp Asn Val Ser Thr Ile Leu Ala
                165                 170                 175

Arg Phe Ala Asp Ala Gly Asn Phe Ser Pro Phe Glu Val Val Ser Leu
            180                 185                 190

Leu Ala Ser His Ser Val Ala Arg Ala Asp Lys Val Asp Pro Thr Leu
        195                 200                 205

Asp Ala Ala Pro Phe Asp Thr Thr Pro Phe Thr Phe Asp Thr Gln Ile
    210                 215                 220

Phe Leu Glu Val Leu Leu Lys Gly Val Gly Phe Pro Gly Leu Asp Asn
225                 230                 235                 240

Asn Thr Gly Glu Val Ala Ser Pro Leu Pro Phe Gly Asp Thr Ser Thr
                245                 250                 255

Gly Gly Asn Asp Thr Gly Met Met Arg Leu Gln Ser Asp Phe Ala Leu
            260                 265                 270

Ala Arg Asp Glu Arg Thr Ala Cys Phe Trp Gln Gly Phe Val Asp Gln
        275                 280                 285

Gln Asp Phe Met Ala Gln Ser Phe Gln Ala Ala Phe Glu Lys Met Ala
    290                 295                 300

Ile Leu Gly Ser Asn Ala Ala Asp Leu Ile Asn Cys Ser Ala Val Val
305                 310                 315                 320

Pro Gln Ser Val Gly Pro Val Thr Val Pro Ala Thr Phe Pro Ala Thr
                325                 330                 335
```

```
Thr Gly Pro Gln Asp Leu Gln Leu Asn Cys Thr Ser Glu Thr Phe Pro
            340                 345                 350

Ser Leu Ser Ile Asp Pro Gly Ala Thr Glu Thr Leu Ile Pro His Cys
        355                 360                 365

Pro Asp Gly Thr Glu Asp Cys Pro Ser Leu Gln Phe Ser Gly Pro Ala
    370                 375                 380

Thr Asp Ser Pro
385

<210> SEQ ID NO 9
<211> LENGTH: 21
<212> TYPE: PRT
<213> ORGANISM: Artificial Sequence
<220> FEATURE:
<223> OTHER INFORMATION: synthetic manganese peroxidase unmodified form
      active site domain "Motif A"
<220> FEATURE:
<221> NAME/KEY: VARIANT
<222> LOCATION: (1)...(1)
<223> OTHER INFORMATION: Xaa = Asp, His, Gly, Gln or Glu
<220> FEATURE:
<221> NAME/KEY: VARIANT
<222> LOCATION: (2)...(2)
<223> OTHER INFORMATION: Xaa = Gly, Asp or Asn
<220> FEATURE:
<221> NAME/KEY: VARIANT
<222> LOCATION: (3)...(3)
<223> OTHER INFORMATION: Xaa = Gly or absent
<220> FEATURE:
<221> NAME/KEY: VARIANT
<222> LOCATION: (4)...(4)
<223> OTHER INFORMATION: Xaa = Glu, Ala or Gln
<220> FEATURE:
<221> NAME/KEY: VARIANT
<222> LOCATION: (7)...(7)
<223> OTHER INFORMATION: Xaa = Glu or Phe
<220> FEATURE:
<221> NAME/KEY: VARIANT
<222> LOCATION: (8)...(8)
<223> OTHER INFORMATION: Xaa = Glu, Asp, Gly or Thr
<220> FEATURE:
<221> NAME/KEY: VARIANT
<222> LOCATION: (9)...(9)
<223> OTHER INFORMATION: Xaa = Val or Ala
<220> FEATURE:
<221> NAME/KEY: VARIANT
<222> LOCATION: (11)...(11)
<223> OTHER INFORMATION: Xaa = Glu or Thr
<220> FEATURE:
<221> NAME/KEY: VARIANT
<222> LOCATION: (12)...(12)
<223> OTHER INFORMATION: Xaa = Ser, Ala, Val or Ile
<220> FEATURE:
<221> NAME/KEY: VARIANT
<222> LOCATION: (13)...(13)
<223> OTHER INFORMATION: Xaa = Leu or Ile
<220> FEATURE:
<221> NAME/KEY: VARIANT
<222> LOCATION: (16)...(16)
<223> OTHER INFORMATION: Xaa = Thr or Ser

<400> SEQUENCE: 9

Xaa Xaa Xaa Xaa Cys Gly Xaa Xaa Xaa His Xaa Xaa Xaa Arg Leu Xaa
1               5                   10                  15

Phe His Asp Ala Ile
            20

<210> SEQ ID NO 10
<211> LENGTH: 21
<212> TYPE: PRT
<213> ORGANISM: Artificial Sequence
<220> FEATURE:
```

OTHER INFORMATION: synthetic manganese peroxidase unmodified form
        active site domain "Motif B"
<220> FEATURE:
<221> NAME/KEY: VARIANT
<222> LOCATION: (6)...(6)
<223> OTHER INFORMATION: Xaa = Ile, Val or Met
<220> FEATURE:
<221> NAME/KEY: VARIANT
<222> LOCATION: (7)...(7)
<223> OTHER INFORMATION: Xaa = Ala, Ile or Leu
<220> FEATURE:
<221> NAME/KEY: VARIANT
<222> LOCATION: (8)...(8)
<223> OTHER INFORMATION: Xaa = Ile, Leu, Thr or Ala
<220> FEATURE:
<221> NAME/KEY: VARIANT
<222> LOCATION: (9)...(9)
<223> OTHER INFORMATION: Xaa = Phe or His
<220> FEATURE:
<221> NAME/KEY: VARIANT
<222> LOCATION: (10)...(10)
<223> OTHER INFORMATION: Xaa = Ala, Glu, Ser, Asn or Pro
<220> FEATURE:
<221> NAME/KEY: VARIANT
<222> LOCATION: (11)...(11)
<223> OTHER INFORMATION: Xaa = Glu, Asp, Thr or Leu
<220> FEATURE:
<221> NAME/KEY: VARIANT
<222> LOCATION: (12)...(12)
<223> OTHER INFORMATION: Xaa = Ile, Thr or Val
<220> FEATURE:
<221> NAME/KEY: VARIANT
<222> LOCATION: (14)...(14)
<223> OTHER INFORMATION: Xaa = Thr, Val, Leu or Pro
<220> FEATURE:
<221> NAME/KEY: VARIANT
<222> LOCATION: (15)...(15)
<223> OTHER INFORMATION: Xaa = Asn, Thr, Ala or Glu
<220> FEATURE:
<221> NAME/KEY: VARIANT
<222> LOCATION: (16)...(16)
<223> OTHER INFORMATION: Xaa = Phe or Tyr
<220> FEATURE:
<221> NAME/KEY: VARIANT
<222> LOCATION: (17)...(17)
<223> OTHER INFORMATION: Xaa = His, Pro, Asp, Ser, Gln or Ala
<220> FEATURE:
<221> NAME/KEY: VARIANT
<222> LOCATION: (18)...(18)
<223> OTHER INFORMATION: Xaa = Ala or Val
<220> FEATURE:
<221> NAME/KEY: VARIANT
<222> LOCATION: (19)...(19)
<223> OTHER INFORMATION: Xaa = Asn or Ser
<220> FEATURE:
<221> NAME/KEY: VARIANT
<222> LOCATION: (20)...(20)
<223> OTHER INFORMATION: Xaa = Asn, Leu, Asp or Val

<400> SEQUENCE: 10

Gly Ala Asp Gly Ser Xaa Xaa Xaa Xaa Xaa Xaa Xaa Glu Xaa Xaa Xaa
1               5                   10                  15

Xaa Xaa Xaa Xaa Gly
            20

<210> SEQ ID NO 11
<211> LENGTH: 21
<212> TYPE: PRT
<213> ORGANISM: Artificial Sequence
<220> FEATURE:
<223> OTHER INFORMATION: synthetic manganese peroxidase unmodified form
        active site domain "Motif C"
<220> FEATURE:
<221> NAME/KEY: VARIANT
<222> LOCATION: (1)...(1)
<223> OTHER INFORMATION: Xaa = Ala or Gly
<220> FEATURE:

-continued

```
<221> NAME/KEY: VARIANT
<222> LOCATION: (2)...(2)
<223> OTHER INFORMATION: Xaa = Gly or Ala
<220> FEATURE:
<221> NAME/KEY: VARIANT
<222> LOCATION: (3)...(3)
<223> OTHER INFORMATION: Xaa = Ala or Thr
<220> FEATURE:
<221> NAME/KEY: VARIANT
<222> LOCATION: (4)...(4)
<223> OTHER INFORMATION: Xaa = Val, Ile or Leu
<220> FEATURE:
<221> NAME/KEY: VARIANT
<222> LOCATION: (5)...(5)
<223> OTHER INFORMATION: Xaa = Gly or Ala
<220> FEATURE:
<221> NAME/KEY: VARIANT
<222> LOCATION: (6)...(6)
<223> OTHER INFORMATION: Xaa = Val, Thr or Leu
<220> FEATURE:
<221> NAME/KEY: VARIANT
<222> LOCATION: (7)...(7)
<223> OTHER INFORMATION: Xaa = Ser, Thr, Ala or Gly
<220> FEATURE:
<221> NAME/KEY: VARIANT
<222> LOCATION: (8)...(8)
<223> OTHER INFORMATION: Xaa = Asn or Leu
<220> FEATURE:
<221> NAME/KEY: VARIANT
<222> LOCATION: (10)...(10)
<223> OTHER INFORMATION: Xaa = Pro or Asn
<220> FEATURE:
<221> NAME/KEY: VARIANT
<222> LOCATION: (12)...(12)
<223> OTHER INFORMATION: Xaa = Ala or Gly
<220> FEATURE:
<221> NAME/KEY: VARIANT
<222> LOCATION: (14)...(14)
<223> OTHER INFORMATION: Xaa = Ala, Gln or Arg
<220> FEATURE:
<221> NAME/KEY: VARIANT
<222> LOCATION: (15)...(15)
<223> OTHER INFORMATION: Xaa = Leu or absent
<220> FEATURE:
<221> NAME/KEY: VARIANT
<222> LOCATION: (16)...(16)
<223> OTHER INFORMATION: Xaa = Pro, Asp, Ser, Gln or Glu
<220> FEATURE:
<221> NAME/KEY: VARIANT
<222> LOCATION: (17)...(17)
<223> OTHER INFORMATION: Xaa = Val, Phe, Tyr or Leu
<220> FEATURE:
<221> NAME/KEY: VARIANT
<222> LOCATION: (18)...(18)
<223> OTHER INFORMATION: Xaa = Phe, Met, Leu or Arg
<220> FEATURE:
<221> NAME/KEY: VARIANT
<222> LOCATION: (19)...(19)
<223> OTHER INFORMATION: Xaa = Val, Ile, Leu, Ala or Phe

<400> SEQUENCE: 11

Xaa Xaa Xaa Xaa Xaa Xaa Xaa Xaa Cys Xaa Gly Xaa Pro Xaa Xaa Xaa
1               5                   10                  15

Xaa Xaa Xaa Gly Arg
            20

<210> SEQ ID NO 12
<211> LENGTH: 21
<212> TYPE: PRT
<213> ORGANISM: Artificial Sequence
<220> FEATURE:
<223> OTHER INFORMATION: synthetic manganese peroxidase unmodified form
      active site domain "Motif D"
<220> FEATURE:
<221> NAME/KEY: VARIANT
<222> LOCATION: (3)...(3)
<223> OTHER INFORMATION: Xaa = Ala, Val or Ser
```

```
<220> FEATURE:
<221> NAME/KEY: VARIANT
<222> LOCATION: (4)...(4)
<223> OTHER INFORMATION: Xaa = Ser or Ala
<220> FEATURE:
<221> NAME/KEY: VARIANT
<222> LOCATION: (6)...(6)
<223> OTHER INFORMATION: Xaa = Ser or Thr
<220> FEATURE:
<221> NAME/KEY: VARIANT
<222> LOCATION: (7)...(7)
<223> OTHER INFORMATION: Xaa = Ile or Val
<220> FEATURE:
<221> NAME/KEY: VARIANT
<222> LOCATION: (8)...(8)
<223> OTHER INFORMATION: Xaa = Ala or Gly
<220> FEATURE:
<221> NAME/KEY: VARIANT
<222> LOCATION: (9)...(9)
<223> OTHER INFORMATION: Xaa = Ala, Ser, Asn or Arg
<220> FEATURE:
<221> NAME/KEY: VARIANT
<222> LOCATION: (10)...(10)
<223> OTHER INFORMATION: Xaa = Ala, Gln or Val
<220> FEATURE:
<221> NAME/KEY: VARIANT
<222> LOCATION: (11)...(11)
<223> OTHER INFORMATION: Xaa = Asp, Asn or Val
<220> FEATURE:
<221> NAME/KEY: VARIANT
<222> LOCATION: (12)...(12)
<223> OTHER INFORMATION: Xaa = His, Thr, Asp or Lys
<220> FEATURE:
<221> NAME/KEY: VARIANT
<222> LOCATION: (13)...(13)
<223> OTHER INFORMATION: Xaa = Val or Ile
<220> FEATURE:
<221> NAME/KEY: VARIANT
<222> LOCATION: (15)...(15)
<223> OTHER INFORMATION: Xaa = Pro, Glu, Ser or Gln
<220> FEATURE:
<221> NAME/KEY: VARIANT
<222> LOCATION: (16)...(16)
<223> OTHER INFORMATION: Xaa = Ser or Thr
<220> FEATURE:
<221> NAME/KEY: VARIANT
<222> LOCATION: (17)...(17)
<223> OTHER INFORMATION: Xaa = Ile, Val or Leu
<220> FEATURE:
<221> NAME/KEY: VARIANT
<222> LOCATION: (18)...(18)
<223> OTHER INFORMATION: Xaa = Pro, Ala or Asp
<220> FEATURE:
<221> NAME/KEY: VARIANT
<222> LOCATION: (19)...(19)
<223> OTHER INFORMATION: Xaa = Gly or Ala
<220> FEATURE:
<221> NAME/KEY: VARIANT
<222> LOCATION: (20)...(20)
<223> OTHER INFORMATION: Xaa = Thr, Ala or Ile

<400> SEQUENCE: 12

Leu Leu Xaa Xaa His Xaa Xaa Xaa Xaa Xaa Xaa Xaa Xaa Asp Xaa Xaa
1               5                   10                  15

Xaa Xaa Xaa Xaa Pro
            20

<210> SEQ ID NO 13
<211> LENGTH: 21
<212> TYPE: PRT
<213> ORGANISM: Artificial Sequence
<220> FEATURE:
<223> OTHER INFORMATION: synthetic manganese peroxidase unmodified form
      active site domain "Motif E"
<220> FEATURE:
<221> NAME/KEY: VARIANT
<222> LOCATION: (6)...(6)
```

```
<223> OTHER INFORMATION: Xaa = Ser, His or Phe
<220> FEATURE:
<221> NAME/KEY: VARIANT
<222> LOCATION: (7)...(7)
<223> OTHER INFORMATION: Xaa = Glu, Leu or Ala
<220> FEATURE:
<221> NAME/KEY: VARIANT
<222> LOCATION: (8)...(8)
<223> OTHER INFORMATION: Xaa = Leu or Phe
<220> FEATURE:
<221> NAME/KEY: VARIANT
<222> LOCATION: (9)...(9)
<223> OTHER INFORMATION: Xaa = Ala or Ser
<220> FEATURE:
<221> NAME/KEY: VARIANT
<222> LOCATION: (10)...(10)
<223> OTHER INFORMATION: Xaa = Arg or His
<220> FEATURE:
<221> NAME/KEY: VARIANT
<222> LOCATION: (12)...(12)
<223> OTHER INFORMATION: Xaa = Ser, Asp, His, Pro or Glu
<220> FEATURE:
<221> NAME/KEY: VARIANT
<222> LOCATION: (15)...(15)
<223> OTHER INFORMATION: Xaa = Ala, Ser or Thr
<220> FEATURE:
<221> NAME/KEY: VARIANT
<222> LOCATION: (17)...(17)
<223> OTHER INFORMATION: Xaa = Glu, Ser, Ile or Thr
<220> FEATURE:
<221> NAME/KEY: VARIANT
<222> LOCATION: (20)...(20)
<223> OTHER INFORMATION: Xaa = Ser, Lys or Gly
<220> FEATURE:
<221> NAME/KEY: VARIANT
<222> LOCATION: (21)...(21)
<223> OTHER INFORMATION: Xaa = Phe or Met

<400> SEQUENCE: 13

Arg Leu Gln Ser Asp Xaa Xaa Xaa Xaa Xaa Asp Xaa Arg Thr Xaa Cys
1               5                  10                  15

Xaa Trp Gln Xaa Xaa
            20

<210> SEQ ID NO 14
<211> LENGTH: 21
<212> TYPE: PRT
<213> ORGANISM: Artificial Sequence
<220> FEATURE:
<223> OTHER INFORMATION: synthetic manganese peroxidase active site
      domain "Motif A"
<220> FEATURE:
<221> NAME/KEY: VARIANT
<222> LOCATION: (1)...(1)
<223> OTHER INFORMATION: Xaa = any amino acid other than Asp, His, Gly,
      Gln or Glu
<220> FEATURE:
<221> NAME/KEY: VARIANT
<222> LOCATION: (2)...(2)
<223> OTHER INFORMATION: Xaa = Gly, Asp or Asn
<220> FEATURE:
<221> NAME/KEY: VARIANT
<222> LOCATION: (3)...(3)
<223> OTHER INFORMATION: Xaa = Gly or absent
<220> FEATURE:
<221> NAME/KEY: VARIANT
<222> LOCATION: (4)...(4)
<223> OTHER INFORMATION: Xaa = Glu, Ala or Gln
<220> FEATURE:
<221> NAME/KEY: VARIANT
<222> LOCATION: (7)...(7)
<223> OTHER INFORMATION: Xaa = Glu or Phe
<220> FEATURE:
<221> NAME/KEY: VARIANT
<222> LOCATION: (8)...(8)
<223> OTHER INFORMATION: Xaa = Glu, Asp, Gly or Thr
<220> FEATURE:
```

```
<221> NAME/KEY: VARIANT
<222> LOCATION: (9)...(9)
<223> OTHER INFORMATION: Xaa = Val or Ala
<220> FEATURE:
<221> NAME/KEY: VARIANT
<222> LOCATION: (11)...(11)
<223> OTHER INFORMATION: Xaa = Glu or Thr
<220> FEATURE:
<221> NAME/KEY: VARIANT
<222> LOCATION: (12)...(12)
<223> OTHER INFORMATION: Xaa = Ser, Ala, Val or Ile
<220> FEATURE:
<221> NAME/KEY: VARIANT
<222> LOCATION: (13)...(13)
<223> OTHER INFORMATION: Xaa = Leu or Ile
<220> FEATURE:
<221> NAME/KEY: VARIANT
<222> LOCATION: (16)...(16)
<223> OTHER INFORMATION: Xaa = Thr or Ser

<400> SEQUENCE: 14

Xaa Xaa Xaa Xaa Cys Gly Xaa Xaa Xaa His Xaa Xaa Xaa Arg Leu Xaa
1               5                   10                  15

Phe His Asp Ala Ile
            20

<210> SEQ ID NO 15
<211> LENGTH: 21
<212> TYPE: PRT
<213> ORGANISM: Artificial Sequence
<220> FEATURE:
<223> OTHER INFORMATION: synthetic manganese peroxidase active site
      domain "Motif B"
<220> FEATURE:
<221> NAME/KEY: VARIANT
<222> LOCATION: (6)...(6)
<223> OTHER INFORMATION: Xaa = Ile, Val or Met
<220> FEATURE:
<221> NAME/KEY: VARIANT
<222> LOCATION: (7)...(7)
<223> OTHER INFORMATION: Xaa = Ala, Ile or Leu
<220> FEATURE:
<221> NAME/KEY: VARIANT
<222> LOCATION: (8)...(8)
<223> OTHER INFORMATION: Xaa = Ile, Leu, Thr or Ala
<220> FEATURE:
<221> NAME/KEY: VARIANT
<222> LOCATION: (9)...(9)
<223> OTHER INFORMATION: Xaa = Phe or His
<220> FEATURE:
<221> NAME/KEY: VARIANT
<222> LOCATION: (10)...(10)
<223> OTHER INFORMATION: Xaa = Ala, Glu, Ser, Asn or Pro
<220> FEATURE:
<221> NAME/KEY: VARIANT
<222> LOCATION: (11)...(11)
<223> OTHER INFORMATION: Xaa = Glu, Asp, Thr or Leu
<220> FEATURE:
<221> NAME/KEY: VARIANT
<222> LOCATION: (12)...(12)
<223> OTHER INFORMATION: Xaa = Ile, Thr or Val
<220> FEATURE:
<221> NAME/KEY: VARIANT
<222> LOCATION: (14)...(14)
<223> OTHER INFORMATION: Xaa = Thr, Val, Leu or Pro
<220> FEATURE:
<221> NAME/KEY: VARIANT
<222> LOCATION: (15)...(15)
<223> OTHER INFORMATION: Xaa = any amino acid other than Asn, Thr, Ala
      or Glu
<220> FEATURE:
<221> NAME/KEY: VARIANT
<222> LOCATION: (16)...(16)
<223> OTHER INFORMATION: Xaa = Phe or Tyr
<220> FEATURE:
<221> NAME/KEY: VARIANT
<222> LOCATION: (17)...(17)
```

```
<223> OTHER INFORMATION: Xaa = His, Pro, Asp, Ser, Gln or Ala
<220> FEATURE:
<221> NAME/KEY: VARIANT
<222> LOCATION: (18)...(18)
<223> OTHER INFORMATION: Xaa = Ala or Val
<220> FEATURE:
<221> NAME/KEY: VARIANT
<222> LOCATION: (19)...(19)
<223> OTHER INFORMATION: Xaa = Asn or Ser
<220> FEATURE:
<221> NAME/KEY: VARIANT
<222> LOCATION: (20)...(20)
<223> OTHER INFORMATION: Xaa = Asn, Leu, Asp or Val

<400> SEQUENCE: 15

Gly Ala Asp Gly Ser Xaa Xaa Xaa Xaa Xaa Xaa Glu Xaa Xaa Xaa
 1               5                  10                  15

Xaa Xaa Xaa Xaa Gly
             20

<210> SEQ ID NO 16
<211> LENGTH: 21
<212> TYPE: PRT
<213> ORGANISM: Artificial Sequence
<220> FEATURE:
<223> OTHER INFORMATION: synthetic manganese peroxidase active site
      domain "Motif B"
<220> FEATURE:
<221> NAME/KEY: VARIANT
<222> LOCATION: (6)...(6)
<223> OTHER INFORMATION: Xaa = Ile, Val or Met
<220> FEATURE:
<221> NAME/KEY: VARIANT
<222> LOCATION: (7)...(7)
<223> OTHER INFORMATION: Xaa = Ala, Ile or Leu
<220> FEATURE:
<221> NAME/KEY: VARIANT
<222> LOCATION: (8)...(8)
<223> OTHER INFORMATION: Xaa = Ile, Leu, Thr or Ala
<220> FEATURE:
<221> NAME/KEY: VARIANT
<222> LOCATION: (9)...(9)
<223> OTHER INFORMATION: Xaa = Phe or His
<220> FEATURE:
<221> NAME/KEY: VARIANT
<222> LOCATION: (10)...(10)
<223> OTHER INFORMATION: Xaa = Ala, Glu, Ser, Asn or Pro
<220> FEATURE:
<221> NAME/KEY: VARIANT
<222> LOCATION: (11)...(11)
<223> OTHER INFORMATION: Xaa = Glu, Asp, Thr or Leu
<220> FEATURE:
<221> NAME/KEY: VARIANT
<222> LOCATION: (12)...(12)
<223> OTHER INFORMATION: Xaa = Ile, Thr or Val
<220> FEATURE:
<221> NAME/KEY: VARIANT
<222> LOCATION: (14)...(14)
<223> OTHER INFORMATION: Xaa = Thr, Val, Leu or Pro
<220> FEATURE:
<221> NAME/KEY: VARIANT
<222> LOCATION: (15)...(15)
<223> OTHER INFORMATION: Xaa = Asn, Thr, Ala or Glu
<220> FEATURE:
<221> NAME/KEY: VARIANT
<222> LOCATION: (16)...(16)
<223> OTHER INFORMATION: Xaa = Phe or Tyr
<220> FEATURE:
<221> NAME/KEY: VARIANT
<222> LOCATION: (17)...(17)
<223> OTHER INFORMATION: Xaa = any amino acid other than His, Pro, Asp,
      Ser, Gln or Ala
<220> FEATURE:
<221> NAME/KEY: VARIANT
<222> LOCATION: (18)...(18)
<223> OTHER INFORMATION: Xaa = Ala or Val
<220> FEATURE:
```

```
<221> NAME/KEY: VARIANT
<222> LOCATION: (19)...(19)
<223> OTHER INFORMATION: Xaa = Asn or Ser
<220> FEATURE:
<221> NAME/KEY: VARIANT
<222> LOCATION: (20)...(20)
<223> OTHER INFORMATION: Xaa = Asn, Leu, Asp or Val

<400> SEQUENCE: 16

Gly Ala Asp Gly Ser Xaa Xaa Xaa Xaa Xaa Xaa Xaa Glu Xaa Xaa Xaa
1               5                   10                  15

Xaa Xaa Xaa Xaa Gly
            20

<210> SEQ ID NO 17
<211> LENGTH: 21
<212> TYPE: PRT
<213> ORGANISM: Artificial Sequence
<220> FEATURE:
<223> OTHER INFORMATION: synthetic manganese peroxidase active site
      domain "Motif B"
<220> FEATURE:
<221> NAME/KEY: VARIANT
<222> LOCATION: (6)...(6)
<223> OTHER INFORMATION: Xaa = Ile, Val or Met
<220> FEATURE:
<221> NAME/KEY: VARIANT
<222> LOCATION: (7)...(7)
<223> OTHER INFORMATION: Xaa = Ala, Ile or Leu
<220> FEATURE:
<221> NAME/KEY: VARIANT
<222> LOCATION: (8)...(8)
<223> OTHER INFORMATION: Xaa = Ile, Leu, Thr or Ala
<220> FEATURE:
<221> NAME/KEY: VARIANT
<222> LOCATION: (9)...(9)
<223> OTHER INFORMATION: Xaa = Phe or His
<220> FEATURE:
<221> NAME/KEY: VARIANT
<222> LOCATION: (10)...(10)
<223> OTHER INFORMATION: Xaa = Ala, Glu, Ser, Asn or Pro
<220> FEATURE:
<221> NAME/KEY: VARIANT
<222> LOCATION: (11)...(11)
<223> OTHER INFORMATION: Xaa = Glu, Asp, Thr or Leu
<220> FEATURE:
<221> NAME/KEY: VARIANT
<222> LOCATION: (12)...(12)
<223> OTHER INFORMATION: Xaa = Ile, Thr or Val
<220> FEATURE:
<221> NAME/KEY: VARIANT
<222> LOCATION: (14)...(14)
<223> OTHER INFORMATION: Xaa = Thr, Val, Leu or Pro
<220> FEATURE:
<221> NAME/KEY: VARIANT
<222> LOCATION: (15)...(15)
<223> OTHER INFORMATION: Xaa = Asn, Thr, Ala or Glu
<220> FEATURE:
<221> NAME/KEY: VARIANT
<222> LOCATION: (16)...(16)
<223> OTHER INFORMATION: Xaa = Phe or Tyr
<220> FEATURE:
<221> NAME/KEY: VARIANT
<222> LOCATION: (17)...(17)
<223> OTHER INFORMATION: Xaa = His, Pro, Asp, Ser, Gln or Ala
<220> FEATURE:
<221> NAME/KEY: VARIANT
<222> LOCATION: (18)...(18)
<223> OTHER INFORMATION: Xaa = Ala or Val
<220> FEATURE:
<221> NAME/KEY: VARIANT
<222> LOCATION: (19)...(19)
<223> OTHER INFORMATION: Xaa = any amino acid other than Asn or Ser
<220> FEATURE:
<221> NAME/KEY: VARIANT
<222> LOCATION: (20)...(20)
<223> OTHER INFORMATION: Xaa = Asn, Leu, Asp or Val
```

<400> SEQUENCE: 17

Gly Ala Asp Gly Ser Xaa Xaa Xaa Xaa Xaa Xaa Xaa Glu Xaa Xaa Xaa
1               5                   10                  15

Xaa Xaa Xaa Xaa Gly
            20

<210> SEQ ID NO 18
<211> LENGTH: 21
<212> TYPE: PRT
<213> ORGANISM: Artificial Sequence
<220> FEATURE:
<223> OTHER INFORMATION: synthetic manganese peroxidase active site
      domain "Motif C"
<220> FEATURE:
<221> NAME/KEY: VARIANT
<222> LOCATION: (1)...(1)
<223> OTHER INFORMATION: Xaa = Ala or Gly
<220> FEATURE:
<221> NAME/KEY: VARIANT
<222> LOCATION: (2)...(2)
<223> OTHER INFORMATION: Xaa = Gly or Ala
<220> FEATURE:
<221> NAME/KEY: VARIANT
<222> LOCATION: (3)...(3)
<223> OTHER INFORMATION: Xaa = Ala or Thr
<220> FEATURE:
<221> NAME/KEY: VARIANT
<222> LOCATION: (4)...(4)
<223> OTHER INFORMATION: Xaa = Val, Ile or Leu
<220> FEATURE:
<221> NAME/KEY: VARIANT
<222> LOCATION: (5)...(5)
<223> OTHER INFORMATION: Xaa = Gly or Ala
<220> FEATURE:
<221> NAME/KEY: VARIANT
<222> LOCATION: (6)...(6)
<223> OTHER INFORMATION: Xaa = Val, Thr or Leu
<220> FEATURE:
<221> NAME/KEY: VARIANT
<222> LOCATION: (7)...(7)
<223> OTHER INFORMATION: Xaa = Ser, Thr, Ala or Gly
<220> FEATURE:
<221> NAME/KEY: VARIANT
<222> LOCATION: (8)...(8)
<223> OTHER INFORMATION: Xaa = Asn or Leu
<220> FEATURE:
<221> NAME/KEY: VARIANT
<222> LOCATION: (10)...(10)
<223> OTHER INFORMATION: Xaa = Pro or Asn
<220> FEATURE:
<221> NAME/KEY: VARIANT
<222> LOCATION: (12)...(12)
<223> OTHER INFORMATION: Xaa = Ala or Gly
<220> FEATURE:
<221> NAME/KEY: VARIANT
<222> LOCATION: (14)...(14)
<223> OTHER INFORMATION: Xaa = any amino acid other than Ala, Gln or Arg
<220> FEATURE:
<221> NAME/KEY: VARIANT
<222> LOCATION: (15)...(15)
<223> OTHER INFORMATION: Xaa = Leu or absent
<220> FEATURE:
<221> NAME/KEY: VARIANT
<222> LOCATION: (16)...(16)
<223> OTHER INFORMATION: Xaa = Pro, Asp, Ser, Gln or Glu
<220> FEATURE:
<221> NAME/KEY: VARIANT
<222> LOCATION: (17)...(17)
<223> OTHER INFORMATION: Xaa = Val, Phe, Tyr or Leu
<220> FEATURE:
<221> NAME/KEY: VARIANT
<222> LOCATION: (18)...(18)
<223> OTHER INFORMATION: Xaa = Phe, Met, Leu or Arg
<220> FEATURE:
<221> NAME/KEY: VARIANT
<222> LOCATION: (19)...(19)

-continued

<223> OTHER INFORMATION: Xaa = Val, Ile, Leu, Ala or Phe

<400> SEQUENCE: 18

Xaa Xaa Xaa Xaa Xaa Xaa Xaa Xaa Cys Xaa Gly Xaa Pro Xaa Xaa Xaa
1               5                   10                  15

Xaa Xaa Xaa Gly Arg
            20

<210> SEQ ID NO 19
<211> LENGTH: 21
<212> TYPE: PRT
<213> ORGANISM: Artificial Sequence
<220> FEATURE:
<223> OTHER INFORMATION: synthetic manganese peroxidase active site
      domain "Motif D"
<220> FEATURE:
<221> NAME/KEY: VARIANT
<222> LOCATION: (3)...(3)
<223> OTHER INFORMATION: Xaa = Ala, Val or Ser
<220> FEATURE:
<221> NAME/KEY: VARIANT
<222> LOCATION: (4)...(4)
<223> OTHER INFORMATION: Xaa = Ser or Ala
<220> FEATURE:
<221> NAME/KEY: VARIANT
<222> LOCATION: (6)...(6)
<223> OTHER INFORMATION: Xaa = any amino acid other than Ser or Thr
<220> FEATURE:
<221> NAME/KEY: VARIANT
<222> LOCATION: (7)...(7)
<223> OTHER INFORMATION: Xaa = Ile or Val
<220> FEATURE:
<221> NAME/KEY: VARIANT
<222> LOCATION: (8)...(8)
<223> OTHER INFORMATION: Xaa = Ala or Gly
<220> FEATURE:
<221> NAME/KEY: VARIANT
<222> LOCATION: (9)...(9)
<223> OTHER INFORMATION: Xaa = Ala, Ser, Asn or Arg
<220> FEATURE:
<221> NAME/KEY: VARIANT
<222> LOCATION: (10)...(10)
<223> OTHER INFORMATION: Xaa = Ala, Gln or Val
<220> FEATURE:
<221> NAME/KEY: VARIANT
<222> LOCATION: (11)...(11)
<223> OTHER INFORMATION: Xaa = Asp, Asn or Val
<220> FEATURE:
<221> NAME/KEY: VARIANT
<222> LOCATION: (12)...(12)
<223> OTHER INFORMATION: Xaa = His, Thr, Asp or Lys
<220> FEATURE:
<221> NAME/KEY: VARIANT
<222> LOCATION: (13)...(13)
<223> OTHER INFORMATION: Xaa = Val or Ile
<220> FEATURE:
<221> NAME/KEY: VARIANT
<222> LOCATION: (15)...(15)
<223> OTHER INFORMATION: Xaa = Pro, Glu, Ser or Gln
<220> FEATURE:
<221> NAME/KEY: VARIANT
<222> LOCATION: (16)...(16)
<223> OTHER INFORMATION: Xaa = Ser or Thr
<220> FEATURE:
<221> NAME/KEY: VARIANT
<222> LOCATION: (17)...(17)
<223> OTHER INFORMATION: Xaa = Ile, Val or Leu
<220> FEATURE:
<221> NAME/KEY: VARIANT
<222> LOCATION: (18)...(18)
<223> OTHER INFORMATION: Xaa = Pro, Ala or Asp
<220> FEATURE:
<221> NAME/KEY: VARIANT
<222> LOCATION: (19)...(19)
<223> OTHER INFORMATION: Xaa = Gly or Ala
<220> FEATURE:
<221> NAME/KEY: VARIANT -continued

```
<222> LOCATION: (20)...(20)
<223> OTHER INFORMATION: Xaa = Thr, Ala or Ile

<400> SEQUENCE: 19

Leu Leu Xaa Xaa His Xaa Xaa Xaa Xaa Xaa Xaa Xaa Xaa Asp Xaa Xaa
1               5                   10                  15

Xaa Xaa Xaa Xaa Pro
            20

<210> SEQ ID NO 20
<211> LENGTH: 21
<212> TYPE: PRT
<213> ORGANISM: Artificial Sequence
<220> FEATURE:
<223> OTHER INFORMATION: synthetic manganese peroxidase active site
      domain "Motif E"
<220> FEATURE:
<221> NAME/KEY: VARIANT
<222> LOCATION: (6)...(6)
<223> OTHER INFORMATION: Xaa = Ser, His or Phe
<220> FEATURE:
<221> NAME/KEY: VARIANT
<222> LOCATION: (7)...(7)
<223> OTHER INFORMATION: Xaa = Glu, Leu or Ala
<220> FEATURE:
<221> NAME/KEY: VARIANT
<222> LOCATION: (8)...(8)
<223> OTHER INFORMATION: Xaa = Leu or Phe
<220> FEATURE:
<221> NAME/KEY: VARIANT
<222> LOCATION: (9)...(9)
<223> OTHER INFORMATION: Xaa = Ala or Ser
<220> FEATURE:
<221> NAME/KEY: VARIANT
<222> LOCATION: (10)...(10)
<223> OTHER INFORMATION: Xaa = Arg or His
<220> FEATURE:
<221> NAME/KEY: VARIANT
<222> LOCATION: (12)...(12)
<223> OTHER INFORMATION: Xaa = Ser, Asp, His, Pro or Glu
<220> FEATURE:
<221> NAME/KEY: VARIANT
<222> LOCATION: (15)...(15)
<223> OTHER INFORMATION: Xaa = Ala, Ser or Thr
<220> FEATURE:
<221> NAME/KEY: VARIANT
<222> LOCATION: (17)...(17)
<223> OTHER INFORMATION: Xaa = Glu, Ser, Ile or Thr
<220> FEATURE:
<221> NAME/KEY: VARIANT
<222> LOCATION: (18)...(18)
<223> OTHER INFORMATION: Xaa = any amino acid other than Trp
<220> FEATURE:
<221> NAME/KEY: VARIANT
<222> LOCATION: (20)...(20)
<223> OTHER INFORMATION: Xaa = Ser, Lys or Gly
<220> FEATURE:
<221> NAME/KEY: VARIANT
<222> LOCATION: (21)...(21)
<223> OTHER INFORMATION: Xaa = Phe or Met

<400> SEQUENCE: 20

Arg Leu Gln Ser Asp Xaa Xaa Xaa Xaa Xaa Asp Xaa Arg Thr Xaa Cys
1               5                   10                  15

Xaa Xaa Gln Xaa Xaa
            20

<210> SEQ ID NO 21
<211> LENGTH: 364
<212> TYPE: PRT
<213> ORGANISM: Ganoderma austral
<220> FEATURE:
<223> OTHER INFORMATION: Ganoderma austral wild-type fungus manganese
      peroxidase (MnP, mnp)
```

<400> SEQUENCE: 21

```
Met Phe Ser Lys Val Phe Leu Ser Leu Val Leu Ala Ser Ser Val
1               5                   10                  15

Ala Ala Ala Val Pro Ser Val Gly Arg Arg Ala Thr Cys Ala Asn Gly
            20                  25                  30

Lys Thr Thr Ala Asn Asp Ala Cys Cys Val Trp Phe Asp Val Leu Asp
                35                  40                  45

Asp Ile Gln Glu Asn Leu Phe His Gly Gly Gln Cys Gly Glu Asp Ala
50                  55                  60

His Glu Ser Leu Arg Leu Thr Phe His Asp Ala Ile Ala Phe Ser Pro
65                  70                  75                  80

Ala Leu Thr Ala Ala Gly Gln Phe Gly Gly Gly Ala Asp Gly Ser
                85                  90                  95

Ile Ile Ala His Ser Asp Val Glu Leu Thr Tyr Pro Val Asn Asp Gly
            100                 105                 110

Leu Asp Glu Ile Val Glu Ala Ser Arg Pro Phe Ala Ile Lys His Asn
        115                 120                 125

Val Ser Phe Gly Asp Phe Ile Gln Phe Ala Gly Ala Val Gly Val Ala
    130                 135                 140

Asn Cys Asn Gly Gly Pro Gln Leu Ser Phe Phe Ala Gly Arg Ser Asn
145                 150                 155                 160

Asp Ser Gln Pro Ser Pro Pro Asn Leu Val Pro Leu Pro Ser Asp Thr
                165                 170                 175

Ala Asp Thr Ile Leu Ser Arg Phe Ser Asp Ala Gly Phe Asp Ser Val
            180                 185                 190

Glu Val Val Trp Leu Leu Val Pro His Thr Val Gly Ser Gln Asn Thr
        195                 200                 205

Val Asp Pro Ser Ile Pro Gly Ala Pro Phe Asp Ser Thr Pro Ser Asp
    210                 215                 220

Phe Asp Ala Gln Phe Phe Val Glu Thr Met Leu Asn Gly Thr Leu Val
225                 230                 235                 240

Pro Gly Asn Gly Leu Gln Asp Gly Glu Val Leu Ser Pro Tyr Pro Gly
                245                 250                 255

Glu Phe Arg Leu Gln Ser Asp Phe Ala Leu Ser Arg Asp Ser Arg Thr
            260                 265                 270

Thr Cys Glu Trp Gln Lys Met Ile Ala Asp Arg Ala Asn Met Leu Glu
        275                 280                 285

Lys Phe Glu Ile Thr Met Leu Lys Met Ser Leu Leu Gly Phe Asp Gln
    290                 295                 300

Ser Ala Leu Thr Asp Cys Ser Asp Val Ile Pro Thr Ala Thr Gly Thr
305                 310                 315                 320

Val Gln Asp Pro Phe Ile Pro Ala Gly Leu Thr Val Asp Asp Leu Gln
                325                 330                 335

Pro Ala Cys Ser Ser Ser Ala Phe Pro Thr Val Thr Val Ala Gly
            340                 345                 350

Ala Val Thr Ser Ile Pro Ala Val Pro Leu Asn Ser
        355                 360
```

<210> SEQ ID NO 22
<211> LENGTH: 364
<212> TYPE: PRT
<213> ORGANISM: Ganoderma formosanum
<220> FEATURE:
<223> OTHER INFORMATION: Ganoderma formosanum wild-type fungus manganese peroxidase (mnp0109)

<400> SEQUENCE: 22

```
Met Phe Ser Lys Val Phe Leu Ser Leu Val Leu Ala Ala Ser Ala
1               5                   10                  15

Ala Ala Ala Val Pro Ser Val Ser Arg Arg Ala Thr Cys Ser Asn Gly
            20                  25                  30

Lys Thr Thr Ala Asn Asp Ala Cys Cys Val Trp Phe Asp Val Leu Asp
                35                  40                  45

Asp Ile Gln Glu Asn Leu Phe His Gly Gly Gln Cys Gly Glu Asp Ala
        50                  55                  60

His Glu Ser Leu Arg Leu Thr Phe His Asp Ala Ile Gly Phe Ser Pro
65                  70                  75                  80

Ala Leu Thr Ala Ala Gly Gln Phe Gly Gly Gly Ala Asp Gly Ser
                85                  90                  95

Ile Ile Ala His Ser Asp Val Glu Met Thr Tyr Pro Ala Asn Asp Gly
                100                 105                 110

Leu Asp Glu Ile Ile Glu Ala Ser Arg Pro Phe Ala Ile Lys His Asn
            115                 120                 125

Val Ser Phe Gly Asp Phe Ile Gln Phe Ala Gly Ala Val Gly Val Ala
130                 135                 140

Asn Cys Asn Gly Gly Pro Gln Leu Ser Phe Phe Ala Gly Arg Ser Asn
145                 150                 155                 160

Asp Ser Gln Pro Ser Pro Pro Asn Leu Val Pro Leu Pro Ser Asp Ser
                165                 170                 175

Ala Asp Ser Ile Leu Ser Arg Phe Ser Asp Ala Gly Phe Ala Ser Val
            180                 185                 190

Glu Val Val Trp Leu Leu Val Ser His Thr Val Gly Ser Gln Asn Thr
            195                 200                 205

Val Asp Pro Ser Ile Pro Gly Ala Pro Phe Asp Ser Thr Pro Ser Asp
210                 215                 220

Phe Asp Ala Gln Phe Phe Val Glu Thr Met Leu Asn Gly Thr Leu Val
225                 230                 235                 240

Pro Gly Asp Ala Leu His Asp Gly Glu Val Asn Ser Pro Tyr Pro Gly
                245                 250                 255

Glu Phe Arg Leu Gln Ser Asp Phe Ala Leu Ser Arg Asp Ser Arg Thr
            260                 265                 270

Ala Cys Glu Trp Gln Lys Met Ile Ala Asp Arg Ala Asn Met Leu Glu
        275                 280                 285

Lys Phe Glu Val Thr Met Leu Lys Met Ser Leu Leu Gly Phe Asn Gln
290                 295                 300

Ser Met Leu Thr Asp Cys Ser Asp Val Ile Pro Thr Ala Thr Gly Thr
305                 310                 315                 320

Val Gln Asp Pro Phe Ile Pro Ala Gly Leu Thr Val Asp Asp Leu Gln
                325                 330                 335

Pro Ala Cys Ser Ser Thr Ala Phe Pro Thr Val Asn Thr Val Ala Gly
            340                 345                 350

Ala Val Thr Ser Ile Pro Ala Val Pro Leu Asn Ser
            355                 360
```

<210> SEQ ID NO 23
<211> LENGTH: 381
<212> TYPE: PRT
<213> ORGANISM: Phanerochaete sordida
<220> FEATURE:
<223> OTHER INFORMATION: Phanerochaete sordida strain YK-624 wild-type
fungus manganese peroxidase isoform 4 (mnp4)

```
<400> SEQUENCE: 23

Met Ala Phe Ser Thr Leu Leu Ala Phe Val Ala Phe Ala Ala Val Thr
 1               5                  10                  15

Arg Ala Ala Pro Thr Thr Asp Ser Ala Val Cys Pro Asp Gly Thr Arg
                20                  25                  30

Val Asn Asn Ala Ala Cys Cys Ala Phe Val Pro Leu Ala Gln Asp Leu
            35                  40                  45

Gln Ala Asn Leu Phe Gln Asn Asp Cys Gly Glu Asp Ala His Glu Val
50                  55                  60

Ile Arg Leu Thr Phe His Asp Ala Ile Ala Ile Ser Gln Ser Gln Gly
65                  70                  75                  80

Pro Lys Ala Gly Gly Gly Ala Asp Gly Ser Met Leu Leu Phe Pro Thr
                85                  90                  95

Ile Glu Pro Asn Phe Glu Ala Asn Asn Gly Ile Asp Asp Ser Val Asn
                100                 105                 110

Asn Leu Ile Pro Phe Met Gln Thr His Asn Thr Ile Ser Ala Gly Asp
            115                 120                 125

Leu Val Gln Phe Ala Gly Ala Val Ala Leu Ala Asn Cys Pro Gly Ala
130                 135                 140

Pro Arg Leu Glu Phe Leu Ala Gly Arg Pro Asn Lys Thr Ile Ala Ala
145                 150                 155                 160

Val Glu Gly Leu Ile Pro Glu Pro Gln Asp Ser Val Thr Ser Ile Leu
                165                 170                 175

Gln Arg Phe Glu Asp Ala Gly Asn Phe Ser Pro Phe Glu Val Val Ser
            180                 185                 190

Leu Leu Ala Ser His Ser Ile Ala Arg Ala Asp Lys Val Asp Glu Thr
        195                 200                 205

Ile Asp Ala Ala Pro Phe Asp Ser Thr Pro Phe Thr Phe Asp Thr Gln
210                 215                 220

Val Phe Leu Glu Val Leu Leu Lys Gly Val Gly Phe Pro Gly Thr Ala
225                 230                 235                 240

Asn Asn Thr Gly Glu Val Thr Ser Pro Leu Pro Asn Thr Ser Gly Thr
                245                 250                 255

Asp Thr Gly Glu Met Arg Leu Gln Ser Asp Phe Ala Leu Ala Arg Asp
            260                 265                 270

Ser Arg Thr Ala Cys Phe Trp Gln Gly Phe Val Asn Glu Gln Ala Phe
        275                 280                 285

Met Ala Ser Ser Phe Arg Ala Ala Met Ser Lys Leu Ala Val Leu Gly
290                 295                 300

His Asn Arg Asn Ser Leu Ile Asp Cys Ser Asp Val Val Pro Gln Pro
305                 310                 315                 320

Lys Pro Ala Val Asn Lys Pro Ala Thr Phe Pro Ala Ser Thr Gly Pro
                325                 330                 335

Gln Asp Leu Gln Leu Ser Cys Pro Thr Ala Lys Phe Pro Thr Leu Thr
            340                 345                 350

Thr Asp Pro Gly Ala Ser Glu Thr Leu Ile Pro His Cys Ser Asn Gly
        355                 360                 365

Gly Met Ser Cys Pro Ala Ile Gln Phe Asp Gly Pro Ala
370                 375                 380

<210> SEQ ID NO 24
<211> LENGTH: 354
<212> TYPE: PRT
<213> ORGANISM: Agaricus bisporus
```

<220> FEATURE:
<223> OTHER INFORMATION: Agaricus bisporus strain ATCC 62459 wild-type
    fungus manganese peroxidase enzyme (mnp1), ligninolytic enzyme

<400> SEQUENCE: 24

Met Ala Phe Lys Ile Leu Leu Ser Leu Ile Leu Ala Leu Asn Ala Val
1               5                   10                  15

Gln Phe Ile Ala Ala Val Pro Thr Arg Arg Ala Gln Cys Ala Asp Gly
            20                  25                  30

Thr Thr Val Ser Asn Glu Ala Cys Cys Val Leu Leu Pro Ile Ile Ala
        35                  40                  45

Asp Ile Gln Pro Asn Leu Phe Glu Asn Glu Cys Gly Glu Glu Val His
    50                  55                  60

Glu Thr Leu Arg Ala Ser Phe His Asp Ala Ile Gly Phe Ser Arg Ala
65                  70                  75                  80

Ala Gly Gly Gly Ala Asp Gly Ser Leu Val Thr Phe Gly Asp Val
                85                  90                  95

Glu Thr Phe Ala Ala Asn Ala Gly Ile Asp Glu Ile Val Glu Thr
            100                 105                 110

Leu Arg Pro Phe Ile Asn Ser His Asn Ile Ser Ala Gly Asp Phe Ile
            115                 120                 125

Gln Phe Ala Thr Val Val Gly Leu Thr Asn Cys Pro Gly Ala Pro Arg
130                 135                 140

Ile Pro Phe Phe Leu Gly Arg Pro Asp Ala Thr Ala Ala Ser Pro Asp
145                 150                 155                 160

Gly Leu Val Pro Glu Pro Phe Asp Ser Val Thr Lys Ile Leu Glu Arg
                165                 170                 175

Phe Asp Asp Ala Gly Phe Thr Pro Thr Glu Val Val Ala Leu Leu Ala
            180                 185                 190

Ser His Thr Val Ala Ala Ser Asp Thr Ile Glu Pro Gly Leu Glu Gly
            195                 200                 205

Val Pro Phe Asp Ser Thr Pro Gly Glu Phe Asp Arg Gln Phe Phe Ile
            210                 215                 220

Glu Thr Met Leu Lys Gly Thr Ser Phe Pro Gly Thr Gly Gly Asn Gln
225                 230                 235                 240

Gly Glu Ala Leu Ser Pro Leu Pro Gly Glu Leu Arg Leu Glu Ser Asp
                245                 250                 255

Gly Leu Leu Ala Arg Asp Glu Arg Thr Ala Cys Asp Trp Gln Leu Phe
            260                 265                 270

Ala Thr Asp Gln Gln Lys Met Ala Ser Ala Phe Ser Ala Met Val
            275                 280                 285

Lys Leu Ser Leu Val Gly Gln Asp Lys Ser Gln Leu Ile Asp Cys Ser
290                 295                 300

Asp Val Ile Pro Arg Thr Ile Pro Leu Thr Asn Glu Pro Tyr Phe Pro
305                 310                 315                 320

Ala Asp Leu Thr Lys Asp Asp Leu Glu Gln Thr Cys Pro Asp Glu Phe
                325                 330                 335

Pro Asp Tyr Pro Ser Asn Pro Ser Val Thr Ser Val Ala Pro Val Pro
            340                 345                 350

Thr Ser

<210> SEQ ID NO 25
<211> LENGTH: 365
<212> TYPE: PRT
<213> ORGANISM: Phlebia sp.
<220> FEATURE:

<223> OTHER INFORMATION: Phlebia sp. MG60 wild-type white-rot fungus
      manganese peroxidase 1 (mnp1)

<400> SEQUENCE: 25

```
Met Ala Phe Arg Gln Leu Leu Thr Ala Ile Ser Val Ala Leu Thr Cys
1               5                   10                  15

Ser Ala Ala Asn Ala Ala Leu Thr Arg Arg Val Ala Cys Pro Asp Gly
                20                  25                  30

Lys Asn Thr Ala Thr Asn Ala Ala Cys Cys Ser Leu Phe Ala Val Arg
            35                  40                  45

Asp Leu Ile Gln Asp Gln Leu Phe Asp Gly Gly Glu Cys Gly Glu Glu
        50                  55                  60

Val His Glu Ser Leu Arg Leu Thr Phe His Asp Ala Ile Gly Ile Ser
65                  70                  75                  80

Pro Ser Ile Gln Lys Thr Gly Val Phe Gly Gly Gly Ala Asp Gly
                85                  90                  95

Ser Ile Ala Ile Phe Glu Asp Ile Glu Thr Asn Phe His Ala Asn Asn
                100                 105                 110

Gly Val Asp Glu Ile Ile Asp Glu Gln Arg Pro Phe Val Gln Met Ser
            115                 120                 125

Asn Met Thr Thr Ala Asp Phe Ile Gln Phe Ala Gly Ala Val Gly Val
        130                 135                 140

Ser Asn Cys Pro Gly Ala Pro Ser Leu Pro Val Phe Ile Gly Arg Ala
145                 150                 155                 160

Asp Ala Thr Gln Pro Ala Pro Asp Lys Thr Val Pro Glu Pro Phe Asp
                165                 170                 175

Thr Val Asp Ser Ile Leu Ala Arg Phe Ala Asp Ala Gly Gly Phe Thr
            180                 185                 190

Ser Ala Glu Val Val Ala Leu Leu Ala Ser His Thr Ile Ala Ala Ala
        195                 200                 205

Asp His Val Asp Pro Ser Ile Pro Gly Thr Pro Phe Asp Ser Thr Pro
    210                 215                 220

Gly Ile Phe Asp Thr Gln Phe Phe Val Glu Thr Gln Leu Arg Gly Ile
225                 230                 235                 240

Leu Phe Pro Gly Thr Gly Gly Asn Gln Gly Glu Val Glu Ser Pro Leu
                245                 250                 255

His Gly Glu Leu Arg Leu Gln Ser Asp Ser Glu Leu Ala Arg Asp Ser
            260                 265                 270

Arg Thr Ala Cys Glu Trp Gln Ser Phe Val Asn Asn Gln Ala Lys Ile
        275                 280                 285

Gln Ser Ala Phe Lys Ala Ala Phe Arg Lys Met Thr Ile Leu Gly His
    290                 295                 300

Ser Glu Ser Ser Leu Ile Glu Cys Ser Glu Val Ile Glu Ala Pro Pro
305                 310                 315                 320

Ala Leu Lys Gly Asn Ala His Leu Pro Ala Gly Lys Thr Met Asn Asp
                325                 330                 335

Ile Glu Gln Ala Cys Ala Thr Thr Pro Phe Pro Ser Leu Ser Ala Asp
            340                 345                 350

Pro Gly Pro Ala Thr Ser Val Ala Pro Val Pro Pro Ser
        355                 360                 365
```

<210> SEQ ID NO 26
<211> LENGTH: 390
<212> TYPE: PRT
<213> ORGANISM: Phlebia sp.
<220> FEATURE:

<223> OTHER INFORMATION: Phlebia sp. MG60 wild-type white-rot fungus manganese peroxidase 2 (mnp2)

<400> SEQUENCE: 26

| Met | Ala | Phe | Asn | Phe | Ala | Ser | Ile | Leu | Ala | Phe | Val | Ser | Leu | Ala | Ala |
|---|---|---|---|---|---|---|---|---|---|---|---|---|---|---|---|
| 1 | | | | 5 | | | | | 10 | | | | | 15 | |

Val Ala Ser Ala Ala Pro Ser Gln Thr Ala Cys Ser Asp Gly Thr Val
           20            25            30

Val Pro Ser Ser Val Cys Cys Asp Phe Ile Pro Leu Ala Ala Ala Leu
    35              40              45

Gln Ser Gln Val Ile Gln Asn Asp Cys Gly Glu Asp Ala His Glu Leu
      50              55             60

Val Arg Leu Ile Phe His Asp Ala Ile Ser Ile Ser Arg Thr Arg Gly
65              70              75             80

Pro Ser Ala Gly Gly Ala Asp Gly Ser Met Leu Ile Phe Pro Thr
            85             90           95

Val Glu Pro Ala Phe Phe Ala Asn Leu Gly Ile Ala Asp Ser Val Asn
        100            105          110

Asn Leu Ile Pro Phe Leu Ser Gln Phe Pro Thr Ile Ser Thr Gly Asp
     115           120           125

Leu Val Gln Phe Ala Gly Ala Val Ala Ile Ser Asn Cys Pro Gly Ala
    130            135            140

Pro Arg Leu Glu Phe Leu Ala Gly Arg Pro Asn Ala Thr Ala Pro Ala
145            150            155          160

Ile Asp Gly Leu Ile Pro Glu Pro Gln Asp Ser Val Thr Ser Ile Leu
         165           170          175

Glu Arg Phe Asp Asp Ala Gly Gly Phe Thr Pro Glu Glu Val Val Ala
        180            185          190

Leu Leu Ala Ser His Ser Ile Ala Arg Ala Asp His Val Asp Pro Thr
    195            200           205

Leu Asp Ala Ala Pro Phe Asp Thr Thr Pro Phe Thr Phe Asp Thr Gln
   210            215           220

Ile Phe Leu Glu Val Leu Leu Lys Gly Val Gly Phe Pro Gly Leu Asn
225            230            235          240

Asn Asn Thr Gly Glu Val Ser Ser Pro Leu Pro Thr Thr Asp Gly Thr
        245            250          255

Asp Val Gly Glu Leu Arg Leu Gln Ser Asp Phe Ala Leu Ala Arg Asp
        260            265          270

Glu Arg Thr Ala Cys Ala Trp Gln Gly Phe Val Asn Glu Gln Glu Ala
    275            280           285

Met Ala Ile Ala Phe Lys Asn Ala Val Lys Lys Leu Ala Val Leu Gly
   290            295           300

His Asn Pro Ala Asp Leu Val Asn Cys Pro Leu Ser Ser Leu Tyr His
305            310            315          320

Ser Pro Pro Ser Ala Arg Arg Arg Pro Phe Pro Ala Thr Thr Gly Pro
        325            330          335

Gln Asp Leu Glu Leu Thr Cys Thr Thr Glu Lys Phe Pro Thr Leu Thr
        340            345          350

Thr Asp Glu Gly Ala Gln Glu Thr Leu Ile Pro His Cys Ser Asp Gly
    355            360           365

Ser Met Asn Cys Asp Ser Val Gln Phe Asp Gly Pro Ala Thr Asn Phe
   370            375           380

Gly Gly Glu Gly Asp Ser
385            390

-continued

```
<210> SEQ ID NO 27
<211> LENGTH: 364
<212> TYPE: PRT
<213> ORGANISM: Pleurotus sp.
<220> FEATURE:
<223> OTHER INFORMATION: Pleurotus sp. strain 'Florida' wild-type fungus
      manganese peroxidase 2 (mnp2)
<220> FEATURE:
<221> NAME/KEY: SIGNAL
<222> LOCATION: (1)...(27)
<223> OTHER INFORMATION: signal peptide
<220> FEATURE:
<221> NAME/KEY: PEPTIDE
<222> LOCATION: (28)...(364)
<223> OTHER INFORMATION: mature peptide

<400> SEQUENCE: 27

Met Ala Phe Ala Lys Leu Ser Ala Leu Val Leu Ala Leu Gly Ala Thr
1               5                   10                  15

Val Ala Leu Gly Ala Pro Ser Leu Asn Lys Arg Val Thr Cys Ala Thr
                20                  25                  30

Gly Gln Thr Thr Ala Asn Glu Ala Cys Cys Ala Leu Phe Pro Ile Leu
            35                  40                  45

Glu Asp Ile Gln Thr Asn Leu Phe Asp Gly Ala Gln Cys Gly Glu Glu
50                  55                  60

Val His Glu Ser Leu Arg Leu Thr Phe His Asp Ala Ile Ala Phe Ser
65                  70                  75                  80

Pro Ala Leu Thr Asn Ala Gly Gln Phe Gly Gly Gly Gly Ala Asp Gly
                85                  90                  95

Ser Met Ile Ile Phe Ser Asp Thr Glu Pro Asn Phe His Ala Asn Leu
            100                 105                 110

Gly Ile Asp Glu Ile Val Glu Ala Gln Lys Pro Phe Ile Ala Arg His
        115                 120                 125

Asn Ile Ser Ala Ala Asp Phe Ile Gln Phe Ala Gly Ala Ile Gly Val
    130                 135                 140

Thr Asn Cys Ala Gly Ala Pro Arg Leu Asn Phe Phe Leu Gly Arg Pro
145                 150                 155                 160

Asp Ala Thr Gln Ile Pro Pro Asp Gly Leu Val Pro Glu Pro Phe Asp
                165                 170                 175

Ser Val Asp Lys Ile Leu Ser Arg Met Gly Asp Ala Gly Phe Ser Thr
            180                 185                 190

Val Glu Val Val Trp Leu Leu Ser Ser His Thr Ile Ala Ala Ala Asp
        195                 200                 205

Leu Val Asp Pro Ser Ile Pro Gly Thr Pro Phe Asp Ser Thr Pro Ser
    210                 215                 220

Thr Phe Asp Ser Gln Phe Phe Leu Glu Thr Met Leu Gln Gly Thr Ala
225                 230                 235                 240

Phe Pro Gly Thr Pro Gly Asn Gln Gly Glu Val Glu Ser Pro Leu Ala
                245                 250                 255

Gly Glu Met Arg Leu Gln Ser Asp Phe Leu Leu Ala Arg Asp Ser Arg
            260                 265                 270

Ser Ala Cys Glu Trp Gln Ser Met Val Asn Asn Met Pro Lys Ile Gln
        275                 280                 285

Asn Arg Phe Thr Gln Val Met Arg Lys Leu Ser Leu Leu Gly His Asn
    290                 295                 300

Gln Ala Asp Leu Ile Asp Cys Ser Asp Val Ile Pro Val Pro Lys Thr
305                 310                 315                 320

Leu Thr Lys Ala Ala Thr Phe Pro Ala Gly Lys Ser Gln Ala Asp Val
```

```
                        325                 330                 335
Glu Ile Val Val Ala Ala Thr Pro Phe Pro Ala Leu Ala Ser Asp Pro
                340                 345                 350
Gly Pro Val Thr Ala Val Pro Pro Val Pro Pro Ser
            355                 360

<210> SEQ ID NO 28
<211> LENGTH: 371
<212> TYPE: PRT
<213> ORGANISM: Fomitiporia mediterranea
<220> FEATURE:
<223> OTHER INFORMATION: Fomitiporia mediterranea strain MF3/22 wild-
      type fungus manganese peroxidase 1 (mnp1)

<400> SEQUENCE: 28

Met Val Phe Lys Leu Ser Val Ala Phe Ile Ala Leu Ala Ser Leu Ala
1               5                   10                  15

Ser Ala Ala Thr Leu Lys Arg Ala Ala Cys Pro Gly Gly Lys His Thr
            20                  25                  30

Ala Lys Asn Pro Ala Cys Cys Val Phe Phe Asp Leu Ala Asp Thr Leu
        35                  40                  45

Gln Thr Asp Gln Phe Phe Asn Asn Glu Cys Gly His Ala His Glu
    50                  55                  60

Ser Leu Arg Leu Thr Phe His Asp Ala Ile Gly Phe Ser Ala Ser Gly
65                  70                  75                  80

Lys Leu Lys Gly Asn Gly Ala Asp Gly Ser Ile Met Leu Phe Ala Asp
                85                  90                  95

Thr Asp Lys Thr Glu Leu Asn Asp Pro Ala Asn Ala Gly Ile Asp Asp
            100                 105                 110

Ser Val Asp Leu Leu Ser Pro Leu Leu His Ser Phe Asn Val Thr Ala
        115                 120                 125

Gly Asp Leu Ile Gln Phe Ala Gly Ala Val Ala Val Ser Asn Cys Pro
    130                 135                 140

Gly Ala Pro Gln Leu Glu Phe Leu Ala Gly Arg Pro Asn Ala Thr Ile
145                 150                 155                 160

Pro Ala Gln Gln Gly Thr Val Pro Leu Pro Gln Asp Pro Val Gly Lys
                165                 170                 175

Ile Leu Ala Arg Met Ala Asp Ala Gly Leu Ser Ala Glu Asp Thr Val
            180                 185                 190

Asn Leu Leu Ala Ser His Ser Val Ala Arg Ser Asp Thr Leu Ile Pro
        195                 200                 205

Gly Glu Thr Ala Val Pro Phe Asp Thr Thr Pro Phe Thr Phe Asp Ser
    210                 215                 220

Gln Ile Phe Leu Glu Val Leu Leu Lys Gly Thr Gly Leu Pro Phe Gly
225                 230                 235                 240

Lys Asn Asn Ser Asp Gly Ala Glu Val Leu Ser Pro Leu Pro Asp Glu
                245                 250                 255

Gly Glu Met Arg Leu Gln Ser Asp Phe Ala Ile Ala Arg Asp Pro Gln
            260                 265                 270

Thr Ala Cys Phe Trp Gln Asp Met Ile Asn Gln Gln Ser His Met Met
        275                 280                 285

Thr Ala Phe Gln Thr Ser Met Lys Lys Met Ala Ile Leu Gly His Asp
    290                 295                 300

Arg Asn Gln Leu Ile Asp Cys Ser Glu Ala Val Pro Ala Pro Lys Ala
305                 310                 315                 320

Lys Phe Thr Lys Ser Ile Thr Phe Pro Ala Thr Lys Asn Tyr Ser Asp
```

```
                     325                 330                 335
Ile Gln Gln Val Cys Asn His Pro Phe Pro Thr Leu Ser Thr Asp Pro
                340                 345                 350

Gly Ala Glu Thr Thr Ile Pro Ser Cys Pro Pro Gly Glu Ala Thr Cys
                355                 360                 365

Asp Glu Ser
        370

<210> SEQ ID NO 29
<211> LENGTH: 369
<212> TYPE: PRT
<213> ORGANISM: Fomitiporia mediterranea
<220> FEATURE:
<223> OTHER INFORMATION: Fomitiporia mediterranea strain MF3/22 wild-
      type fungus manganese peroxidase 2 (mnp2)

<400> SEQUENCE: 29

Met Leu Lys Leu Ala Ile Ala Thr Ile Ala Leu Ala Thr Ser Val Ala
1               5                   10                  15

Ala Ala Asn Tyr Lys Arg Val Thr Cys Pro Asp Gly Val Asn Thr Ala
                20                  25                  30

Thr Asn Glu Ala Cys Cys Ala Phe Phe Ala Leu Arg Asp Asp Leu Gln
            35                  40                  45

Asn Asn Leu Phe Glu Gly Glu Cys Gly Glu Asp Val His Glu Ser Leu
        50                  55                  60

Arg Leu Thr Phe His Asp Ala Ile Gly Phe Ser Gly Ser Gly Ala Phe
65                  70                  75                  80

Lys Gly Thr Gly Ala Asp Gly Ser Ile Ile Leu Phe Ser Asp Thr Glu
                85                  90                  95

Leu Ala Asp Pro Ala Asn Ala Gly Ile Asp Asp Pro Val His Ala Ile
            100                 105                 110

Ala Pro Phe Leu Thr Arg His Asn Val Thr Ala Gly Asp Leu Ile Gln
        115                 120                 125

Phe Ala Gly Ala Leu Gly Ile Thr Asn Cys Pro Gly Ala Pro Arg Leu
130                 135                 140

Glu Phe Leu Ala Gly Arg Pro Asn Ala Thr Phe Pro Val Asp Pro Gly
145                 150                 155                 160

Ser Val Pro Leu Pro Gln Ser Pro Ala Asp Leu Ile Leu Ser Arg Met
                165                 170                 175

Glu Asp Gly Gly Phe Ser Asp Ala Glu Thr Ile His Leu Leu Val Ser
            180                 185                 190

His Thr Ile Ala Arg Ser Asp Thr Leu Val Pro Gly His Glu Ala Val
        195                 200                 205

Pro Phe Asp Thr Thr Pro Phe Thr Phe Asp Pro Gln Ile Phe Leu Glu
    210                 215                 220

Val Leu Leu Gln Gly Asn Gly Ile Pro Phe Gly Val Asn Asn Thr Asp
225                 230                 235                 240

Gly Ala Glu Val Asp Ser Pro Leu Pro Gln Ser Gly Glu Met Arg Leu
                245                 250                 255

Gln Ser Asp Phe Val Leu Ala Arg Asp Ser Arg Thr Ala Cys Glu Trp
            260                 265                 270

Gln Ser Met Val Ala Asn Gln Gln Leu Met Met Gln Asn Phe Gln Ser
        275                 280                 285

Ala Met Ala Lys Leu Ala Ile Val Gly His Asn Arg Asn Gln Leu Ile
    290                 295                 300

Asp Cys Ser Glu Leu Ile Pro Ser Pro Ile Ala Pro Val Ser Ser Ala
```

```
            305                 310                 315                 320
Ala Thr Phe Pro Ala Gly Thr Ser Pro Asp Asp Val Gln Gln Ala Cys
                325                 330                 335

Ala Glu Thr Pro Phe Pro Ser Leu Ala Ala Thr Gly Gly Gln Ala Thr
                340                 345                 350

Gln Ile Pro Ala Cys Pro Asp Gly Asp Leu Asn Leu Asp Asp Cys Pro
                355                 360                 365

Ser

<210> SEQ ID NO 30
<211> LENGTH: 371
<212> TYPE: PRT
<213> ORGANISM: Fomitiporia mediterranea
<220> FEATURE:
<223> OTHER INFORMATION: Fomitiporia mediterranea strain MF3/22 wild-
      type fungus manganese peroxidase 3 (mnp3)

<400> SEQUENCE: 30

Met Gly Phe Lys Leu Val Ile Pro Thr Val Ala Leu Ala Ala Leu
1               5                   10                  15

Ala Gly Ala Ala His Ile Lys Arg Ala Thr Cys Pro Asp Gly Asn Thr
                20                  25                  30

Ala Ser Asp Glu Ala Cys Cys Ala Phe Phe Ala Leu Arg Asp Asp Leu
                35                  40                  45

Gln Gln Asn Leu Phe Gln Gly Glu Cys Gly Glu Asp Val His Glu Ser
    50                  55                  60

Leu Arg Leu Thr Phe His Asp Gly Val Ser Phe Ser Leu Thr Gly Gln
65                  70                  75                  80

Phe Ala Gly Gly Gly Ala Asp Gly Ser Ile Leu Leu Phe Ser Asp Ile
                85                  90                  95

Glu Thr Asn Phe Ala Glu Asn Ala Gly Thr Glu Asp Gly Thr Asp Ala
                100                 105                 110

Leu Ala Pro Phe Leu Thr Arg His Leu Val Ser Ala Gly Asp Leu Ile
                115                 120                 125

Gln Phe Ala Ala Ala Val Gly Leu Thr Asn Cys Pro Gly Ala Pro Arg
    130                 135                 140

Leu Gln Phe Leu Ala Gly Arg Pro Asn Ala Thr Ala Pro Ala Gln Asp
145                 150                 155                 160

Gly Ala Ile Pro Gly Pro Ala Asp Thr Val Asp Ser Ile Leu Ser Arg
                165                 170                 175

Phe Ala Asp Ala Gly Phe Thr Ser Ala Glu Val Val His Pro Leu Ala
                180                 185                 190

Ser His Thr Val Ala Arg Ser Asp Thr Ile Ile Pro Gly His Glu Ala
                195                 200                 205

Val Pro Phe Asp Ser Thr Pro Phe Asn Phe Asp Thr Gln Phe Phe Leu
    210                 215                 220

Glu Thr Leu Leu Lys Gly Thr Gly Val Pro Phe Gly Arg Met Glu Pro
225                 230                 235                 240

Asn Ile Thr Gly Gly Glu Val Asp Ser Pro Leu Ser Ala Glu Gly Glu
                245                 250                 255

Met Arg Leu Gln Ser Asp Phe Ala Leu Ala Arg Asp Phe Arg Thr Ala
                260                 265                 270

Cys Glu Trp Gln Ser Met Val Asp Asp Gln Cys Leu Met Val Glu Asn
                275                 280                 285

Phe Arg Asn Ala Met Lys Lys Leu Ser Val Val Gly Gln Asp Thr Ser
    290                 295                 300
```

```
Lys Leu Val Asp Cys Ser Asp Leu Ile Pro Glu Ala Lys Pro Ala Thr
305                 310                 315                 320

Lys Glu His Ala Thr Phe Pro Ala Gly Thr Cys Pro Lys Glu Ile Gln
                325                 330                 335

Gln Ser Cys Lys Ala Pro Phe Pro Arg Leu Ala Val Asp Pro Gly Gln
            340                 345                 350

Pro Thr Gln Ile Pro Gln Cys Pro Asp Gly Ser Leu Asn Pro Ala Asp
        355                 360                 365

Cys Pro Ser
    370

<210> SEQ ID NO 31
<211> LENGTH: 395
<212> TYPE: PRT
<213> ORGANISM: Dichomitus squalens
<220> FEATURE:
<223> OTHER INFORMATION: Dichomitus squalens strain CBS432.34 wild-
      type fungus manganese peroxidase isoform 1 (mnp1)

<400> SEQUENCE: 31

Met Ala Phe Lys Trp Ser Ser Ile Leu Ala Leu Val Thr Leu Ala Thr
1               5                   10                  15

Leu Ala Ser Ala Ala Pro Thr Gln Ser Thr Val Thr Cys Ser Asp Gly
            20                  25                  30

Thr Val Val Pro Asp Ser Val Cys Cys Glu Phe Ile Pro Leu Arg Glu
        35                  40                  45

Ala Leu Asn Asp Gln Val Ile Gln Ser Asp Cys Gly Glu Asp Ala His
    50                  55                  60

Glu Leu Leu Arg Leu Thr Phe His Asp Ala Ile Ala Ile Ser Gln Ser
65                  70                  75                  80

Leu Gly Pro Ser Ala Gly Gly Ala Asp Gly Ser Met Leu Leu Phe
                85                  90                  95

Pro Thr Val Glu Pro Ala Phe Phe Ala Asn Leu Gly Ile Ala Asp Ser
                100                 105                 110

Val Asn Asn Leu Ile Pro Phe Met Ser Gln Phe Pro Asn Ile Ser Pro
            115                 120                 125

Gly Asp Leu Val Gln Phe Ala Gly Ala Val Ala Ile Thr Asn Cys Pro
130                 135                 140

Gly Ala Pro Gln Leu Glu Phe Leu Ala Gly Arg Pro Asn Gly Thr Ala
145                 150                 155                 160

Pro Ala Ile Asp Gly Leu Ile Pro Glu Pro Gln Asp Ser Ile Asp Asp
            165                 170                 175

Ile Leu Ala Arg Phe Asp Asp Ala Gly Gly Phe Thr Pro Phe Glu Val
            180                 185                 190

Val Ser Leu Leu Ala Ser His Thr Val Ala Arg Ala Asp His Val Asp
        195                 200                 205

Pro Thr Leu Asp Ala Ala Pro Phe Asp Ser Thr Pro Phe Thr Phe Asp
        210                 215                 220

Thr Gln Ile Phe Leu Glu Val Leu Leu Lys Gly Thr Gly Phe Pro Gly
225                 230                 235                 240

Thr Asp Asn Asn Thr Gly Glu Val Ala Ser Pro Ile Pro Val Thr Asn
                245                 250                 255

Gly Thr Asp Val Gly Glu Leu Arg Leu Gln Ser Asp Phe Gly Leu Ala
            260                 265                 270

His Asp Ser Arg Thr Ala Cys Phe Trp Gln Gly Phe Val Asn Gln Gln
        275                 280                 285
```

```
Asp Phe Met Ala Gln Ser Phe Lys Ala Ala Met Ala Lys Leu Ala Val
    290                 295                 300

Leu Gly His Asn Ala Ala Asp Leu Val Asn Cys Ser Ala Val Ile Pro
305                 310                 315                 320

Thr Pro Leu Pro Ala Thr Gly Lys Pro Ala Thr Phe Pro Ala Thr Leu
                325                 330                 335

Gly Pro Asp Asp Leu Glu Leu Ser Cys Thr Thr Glu Pro Phe Pro Ser
            340                 345                 350

Leu Thr Thr Asp Pro Gly Ala Gln Glu Thr Leu Ile Pro His Cys Ser
        355                 360                 365

Asp Gly Ser Met Asp Cys Glu Ser Val Gln Phe Asp Gly Pro Ala Thr
    370                 375                 380

Asn Phe Gly Gly Asp Asp Asp Asp Ser
385                 390

<210> SEQ ID NO 32
<211> LENGTH: 390
<212> TYPE: PRT
<213> ORGANISM: Dichomitus squalens
<220> FEATURE:
<223> OTHER INFORMATION: Dichomitus squalens strain CBS432.34 wild-type
      fungus manganese peroxidase isoform 2 (mnp2)

<400> SEQUENCE: 32

Met Ala Phe Lys Leu Trp Ser Met Leu Pro Leu Val Ala Leu Ala Thr
1               5                   10                  15

Val Ala Val Ala Ala Pro Ser Arg Gln Thr Val Cys Ser Asp Gly Thr
            20                  25                  30

Val Val Pro Asp Ser Val Cys Cys Glu Phe Val Pro Leu Ala Gln Ala
        35                  40                  45

Leu Gln Lys Glu Val Leu Met Gly Asp Cys Gly Glu Asp Ala His Glu
    50                  55                  60

Leu Leu Arg Leu Thr Phe His Asp Ala Ile Ala Ile Ser Arg Ser Lys
65                  70                  75                  80

Gly Pro Ser Ala Gly Gly Ala Asp Gly Ser Met Leu Ile Phe Pro
                85                  90                  95

Thr Val Glu Pro Ala Phe Phe Ala Asn Leu Gly Ile Ala Asp Ser Val
            100                 105                 110

Asn Asn Leu Ile Pro Phe Leu Ser Gln Phe Pro Lys Ile Ser Ala Gly
        115                 120                 125

Asp Leu Val Gln Phe Ala Gly Ala Val Ala Val Gly Asn Cys Pro Gly
    130                 135                 140

Ala Pro Gln Leu Glu Phe Arg Ala Gly Arg Pro Asn Ala Thr Ala Pro
145                 150                 155                 160

Ala Ile Glu Gly Leu Ile Pro Glu Pro Gln Asn Asn Ile Thr Glu Ile
                165                 170                 175

Leu Glu Arg Phe Asp Asp Ala Gly Gly Phe Ser Pro Phe Glu Val Val
            180                 185                 190

Ser Leu Leu Ala Ser His Thr Val Ala Arg Ala Asp His Val Asp Pro
        195                 200                 205

Thr Leu Asp Ala Ala Pro Phe Asp Ser Thr Pro Phe Thr Phe Asp Thr
    210                 215                 220

Gln Ile Phe Leu Glu Val Leu Leu Lys Gly Val Gly Phe Pro Gly Thr
225                 230                 235                 240

Gly Asn Asn Thr Gly Glu Val Ser Ser Pro Leu Pro Val Ser Ser Gly
                245                 250                 255
```

```
Thr Asp Val Gly Glu Leu Arg Leu Gln Ser Asp Phe Gly Leu Ala His
            260                 265                 270

Asp Glu Arg Thr Ala Cys Phe Trp Gln Gly Phe Val Asn Glu Gln Glu
            275                 280                 285

Phe Met Ala Gln Ser Phe Lys Ala Ala Met Ala Lys Leu Ala Val Leu
            290                 295                 300

Gly His Asn Ala Asp Asp Leu Val Asp Cys Ser Ala Val Val Pro Lys
305                 310                 315                 320

Pro Lys Pro Ala Thr Gly Lys Pro Ala Ser Phe Pro Ala Thr Lys Gly
            325                 330                 335

Pro Lys Asp Leu Glu Leu Ser Cys Thr Ser Lys Lys Phe Pro Thr Leu
            340                 345                 350

Thr Thr Asp His Gly Ala Gln Glu Thr Leu Ile Pro His Cys Ser Asn
            355                 360                 365

Gly Ser Met Asn Cys Thr Thr Val Gln Phe Asp Gly Pro Ala Thr Asn
            370                 375                 380

Phe Asp Gly Asp Asp Ser
385                 390

<210> SEQ ID NO 33
<211> LENGTH: 378
<212> TYPE: PRT
<213> ORGANISM: Ceriporiopsis rivulosa
<220> FEATURE:
<223> OTHER INFORMATION: Ceriporiopsis rivulosa strain DSM 14618 isolate
      T241i wild-type fungus manganese peroxidase precursor (mnpA)
<220> FEATURE:
<221> NAME/KEY: SIGNAL
<222> LOCATION: (1)...(22)
<223> OTHER INFORMATION: signal peptide
<220> FEATURE:
<221> NAME/KEY: PEPTIDE
<222> LOCATION: (23)...(378)
<223> OTHER INFORMATION: mature peptide

<400> SEQUENCE: 33

Met Ala Phe Ala Ala Leu Ile Ala Val Thr Ala Leu Val Gly Ile Thr
1               5                   10                  15

Arg Ala Ala Pro Thr Ala Val Cys Pro Asp Gly Thr Arg Val Asn Asn
            20                  25                  30

Ala Val Cys Cys Ala Phe Ile Pro Leu Ala Gln Asp Leu Gln Ser Thr
            35                  40                  45

Val Phe Met Asn Asp Cys Gly Glu Asp Ala His Glu Ala Ile Arg Leu
        50                  55                  60

Thr Phe His Asp Ala Val Ala Ile Ser Arg Ser Gln Gly Pro Lys Ala
65                  70                  75                  80

Gly Gly Gly Ala Asp Gly Ser Met Leu Leu Phe Pro Thr Val Glu Pro
            85                  90                  95

Asn Phe Ser Ala Asn Asn Gly Ile Asp Asp Ser Val Asn Asn Leu Ile
            100                 105                 110

Pro Phe Met Ala Lys His Pro Thr Ile Ser Ala Gly Asp Leu Val Gln
            115                 120                 125

Phe Ala Gly Ala Val Ala Leu Ser Asn Cys Pro Gly Ala Pro Arg Leu
            130                 135                 140

Glu Phe Leu Ala Gly Arg Pro Asn His Thr Ile Ala Ala Ile Asp Gly
145                 150                 155                 160

Leu Ile Pro Glu Pro Gln Asp Ser Val Thr Lys Ile Leu Glu Arg Phe
            165                 170                 175
```

```
Glu Asp Ala Gly Gly Phe Thr Pro Phe Glu Val Val Ser Leu Leu Ala
            180                 185                 190

Ser His Thr Val Ala Arg Ala Asp Lys Val Asp Glu Thr Ile Asp Ala
            195                 200                 205

Ala Pro Phe Asp Ser Thr Pro Thr Phe Asp Thr Gln Val Phe Leu
    210                 215                 220

Glu Val Leu Leu Lys Gly Val Asp Phe Pro Gly Thr Asp Asn Asn Thr
225                 230                 235                 240

Gly Glu Val Ala Ser Pro Leu Pro Lys Gly Ser Gly Asn Asp Thr Gly
            245                 250                 255

Glu Met Arg Leu Gln Ser Asp Phe Ala Leu Ala Arg Asp Glu Arg Thr
            260                 265                 270

Ala Cys Phe Trp Gln Gly Phe Val Asn Gln Gln Glu Phe Met Ser Ser
            275                 280                 285

Ser Phe Lys Ala Ala Met Ser Lys Leu Ala Ile Leu Gly His Asn Arg
            290                 295                 300

Ala Ser Leu Ile Asp Cys Ser Asp Val Val Pro Ile Pro Lys Pro Ala
305                 310                 315                 320

Val Asn Lys Pro Ala Ser Phe Pro Ala Thr Thr Gly Pro Lys Asp Leu
            325                 330                 335

Glu Leu Thr Cys Lys Leu Glu Arg Phe Pro Thr Leu Thr Val Asp His
            340                 345                 350

Gly Ala Thr Gln Thr Leu Ile Pro His Cys Ser Asn Gly Gly Gln Asp
            355                 360                 365

Cys Pro Ala Ile Gln Phe Asp Gly Pro Ala
            370                 375

<210> SEQ ID NO 34
<211> LENGTH: 363
<212> TYPE: PRT
<213> ORGANISM: Ceriporiopsis rivulosa
<220> FEATURE:
<223> OTHER INFORMATION: Ceriporiopsis rivulosa strain DSM 14618 isolate
      T241i wild-type fungus manganese peroxidase precursor (mnpB)
<220> FEATURE:
<221> NAME/KEY: SIGNAL
<222> LOCATION: (1)...(23)
<223> OTHER INFORMATION: signal peptide
<220> FEATURE:
<221> NAME/KEY: PEPTIDE
<222> LOCATION: (24)...(363)
<223> OTHER INFORMATION: mature peptide

<400> SEQUENCE: 34

Met Ala Phe Lys Ser Leu Ala Ala Leu Val Thr Leu Leu Ser Ile Gln
1               5                   10                  15

Ala Val His Gly Ala Ile Thr Arg Arg Val Thr Cys Pro Asp Gly Val
            20                  25                  30

Asn Thr Ala Thr Asn Ala Ala Cys Cys Pro Leu Phe Ala Val Arg Asp
        35                  40                  45

Asp Ile Gln Glu Phe Leu Phe Asp Gly Gly Lys Cys Gly Glu Glu Val
    50                  55                  60

His Glu Ser Leu Arg Leu Thr Phe His Asp Ala Ile Gly Phe Ser Pro
65                  70                  75                  80

Ser Leu Thr Ala Gln Gly Thr Phe Gly Gly Gly Ala Asp Gly Ser
            85                  90                  95

Ile Ala Thr Phe Glu Ser Ile Glu Thr Ala Tyr His Ala Asn Thr Gly
            100                 105                 110

Ile Asp Glu Ile Ile Asn Glu Gln Ala Pro Phe Ile Val Lys His Asn
```

```
                115                 120                 125
Met Thr Ala Gly Asp Phe Ile Gln Phe Ala Gly Ala Val Gly Val Ser
130                 135                 140

Asn Cys Ala Gly Ala Pro Arg Leu Glu Phe Leu Leu Gly Arg Pro Pro
145                 150                 155                 160

Ala Thr Ala Pro Ala Pro Asp Lys Thr Val Pro Glu Pro Phe Asp Thr
                165                 170                 175

Val Asp Ser Ile Leu Ala Arg Phe Ala Asp Ala Gly Phe Ser Pro Gln
                180                 185                 190

Glu Val Ile Ala Leu Leu Ala Ser His Ser Val Ala Ala Ala Asp His
                195                 200                 205

Val Asp Pro Ala Ile Pro Gly Thr Pro Phe Asp Ser Thr Pro Ser Asp
210                 215                 220

Phe Asp Ser Gln Ile Phe Ile Glu Val Gln Leu Arg Gly Thr Leu Phe
225                 230                 235                 240

Pro Gly Thr Gly Gly Asn Gln Gly Glu Val Glu Ser Pro Tyr Pro Gly
                245                 250                 255

Glu Ile Arg Leu Gln Ser Asp His Thr Leu Ala Arg Asp Ser Arg Thr
                260                 265                 270

Ala Cys Phe Trp Gln Ala Leu Ala Asn Asp Gln Ala Gln Ile Gln Ala
                275                 280                 285

Gln Phe Lys Ala Ala Met Ala Lys Leu Ala Val Val Gly Gln Asp Val
                290                 295                 300

Ser Gln Met Val Asp Cys Ser Glu Val Ile Pro Val Pro Ala Pro Pro
305                 310                 315                 320

Ala Thr Thr Pro His Ile Pro Ala Gly Leu Ser Gln Asn Asn Ile Glu
                325                 330                 335

Gln Ala Cys Ala Thr Ala Ala Phe Pro Thr Leu Pro Val Asp Val Gly
                340                 345                 350

Pro Gln Thr Ser Ile Leu Pro Val Pro Ala Ser
                355                 360

<210> SEQ ID NO 35
<211> LENGTH: 357
<212> TYPE: PRT
<213> ORGANISM: Spongipellis sp.
<220> FEATURE:
<223> OTHER INFORMATION: Spongipellis sp. specimen voucher FERM P-18171
      wild-type white-rot fungus manganese peroxidase 1 precursor
<220> FEATURE:
<221> NAME/KEY: SIGNAL
<222> LOCATION: (1)...(25)
<223> OTHER INFORMATION: signal peptide
<220> FEATURE:
<221> NAME/KEY: PEPTIDE
<222> LOCATION: (26)...(357)
<223> OTHER INFORMATION: mature peptide

<400> SEQUENCE: 35

Met Ala Phe Lys Ser Leu Ala Ala Phe Leu Thr Leu Ala Ala Phe Gln
1               5                   10                  15

Val Ala Asn Ala Ala Leu Thr Arg Arg Val Ala Cys Pro Asp Gly Val
                20                  25                  30

Asn Thr Ala Thr Asn Ala Ala Cys Cys Ser Leu Phe Ala Leu Arg Asp
            35                  40                  45

Asp Leu Gln Gln Asn Leu Phe Asp Asn Gly Gln Cys Gly Glu Asp Val
        50                  55                  60

His Glu Ser Leu Arg Leu Thr Phe His Asp Ala Ile Gly Ile Gly Ser
65                  70                  75                  80
```

Asn Gly Gly Gly Gly Ala Asp Gly Ser Ile Ala Ile Phe Glu Asp Ile
                85                  90                  95

Glu Thr Ala Phe His Ala Asn Ala Gly Ile Asp Glu Ile Ile Asn Glu
            100                 105                 110

Gln Lys Pro Phe Leu Ala Arg His Asn Ile Thr Val Gly Asp Phe Ile
        115                 120                 125

Gln Phe Ala Gly Ala Leu Gly Val Ser Asn Cys Pro Gly Ala Pro Arg
    130                 135                 140

Leu Pro Val Phe Ile Gly Arg Pro Asn Ala Val Ala Pro Ala Pro Asp
145                 150                 155                 160

Lys Thr Val Pro Glu Pro Phe Asp Ser Val Asp Thr Ile Leu Ala Arg
                165                 170                 175

Phe Ala Asp Ala Gly Asn Phe Ser Thr Val Glu Val Val Trp Leu Leu
            180                 185                 190

Ile Ser His Thr Ile Ala Ala Asp Leu Val Asp Pro Thr Ile Pro
        195                 200                 205

Gly Thr Pro Phe Asp Ser Thr Pro Glu Thr Phe Asp Thr Gln Phe Phe
    210                 215                 220

Val Glu Thr Gln Leu Lys Gly Thr Leu Phe Pro Gly Thr Ala Gly Asn
225                 230                 235                 240

Gln Gly Glu Val Glu Ser Pro Leu Gln Gly Glu Ile Arg Leu Gln Ser
                245                 250                 255

Asp Phe Glu Leu Ala Arg Asp Ser Arg Thr Ala Cys Glu Trp Gln Ser
            260                 265                 270

Phe Val Asn Asn Gln Arg Lys Leu Thr Asn Arg Phe Gln Ala Val Phe
        275                 280                 285

Thr Lys Met Thr Val Leu Gly Asn Asp Val Asn Ser Leu Ile Asp Cys
    290                 295                 300

Ser Glu Leu Ile Pro Glu Pro Ala Phe Thr Gly Ser Ala Thr Phe
305                 310                 315                 320

Pro Ala Gly Phe Ser Val Asn Asp Val Glu Gln Ala Cys Glu Ala Thr
                325                 330                 335

Pro Phe Pro Thr Leu Ala Thr Asp Pro Gly Pro Val Thr Ser Val Ala
            340                 345                 350

Pro Val Pro Pro Ser
        355

<210> SEQ ID NO 36
<211> LENGTH: 390
<212> TYPE: PRT
<213> ORGANISM: Phlebia radiate
<220> FEATURE:
<223> OTHER INFORMATION: Phlebia radiate strain 79 wild-type fungus
      manganese peroxidase 2 (mnp2)
<220> FEATURE:
<221> NAME/KEY: SIGNAL
<222> LOCATION: (1)...(23)
<223> OTHER INFORMATION: signal peptide
<220> FEATURE:
<221> NAME/KEY: PEPTIDE
<222> LOCATION: (24)...(390)
<223> OTHER INFORMATION: mature peptide

<400> SEQUENCE: 36

Met Ala Phe Asn Phe Ala Ala Ile Leu Ala Phe Val Ser Leu Ala Ala
1               5                   10                  15

Val Thr Ser Ala Ala Pro Ser Lys Thr Thr Cys Ser Asn Gly Val Val
            20                  25                  30

Val Pro Asp Ala Val Cys Cys Asp Phe Val Pro Leu Ala Ser Ala Leu
                35                  40                  45

Gln Ser Glu Val Leu Met Gly Asp Cys Gly Asp Ala His Glu Leu
 50                  55                  60

Val Arg Leu Ile Phe His Asp Ala Ile Ala Ile Ser Gln Ser Met Gly
 65                  70                  75                  80

Pro Ser Ala Gly Gly Gly Ala Asp Gly Ser Met Leu Ile Phe Pro Thr
                85                  90                  95

Val Glu Pro Ala Phe Phe Pro Asn Leu Gly Ile Ala Asp Ser Val Asn
                100                 105                 110

Asn Leu Ile Pro Phe Leu Ser Gln Phe Pro Thr Ile Ser Ala Gly Asp
                115                 120                 125

Leu Val His Phe Ala Gly Ala Val Ala Ile Ser Asn Cys Pro Gly Ala
130                 135                 140

Pro Gln Leu Glu Phe Leu Ala Gly Arg Pro Asn Ala Thr Ala Pro Ala
145                 150                 155                 160

Ile Asp Gly Leu Ile Pro Glu Pro Gln Asp Val Thr Lys Ile Leu
                165                 170                 175

Ala Arg Phe Lys Asp Ala Gly Asn Phe Ser Pro Ala Glu Val Val Ala
                180                 185                 190

Leu Leu Ala Ser His Ser Ile Ala Arg Ala Asp His Val Asp Pro Thr
                195                 200                 205

Leu Asp Ala Ala Pro Phe Asp Ser Thr Pro Phe Asp Phe Asp Thr Gln
210                 215                 220

Val Phe Leu Glu Val Leu Leu Lys Gly Val Gly Phe Pro Gly Leu Ala
225                 230                 235                 240

Asn Asn Thr Gly Glu Val Ser Ser Pro Leu Pro Val Thr Asp Gly Thr
                245                 250                 255

Asp Val Gly Glu Leu Arg Leu Gln Ser Asp Phe Ala Leu Ala Arg Asp
                260                 265                 270

Glu Arg Thr Ala Cys Ala Trp Gln Ser Phe Val Asn Glu Gln Glu Ala
                275                 280                 285

Met Ala Thr Ala Phe Lys Asn Ala Val Lys Lys Leu Ala Val Leu Gly
                290                 295                 300

His Asn Arg Asn Asp Leu Val Asp Cys Ser Ala Val Val Pro Val Pro
305                 310                 315                 320

Lys Pro Ala Thr Gly Thr Pro Ala Thr Phe Pro Ala Ser Thr Gly Pro
                325                 330                 335

Gln Asp Leu Glu Leu Thr Cys Thr Thr Glu Pro Phe Pro Thr Leu Ser
                340                 345                 350

Thr Ala Pro Gly Ala Gln Gln Thr Leu Ile Pro His Cys Ser Asp Gly
                355                 360                 365

Thr Met Thr Cys Asn Ser Val Gln Phe Asp Gly Pro Ala Thr Asn Phe
370                 375                 380

Gly Gly Ala Asp Asp Ser
385                 390

<210> SEQ ID NO 37
<211> LENGTH: 389
<212> TYPE: PRT
<213> ORGANISM: Gelatoporia subvermispora
<220> FEATURE:
<223> OTHER INFORMATION: Gelatoporia subvermispora strain FP 105752
      wild-type fungus manganese-dependent peroxidase precursor
      (MnP3, mnp3)
<220> FEATURE:
<221> NAME/KEY: SIGNAL

```
<222> LOCATION: (1)...(24)
<223> OTHER INFORMATION: signal peptide
<220> FEATURE:
<221> NAME/KEY: PEPTIDE
<222> LOCATION: (25)...(389)
<223> OTHER INFORMATION: mature peptide

<400> SEQUENCE: 37
```

Met Ala Phe Thr Ser Leu Leu Ala Ile Val Ala Leu Ala Ala Thr Val
1               5                   10                  15

Arg Gly Ala Pro Ala Ser Ser Val Thr Cys Ser Asp Gly Thr Ala
            20                  25                  30

Val Pro Asp Ala Met Cys Cys Asp Phe Ile Pro Leu Ala Gln Asp Leu
        35                  40                  45

Gln Ser Met Val Leu Gln Asn Gln Cys Gly Glu Asp Ala His Glu Ile
    50                  55                  60

Ile Arg Leu Thr Phe His Asp Ala Ile Ala Ile Ser Gln Ser Leu Gly
65              70                  75                  80

Pro Ser Ala Gly Thr Gly Ala Asp Gly Ser Met Leu Leu Phe Pro Leu
                85                  90                  95

Val Glu Pro Glu Phe Ala Ala Ser Asn Gly Ile Asp Asp Ser Val Asn
            100                 105                 110

Asn Leu Ile Pro Phe Leu Ser Ser His Pro Asn Ile Ser Ala Gly Asp
        115                 120                 125

Leu Val Gln Phe Ala Gly Ala Val Ala Leu Thr Asn Cys Pro Gly Ala
    130                 135                 140

Pro Arg Val Asn Phe Leu Ala Gly Arg Lys Asn Ala Val Ala Pro Ala
145                 150                 155                 160

Ile Asp Gly Leu Ile Pro Glu Pro Gln Asp Asn Val Thr Ser Ile Leu
                165                 170                 175

Ala Arg Phe Ala Asp Ala Gly Asn Phe Ser Pro Phe Glu Val Val Ser
            180                 185                 190

Leu Leu Ala Ser His Ser Val Ala Arg Ala Asp Lys Val Asp Pro Thr
        195                 200                 205

Leu Asp Ala Ala Pro Phe Asp Ser Thr Pro Phe Thr Phe Asp Thr Gln
    210                 215                 220

Val Phe Leu Glu Val Leu Leu Lys Gly Val Gly Phe Pro Gly Thr Asp
225                 230                 235                 240

Asn Asn Thr Gly Glu Val Ala Ser Pro Leu Pro Phe Gly Asp Thr Ser
                245                 250                 255

Thr Gly Val Asn Asp Thr Gly Met Met Arg Leu Gln Ser Asp Phe Ala
            260                 265                 270

Leu Ala Arg Asp Glu Arg Thr Ala Cys Phe Trp Gln Ser Phe Val Asp
        275                 280                 285

Gln Gln Asp Leu Met Ala Gln Ser Phe Gln Ala Ala Phe Glu Lys Leu
    290                 295                 300

Ala Ile Leu Gly Ser Ser Ala Ala Asp Leu Val Asn Cys Ser Ala Val
305                 310                 315                 320

Val Pro Leu Ser Val Gly Pro Val Thr Ala Pro Ala Thr Phe Pro Ala
                325                 330                 335

Thr Thr Gly Pro Gln Asp Leu Gln Leu Thr Cys Thr Thr Glu Thr Phe
            340                 345                 350

Pro Ser Leu Ser Ile Asp Pro Gly Ala Thr Glu Thr Leu Ile Pro His
        355                 360                 365

```
Cys Pro Asp Gly Ser Glu Asp Cys Pro Thr Val Gln Phe Ser Gly Pro
    370                 375                 380

Ala Thr Asp Ser Pro
385
```